(12) United States Patent
Selifonov et al.

(10) Patent No.: US 8,546,519 B2
(45) Date of Patent: Oct. 1, 2013

(54) POLYKETAL COMPOUNDS, SYNTHESIS, AND APPLICATIONS

(75) Inventors: Sergey Selifonov, Plymouth, MN (US); Scott D. Rothstein, Sauk Rapids, MN (US); Douglas A. Wicks, Plymouth, MN (US); Brian D. Mullen, Plymouth, MN (US); Tara J. Mullen, Plymouth, MN (US); Jason D. Pratt, Minneapolis, MN (US); Charles T. Williams, Pittsburg, PA (US); Chunyong Wu, Plymouth, MN (US); Ning Zhou, St. Paul, MN (US)

(73) Assignee: Segetis, Inc., Golden Valley, MN (US)

( * ) Notice: Subject to any disclaimer, the term of this patent is extended or adjusted under 35 U.S.C. 154(b) by 327 days.

(21) Appl. No.: 12/682,267

(22) PCT Filed: Oct. 9, 2008

(86) PCT No.: PCT/US2008/079337
§ 371 (c)(1),
(2), (4) Date: Sep. 30, 2010

(87) PCT Pub. No.: WO2009/049041
PCT Pub. Date: Apr. 16, 2009

(65) Prior Publication Data
US 2011/0021658 A1    Jan. 27, 2011

Related U.S. Application Data

(60) Provisional application No. 60/960,626, filed on Oct. 9, 2007, provisional application No. 60/960,627, filed on Oct. 9, 2007, provisional application No. 60/960,628, filed on Oct. 9, 2007, provisional application No. 61/084,401, filed on Jul. 29, 2008.

(51) Int. Cl.
*C08G 4/00* (2006.01)
*C08G 63/00* (2006.01)
*C08G 65/34* (2006.01)

(52) U.S. Cl.
USPC .......................... 528/425; 528/271; 528/220

(58) Field of Classification Search
USPC ......................................... 528/271, 220, 425
See application file for complete search history.

(56) References Cited

U.S. PATENT DOCUMENTS 5,998,092 A    12/1999    McCulloch et al.

FOREIGN PATENT DOCUMENTS

| SU | 722912 | 6/1978 |
|---|---|---|
| WO | WO03064866 A1 | 8/2003 |
| WO | WO2007/062118 A2 | 5/2007 |

OTHER PUBLICATIONS

Grabarnick et al; On five—species; Mar. 2000; American Chemical Society; Chem Abstract 132: 308566.*
Lenz et al; Structure—repeating units; May 1984; Americn Chemical Society; Chem Abstract 72; 122322.*
Lenz et al; Structure—poly(acetals); May 1984; Macromolecules (19690, 2(2), 129-36.*

(Continued)

*Primary Examiner* — Duc Truong
(74) *Attorney, Agent, or Firm* — Cantor Colburn LLP

(57) ABSTRACT

The invention relates to polyketal compounds. The compounds are synthesized by the selective ketalization of oxocarboxylic acids, e.g. keto acids and semialdehydes, and esters thereof with tetrols and higher polyols that products two or more cyclic ketal ester moieties per molecule, wherein the cyclic ketal moieties are situated in a bis-, tris-, or polyketal conformation. The invention further relates to applications of these compounds and subsequent reactions thereof.

13 Claims, 9 Drawing Sheets

(56) References Cited

OTHER PUBLICATIONS

Lenz et al; poly(ester-acetals)—azelaaldehydate; May 1984; American Chemical Society; Chem Abstract 70:97280.*

Carey, Francis A. and Sundberg, Richard J., Advanced Organic Chemistry, Second Edition, Part B: Reactions and Synthesis Plenum Press, NY (1983) p. 539- 552.

Chirila, Traian, "Cicloacetal-esteri penta-se hexaatomici", Revista de Chimie 28(8), 730-733 (1977) [with English abstract].

Gelas, Jacques and Thiallier, Andre, "Synthese du 4-oxo et de 4-hydroxy-3,6,8-trioxabicyclo[3.2.1]octanes", Carbohydrate Research 30(1), 1973, p. 21-34 1973 (with English abstract).

Ono, Daisuke, et al., "Preparation, Surface-Active Properties and Decomposition Profiles of a New "Soap" Bearing a 1-3-Dioxolane Ring", J. Am. Oil Chem. Soc. 70(1), (1993) p. 29-36.

International Search Report for PCT/US2008/079337, mailed Apr. 21, 2009, 4 pages.

* cited by examiner

POLYKETAL COMPOUNDS, SYNTHESIS, AND APPLICATIONS

CROSS-REFERENCE TO RELATED APPLICATION

This application is a National Stage application under 35 U.S.C. §371 to International Application No. PCT/US2008/079337 having an International Filing Date of Oct. 9, 2008, which claims benefit of under 35 U.S.C. §119(e) to U.S. Provisional Patent Application No. 60/960,626, filed on Oct. 9, 2007, which is incorporated by reference in its entirety herein; this application further claims the benefit of U.S. Provisional Patent Application No. 60/960,627, filed on Oct. 9, 2007, which is incorporated by reference in its entirety herein; this application further claims the benefit of U.S. Provisional Patent Application No. 60/960,628, filed on Oct. 9, 2007, which is incorporated by reference in its entirety herein; this application further claims the benefit of the U.S. Provisional Patent Application No. 61/084,401, filed on Jul. 29, 2008, which is incorporated by reference in its entirety herein.

FIELD OF THE INVENTION

The invention relates to polyketal compounds. The compounds are synthesized by the selective ketalization of oxocarboxylic acids, e.g. keto acids and semialdehydes, and esters thereof with tetrols and higher polyols that products two or more cyclic ketal ester moieties per molecule, wherein the cyclic ketal moieties are situated in a bis-, tris-, or polyketal conformation. The invention further relates to applications of these compounds and subsequent reactions thereof.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

It is desirable to provide commonly used materials, such as surfactants, plasticizers, solvents, and polymers, from renewable feedstocks as a source of chemical building blocks. It is desirable to provide chemical building blocks that are chemically and thermally stable. It is desirable to provide chemical building blocks having multiple functionalities for subsequent reactions. It is desirable to provide such materials by simple and reproducible methods that can be carried out with ease.

A potential source of materials that are useful as chemical building blocks are cyclic ketals and acetals of oxocarboxylates with polyols. It is known, for example, that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" 2$^{nd}$ ed., © 1983, Plenum Press, NY, N.Y., p. 544). The 1,2 and 1,3 configurations of hydroxyl groups on a hydrocarbon chain are shown below as (a) and (b), respectively.

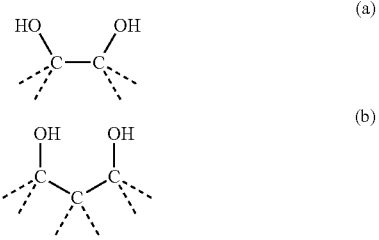

Diols such as 1,2-ethane diol (ethylene glycol) and 1,3 propanediol (propylene glycol) are examples of such polyols. Diols having a 1,2 hydroxyl group configuration will form dioxolanes when reacted with ketone or aldehyde moieties, while 1,3 diols will form dioxanes.

Various ketals arising from the reaction of oxocarboxylic acids and esters thereof with diols and triols are known. Ono et al., *J. Am. Oil Chem. Soc.* 70(1), 29 (1993) disclose ketalization of ethyl pyruvate, ethyl acetoacetate, and ethyl levulinate with various 1-O-alkyl glycerols (diols). Okohara et al., JP 04217972, similarly disclose ketalization of ethyl levulinate with 1-O-alkyl glycerols, followed by saponification of the ester moiety. McCullough et al., U.S. Pat. No. 5,998,092 disclose the ketalization of two keto acids with ethylene glycol. Chirila, *Revistade Chimie* 28(8), 730-3 (1977) discloses the 1:1 adduct of acetoacetate esters with glycerol. Gelas, *Carbohydrate Research* 30(1), 21-34 (1973) and Rakhmankulov et al., SU 722912 disclose the 1:1 adduct of pyruvate esters with glycerol and subsequent bicyclic lactone formation.

Ketals of glycerol and levulinic acid or an ester thereof are described in U.S. patent application Ser. No. 11/915,549, the entirety of which is incorporated herein by reference. The ketal reaction product of glycerol with a levulinate results in the ketal acid or ketal ester shown below,

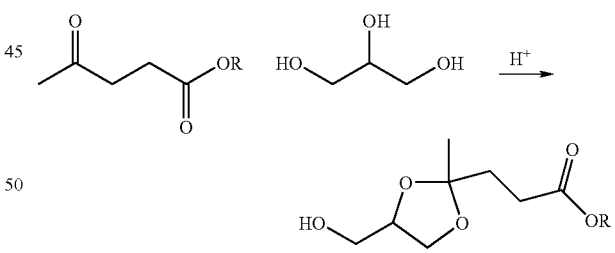

wherein R is hydrogen or an alkyl group. The use of levulinate compounds and glycerol based compounds is particularly useful as both of these starting materials arise from renewable feedstocks. Further, the ketal reaction products are useful for synthesis of a wide variety of surfactants, plasticizers, polymers, and the like.

Efficient synthetic routes to form various compounds based on the ketals or acetals of keto acids, semialdehydes, and the esters thereof are described in U.S. Patent Application No. 61/048,339, the entirety of which is incorporated herein by reference. The synthetic routes described in this applications is useful as a basis for efficient reaction of a number of oxocarboxylic acids and esters thereof with alcohols.

It is desirable to provide new starting materials and synthetic routes to form new varieties of chemical building blocks for monomers, plasticizers, surfactants, and polymers. It is desirable to provide chemical building blocks that arise solely from renewable feedstocks. It is desirable to facilitate synthesis of chemical building blocks that is simple, inexpensive, and scalable for commercialization purposes.

SUMMARY

Disclosed herein are polyketal compounds having at least two contiguous or semi-contiguous ketal moieties per molecule. These compounds are useful in numerous applications and materials having physical properties suitable for replacing present fully petrochemical-based materials such as plasticizers, surfactants, coatings additives, and other industrially useful applications.

The polyketal compounds of the invention are based on selective ketalization of oxocarboxylic acids and esters thereof, with tetrols, hexols, and higher polyols. We have found that polyols having two or more pairs of hydroxyl groups situated in 1,2 and 1,3 positions are able to react with multiple equivalents of keto esters, semialdehydes, or esters thereof to provide bisketals, trisketals, and higher polyketals. This is true even where the hydroxyl pairs are present in a contiguous position relative to neighboring hydroxyl pair(s), e.g. in forming the bisketal of erythritol or the trisketal of sorbitol. The ability to form contiguous ketals is surprising because the reaction to form one ketal group on a polyol would be expected to reduce reactivity of remaining hydroxyl groups that are situated on contiguous carbons.

The polyketal compounds of the invention are useful in a number of applications. Nonlimiting examples of uses for the compounds of the invention include uses as solvents, plasticizers, surfactants, coalescing solvents, compatibilizing solvents, interfacial modifiers, and phase transfer materials in one or more formulations. Additionally, the polyketal compounds of the invention supply at least two carboxyl functionalities on a single molecule which in turn supply chemically reactive sites for forming a wide variety of dimeric, oligomeric, or polymeric materials with a wide scope of applications. Thus, the compounds of the invention can be employed as monomers having two or more reactive carboxyl functionalities per molecule, suitable for synthesis of species such as polyesters, copolyesters, polymeric polyols, polyurethanes, poly(urethane urea)s, poly(ester urethane)s, and polycarbonates; additionally, acrylates and methacrylates, allylic functional polyketals, epoxy functional polyketals, and polymers formed from these, and the like. In some embodiments, the multiple functionalities present in the structures of the polyketals are useful as crosslinkers for one or more polymeric networks.

Additional advantages and novel features of the invention will be set forth in part in the description that follows, and in part will become apparent upon examination of the following, or may be learned through routine experimentation upon practice of the invention.

DETAILED DESCRIPTION

Figure 1A:
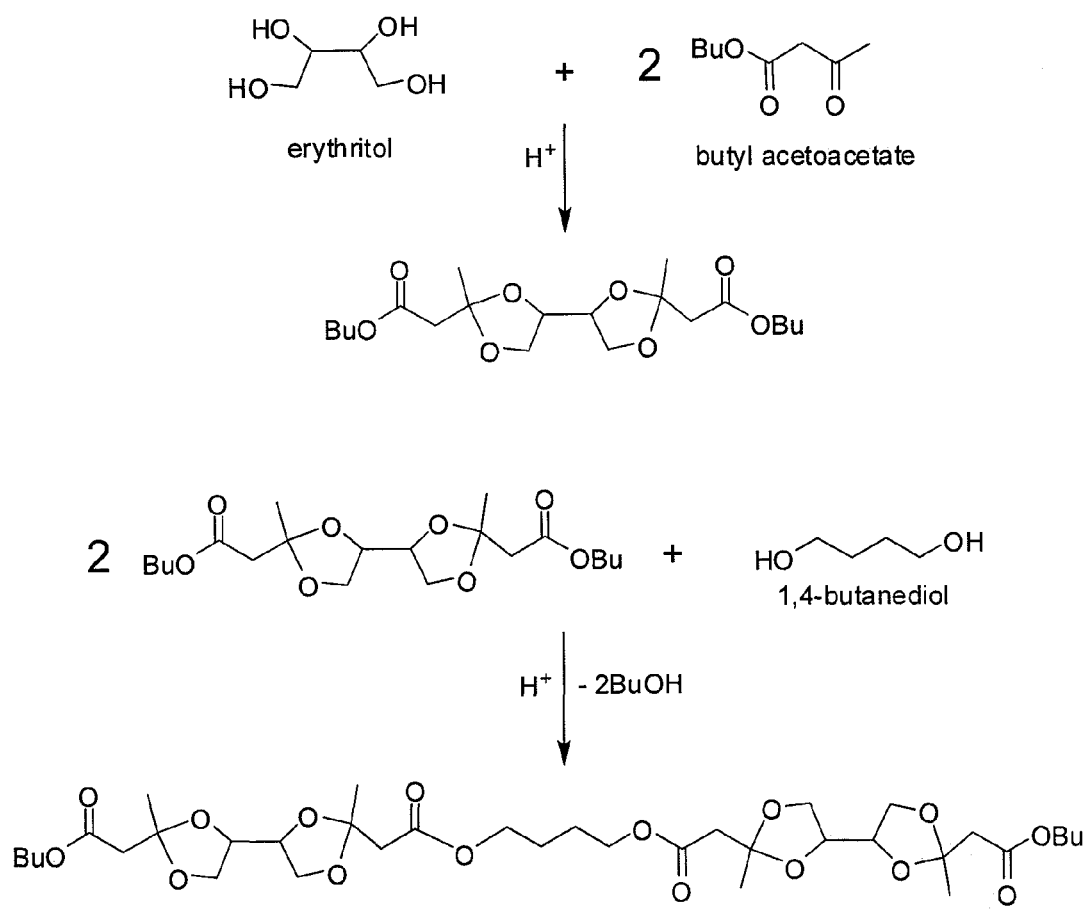
FIG. 1A-1D shows synthetic paths to reach the compounds of the invention.

Various embodiments will be described in detail. Reference to various embodiments does not limit the scope of the claims attached hereto. Additionally, any examples set forth in this specification are not intended to be limiting and merely set forth some of the many possible embodiments for the appended claims.

The compounds of the invention have, in embodiments, one or more isomers. Where an isomer can exist, it should be understood that the invention embodies all isomers thereof, including stereoisomers, conformational isomers, and cis, trans isomers; isolated isomers thereof; and mixtures thereof.

In some embodiments, the compounds of the invention have structure I:

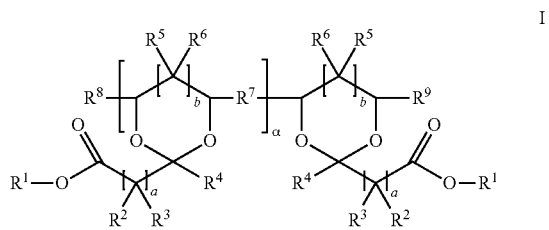

wherein
- α is an integer of at least 1;
- $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ may be the same or different for each occurrence;
- $R^2$, $R^3$, $R^4$, $R^5$, and $R^6$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ may be the same or different for each occurrence;
- $R^7$ is a covalent bond, methylene, ethylene, hydroxymethylene, oxygen, or —$CH_2$—O—$CH_2$— and $R^7$ is the same or different for each occurrence;
- $R^8$ and $R^9$ are independently hydrogen, a linear, branched, or cyclic alkyl, a linear, branched, or cyclic alkenyl, alkynyl, aryl, alkaryl, or a polymeric moiety; and optionally contains one or more heteroatoms;
- a is 0 or an integer of 1 to 12; and
- b is 0 or 1, wherein b=0 indicates a five membered ring:

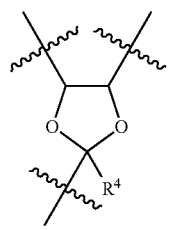

and b=1 indicates a 6 membered ring:

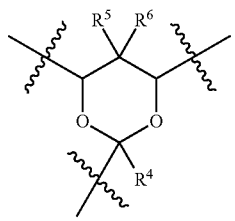

and b may be the same or different for each occurrence.

The compounds of the invention are adducts of at least two molar equivalents of an oxocarboxylate with one molar equivalent of a first polyol which is a tetrol or higher polyol. At least two pairs of hydroxyl groups on the polyol are present either on contiguous carbon atoms or have one carbon atom spaced between hydroxyl-bearing contiguous carbon atoms. These conformations are shown as (a) and (b) below, respectively, for a hydrocarbon based polyol.

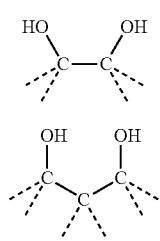

As defined herein, the term "ketal" means the cyclic adduct of one equivalent of a first polyol, as defined above, with one equivalent of an oxocarboxylate, which is a keto acid, semialdehyde, or ester thereof, to form the corresponding cyclic ketal acid, acetal acid, or ester thereof. As defined herein, the term "contiguous" means a chemical moiety separated from a neighboring chemical moiety solely by a covalent bond. As defined herein, the term "semi-contiguous" means a chemical moiety separated from a neighboring chemical moiety by a methylene group, ethylene group, hydroxymethylene group, an oxygen atom, or a —CH$_2$—O—CH$_2$— group. For the purposes of the invention, cyclic ketal-forming polyols are polyols wherein hydroxyl moieties are situated in pairs as shown in a) and b) above.

As defined herein, the term "bisketal" means the ketal adduct of two molar equivalents of an oxocarboxylate with one equivalent of a tetrol or higher polyol to form two contiguous or semicontiguous ketal groups. As defined herein, the term "trisketal" means the ketal reaction product, as defined above, of three equivalents of an oxocarboxylate with one equivalent of a hexyl or higher polyol to form three contiguous or semicontiguous ketal groups. And the term "polyketal" as defined herein means the ketal reaction product, as defined above, of at least two equivalents of an oxocarboxylate with one equivalent of a tetrol or higher polyol to form at least two contiguous or semicontiguous ketal groups.

In embodiments, the number of ketal units is determined by the value of a. The number $\alpha$ is at least 1, but in some embodiments $\alpha$ is up to 100; in other embodiments the value of $\alpha$ is up to about 1000. In some embodiments, the polyketals of the invention are based on the reaction of poly(vinyl alcohol) with one or more oxocarboxylic acids or esters to form the corresponding polyketal. In such embodiments, all values of b are 1 and all $R^5$ and $R^6$ are hydrogen. In some such embodiments, the value of $\alpha$ is as much as 100; in other such embodiments the value of $\alpha$ is as high as 250. The invention contemplates both poly(vinyl alcohol) as the basis for polyketals of the invention as well as copolymers thereof. For example, in embodiments, R8, R9, or both are polymeric moieties that are not poly(vinyl alcohol). For example, the polymeric moieties are, in certain embodiments, polyethylene or polypropylene residues; in other embodiments the polymeric moieties are poly(vinyl acetate) residues; other embodiments will be readily envisioned.

In some embodiments, the invention contemplates a bisketal structure having a Spiro group. This structure can be represented as structure II:

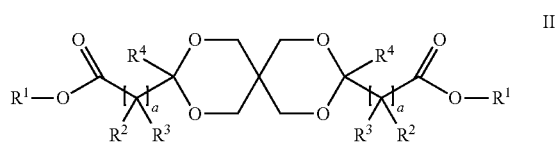

wherein
each $R^1$ is independently hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms;

each $R^2$ and $R^3$ are independently hydrogen, a linear, branched, or cyclic alkyl, a linear, branched, or cyclic alkenyl, alkynyl, aryl, or alkaryl; and optionally contain one or more heteroatoms;

each $R^4$ is independently linear, branched, or cyclic alkyl; linear, branched, or cyclic alkenyl; alkynyl; aryl; or alkaryl; and optionally contains one or more heteroatoms; and each a is independently 0 or an integer of 1 to 12.

The compounds of structure II are bisketal adducts of pentaerythritol, $C(CH_2OH)_4$, with two molar equivalents of a keto acid or ester thereof.

Structures I and II contemplate many useful embodiments. Various embodiments of the compounds are useful in one or more formulations; other embodiments are useful as chemical building blocks in subsequent reactions. Some representative and nonlimiting examples of compounds corresponding to structures I and II are shown below as structures Ia to Ih and IIa, wherein each R is independently hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms:

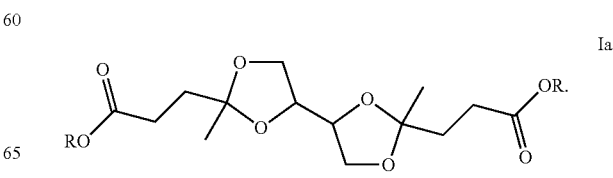

Ib
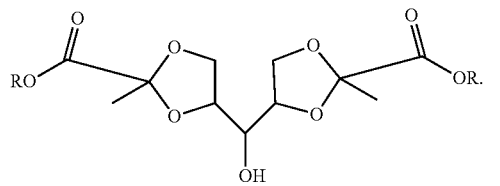

Ic
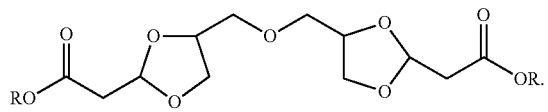

Id
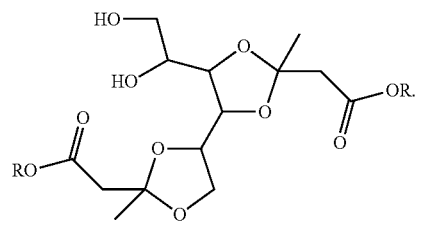

Ie
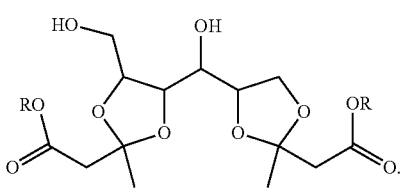

If
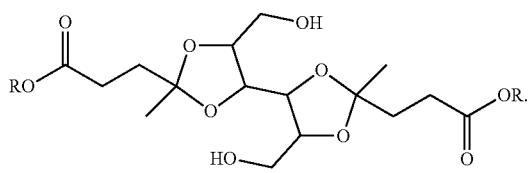

Ig
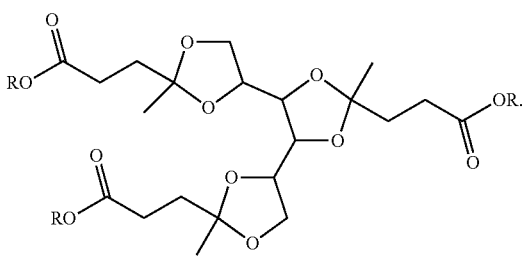

Ih
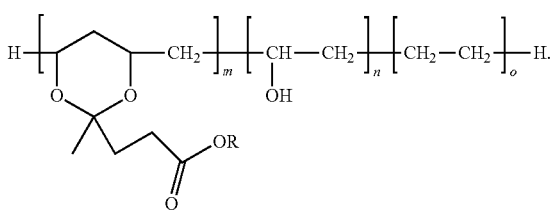

IIa
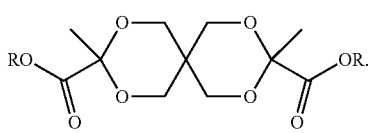

A variety of oxocarboxylates and polyols are incorporated, in various embodiments, into the compounds having structures I or II. Suitable examples of oxocarboxylates and polyols, while not limiting as to the scope of all suitable materials that are starting materials for the compounds having structures I and II, are set forth below.

"Keto acid" refers to an oxocarboxylate having at least one ketone moiety and one carboxylic acid moiety. A compound may have more than one ketone functionality or more than one carboxylic acid functionality. The keto acid is not particularly limited as to additional moieties or functionalities present in addition to the ketone and carboxylic acid functionalities. In some embodiments, the compound may also contain one or more halogen, ester, amine, thiol, ether, phosphate, or silane groups. Some examples of suitable keto acids include pyruvic acid, acetoacetic acid, levulinic acid, 5-aminolevulinic acid, oxaloacetic acid, α-ketobutyric acid, α-ketoglutaric acid, α-ketoisovaleric acid, 5-ketohexanoic acid, α-ketoisocaproic acid, α-ketoadipic acid, 3-ketoadipic acid, 2-keto-4-methylthiobutyric acid, 4-acetylbutyric acid, 2-keto-3-bromobutyric acid, phenylpyruvic acid, 2-keto-3-phenylpropanoic acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, 13-keto-9,11-octadecadienoic acid, 4-ketostearic acid, 9-ketopalmitic acid, 4-ketoheptanedioic acid, penicillic acid, 8-keto-8-aminopelargonic acid, 2-keto-5-aminovaleric acid, 2-succinylamino-6-oxoheptanedioic acid, 2-oxo-3-butynoate, 3-keto-6-acetamidohexanoate, and the like. Additionally, a keto acid may contain hydroxyl or mercapto functionality provided it is protected, e.g. by one or more trimethylsilyl or t-butyl groups, or one or more other protecting groups known to those of skill in the art.

In some embodiments of the invention, the keto acid employed is levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. In other embodiments, pyruvic acid and acetoacetic acid are other acids employed.

"Keto ester" refers to the carboxylic ester of the one or more carboxylate functionalities of any of the above described keto acid compounds. Thus, in embodiments where structure I is an ester, the $R_1$ group of structure I is not hydrogen. The $R_1$ group is, in embodiments, a linear, branched, or cyclic alkyl or alkenyl group having 1 to 18 carbon atoms, or an aryl or alkaryl group, wherein the alkyl, alkenyl, aryl, or alkaryl groups can have one or more additional functional groups that can include, for example, halogen, ester, amine, thiol, ether, or silane functionalities and are not particularly limited except that the one or more additional functional groups do not include hydroxyl or mercapto functionality. Thus, $R_1$ can be, in embodiments, methyl or ethyl; a linear or branched isomer of an alkyl group such as propyl, butyl, pentyl, hexyl, septyl, octyl, nonyl, decyl, undecyl, dodecyl, tetradecyl, cetyl, or stearyl; a cycloalkyl group such as cyclohexyl, cyclooctyl, norbornyl, and the like; an alkynyl group such as ethynyl, 3-methylpent-1-yn-3-yl, tetradec-9-yn-1-yl, and the like; an aryl and alkaryl group such as phenyl, benzyl, tolyl, xylyl, 5-phenylpent-1-yl, and the like; wherein the alkyl, alkenyl, alkynyl, aryl, or alkaryl may additionally have one or more functional groups, for example, 1,1,1-trichloro-2-methyl-2-propyl, 5-fluoro-1-pentyl, 5-amino-1-pentyl, 5-benzyloxy-1-pentyl, 5-methoxy-1-pentyl, 3-nitro-2-pentyl, 4-methylthio-1-butyl, 1-carboxyhex-6-yl, propionamid-2-yl, and the like. $R_1$ can also be a protecting group, such as trimethylsilyl, phosphonooxy, or a phosphatidyl group. The composition of the $R_1$ group is not particularly limited; however, if there are hydroxyl or thiol functionalities present on the R$_1$ group they should further be protected by a protecting group, such as trimethylsilyl, t-butyl, phosphonooxy, or another group generally known in the art to be a protecting group, to avoid side reactions of the free hydroxyl or thiol with a neighboring oxo group.

In some embodiments of the invention, esters of levulinic acid, pyruvic acid, or acetoacetic acid are employed as the keto esters in the polyols. For example, ethyl levulinate or n-butyl levulinate can be employed in some embodiments of the invention. Levulinic esters are based on levulinic acid, an abundant feedstock that is prepared on an industrial scale by acidic degradation of hexoses and hexose-containing polysaccharides such as cellulose, starch, sucrose, and the like.

"Semialdehyde" refers to an oxocarboxylate having at least one aldehyde functionality and one carboxylic acid functionality. A compound may have more than one aldehyde functionality or more than one carboxylic acid functionality. The semialdehyde is not particularly limited as to additional moieties or functionalities present in addition to the aldehyde and carboxylic acid functionalities. In some embodiments, the semialdehyde may also contain one or more halogen, ester, phosphate, amine, thiol, ether, or silane groups. Some examples of suitable semialdehydes include aspartic semialdehyde, 4-oxobutanoic acid, 5-oxopentanoic acid, 6-oxohexanoic acid, 7-oxoheptanoic acid, α-formylglycine, 3-oxo-2-(phosphonooxy)-propanoic acid (tartronic semialdehyde wherein the hydroxyl group is protected by phosphate), 3-oxopropanoic acid (malonic semialdehyde), 2-methyl-3-oxopropanoic acid (methylmalonic semialdehyde), succinic semialdehyde, adipic Semialdehyde, 5-glutamyl semialdehyde, allysine, 2-aminomuconic semialdehyde, 4-amino-5-oxopentanoic acid, N-acetylglutamic semialdehyde, 2-amino-3-(3-oxoprop-1-enyl)-but-2-enedioic acid, and N2-succinyl-L-glutamic-5-semialdehyde. Many other semialdehydes are available by carrying out ozonolysis of unsaturated fatty acid esters to form an aldehyde moiety at an unsaturated site, as described by Criegee, *Angew. Chem. Int. Ed.*, 1975, 87, 745.

"Semialdehyde ester" refers to the carboxylic ester of the one or more carboxylate functionalities of any of the above described semialdehyde compounds. The nature of the ester group is generally the same as those described above for the keto ester functionalities. The composition of the ester R$_1$ group, as shown in Reaction I, is not particularly limited; however, if there are hydroxyl or thiol functionalities present on the R$_1$ group they should further be protected by a protecting group, such as a trimethylsilyl group or another group generally known in the art to be a protecting group, to avoid side reactions of the free hydroxyl or thiol with a neighboring oxo group.

For purposes of the invention, the term "polyol" means any alcohol having two or more hydroxyl groups. However, suitable polyols for use in forming the ketal moieties of structures I and II are tetrols and higher polyols having at least two pairs of hydroxyl groups wherein at least two pairs of hydroxyls are situated on contiguous or semi-contiguous carbons atoms, and further wherein the first of the two pairs of hydroxyls is contiguous or semicontiguous with respect to the second of the two pairs of hydroxyls. Examples of suitable polyols include erythritol, threitol, pentaerythritol, diglycerol, xylitol, apiitol (2-hydroxymethyl erythritol), mannitol, sorbitol, maltitol, lactitol, dipentaerythritol, tripentaerythritol, and higher oligomers of pentaerythritol, raffinose, and stachyose; and poly(vinyl alcohol) and copolymers thereof, such as MOWITAL™ resin available from the Kuraray Company of Osaka, Japan; AQUASOL™ resin available from A. Schulman, Inc. of Akron, Ohio; or ELVANOL® resin available from the DuPont Company of Wilmington, Del.

In some embodiments, the polyol employed is erythritol. In other embodiments, the polyol employed is sorbitol. In other embodiments, the polyol employed is diglycerol (a tetrol that is a mixture of glycerol dimers). As used herein, erythritol and threitol, which are diastereomers, are used interchangeably in various embodiments of the reaction. Similarly, sorbitol and its stereoisomer mannitol are used interchangeably in various embodiments. Where no stereochemistry is indicated in a chemical structure, any stereoisomer may be employed in the embodiments of the invention.

Synthetic routes to form compounds based on the ketals or acetals of oxocarboxylates are described in U.S. Patent Application Nos. 60/935,884; 60/960,629; and 61/048,339, the entirety of which are incorporated herein by reference. While generally useful to form monoketals or acetals of oxocarboxylates with various alcohols, the methods disclosed in the incorporated applications do not directly address any of the compounds embodied in the present invention. Thus, the reactivity toward the ketalization reaction of more than one equivalent of an oxocarboxylate with a polyol such as a tetrol, pentol, hexyl, or higher polyol, wherein the hydroxyls are situated on contiguous or semicontiguous carbon atoms, is not addressed by the incorporated methodology.

However, we have found that employing the methodology of the incorporated patent application, with additional optimization of the ratio of reagents and amount of acid catalyst employed in the reactions, provides for high yield and fast reaction times in the formation of the compounds having structure I or II. This result is surprising, particularly in embodiments where contiguous pairs of hydroxyls are reacted to form contiguous ketals, e.g. where c=0 in structure I, or in the case of the spiro-type ketals of structure II. In such embodiments, the reactivity of the second, third, and additional molar equivalents of oxocarboxylate with the polyol would be expected to be lower than the reactivity of the first molar equivalent of oxocarboxylate toward the polyol due to steric bulk, restriction in degrees of freedom for remaining hydroxyl moieties, or a combination of these factors with other factors. However, we have found that, in embodiments, the reactivity of the second and subsequent molar equivalents of oxocarboxylate toward the polyol already having one or more ketal moieties is the same or, in other embodiments, even higher than, the reactivity of the first molar equivalent of oxocarboxylate toward ketalization. Thus, in some embodiments of the formation of the compounds having structures I and II, adducts having only one ketal moiety per molecule could not be isolated because the reaction proceeded to virtually 100% very quickly once the first ketal moiety was formed.

In one nonlimiting example, the reaction of erythritol, a tetrol, and about 5 to 6 moles of oxocarboxylate per mole of erythritol (e.g., about 2.5 to 3 equivalents of oxocarboxylate per each two equivalents of hydroxyl, or per equivalent of diol functionality) is catalyzed with about $1 \times 10^{-4}$ to $1 \times 10^{-6}$ molar equivalents of an acid catalyst per mole of diol functionality, to provide nearly 100% conversion to the corresponding bisketal. The species of acid catalyst employed is not particularly limited in the various embodiments of the invention; any of the catalysts set forth in the incorporated methodology may be employed in the method of making various polyketals of the current invention. In another example, where sorbitol, a hexyl, is employed, about 8 moles of oxocarboxylate per mole of sorbitol (e.g. about 2.7 moles of oxocarboxylate per mole of diol functionality) with about $1 \times 10^{-4}$ to $1 \times 10^{-6}$ molar equivalents of an acid catalyst per mole of diol functionality, are reacted to provide nearly 100% conversion to the corresponding trisketal.

The compounds having structures I and II are useful in many different applications. In various embodiments, compounds having structures I and II are plasticizers, tougheners, surfactants, barrier layer materials, interfacial modifiers, compatibilizers, solvents, coalescing solvents, or phase transfer materials in one or more formulations.

Plasticizers are chemical compounds added to a base composition comprising one or more polymers with the purpose of lowering the glass transition temperature of the polymer composition, thereby making the composition more flexible and amenable to processing, e.g., by melt extrusion or molding. Plasticizers are typically used at various effective concentrations that depend on the desired properties of the compounded polymer formulation. For example, in embodiments, plasticizers are used at concentrations between 1 and 80% by weight of the unplasticized polymer. It is understood that, depending on the polymer and the plasticizer used, plasticizers can also confer other changes in physical and mechanical properties of the compounded polymer, as well as changes in barrier properties of the compounded polymer in respect to its permeability for various gases, water, water vapor, or organic compounds. It is also understood that one or more different plasticizers can be used in various blends with additional compounds for the preparation of an extrudable or moldable polymer composition. Such additional compounds can include various inorganic and organic filler compounds, wood dust, reinforcing fibers, dyes, pigments, lubricants, anti-microbial or anti-fungal additives, thermal or UV stabilizers, and the like.

In some embodiments, plasticizers are mixed with a polymer at temperatures that are above or below the melting point of the polymer. In some embodiments, plasticizers can be introduced with a help of a solvent. Many variations of techniques for introducing plasticizer compounds to polymer compositions are known in the art.

In embodiments employing the compounds of structure I where $\alpha$ is 1, $R^8$ and $R^9$ are hydrogen, and $R^1$ is ethyl, butyl, or 2-ethylhexyl, the compounds are plasticizers for PVC or polystyrene. In other embodiments where $\alpha$ is 2, $R^8$ and $R^9$ are hydrogen, and $R^1$ is ethyl, butyl, or 2-ethylhexyl, the compounds having structure I are plasticizers for PVC. In PVC formulations, the compounds of structure I or II are incorporated, in embodiments, at levels of up to 40% to result in clear blends after thermal compounding. Even at the highest loadings, the plasticizers of structure I and II are substantially retained in PVC formulations when subjected to extraction in hexane, mineral oil, or soap solutions at room temperature; the amount retained is, in embodiments, the same as or better than conventional PVC plasticizers such as dioctyl phthalate.

In polystyrene, compounds having structure I or structure II are incorporated, in embodiments, at levels of up to about 60% by weight of total formulation with excellent compatibility, resulting in a polystyrene formulation that is transparent and elastomeric, with a glass transition temperature of less than −40° C., and does not phase separate. Such a result is surprising, because in some embodiments the compounds of the invention are relatively polar compared to polystyrene; in some embodiments, the compounds of the invention are absent of aromatic content. Such compounds would not be expected to be miscible with polystyrene, particularly at the very high levels of incorporation observed.

Other polymers that are, in embodiments, plasticized by one or more compounds of the invention include, for example, homopolymers and copolymers of polystyrene, poly(3-hydroxyalkanoates), poly(lactate), and various polysaccharide polymers, as well as polyesters described herein below and those described in U.S. patent application Ser. No. 11/915,549 which is incorporated herein by reference in its entirety.

In other embodiments, the compounds having structures I and II are surfactants, interfacial modifiers, or phase transfer materials. In such embodiments, solubility and performance of the particular structure will depend on the media in which the compound is used. For example, in embodiments where $R^1$ is a metal cation or an organic cation, compounds having structures I and II are surfactants in certain applications. In other embodiments where $R^1$ is a poly(ethylene oxide) residue, compounds having structures I and II are surfactants when incorporated into one or more formulations. The hydrophilic-lipophilic balance (HLB) of the surfactant is easily tailored for any number of applications by changing the nature of the cation and other structural aspects of the various R groups. Depending on the structure of the various other R groups of structures I and II, for example, the compounds are, in embodiments, water soluble; in other embodiments the compounds are water insoluble. For example, in embodiments where one or more $R^2$, $R^3$, $R^4$, $R^5$, $R^6$, $R^8$, or $R^9$ groups, as applicable, are hydrocarbon moieties having at least about 4 carbon atoms, the HLB character of structures I and II is increased and in some embodiments the compounds are not water soluble.

For example, in some embodiments of the invention, compounds having structures I and II are powerful solvents that are capable of removing tenacious surface coatings. For example, coatings such as dried and cured paint, adhesives, and the like are removed by compounds having structures I and II. Thus, in embodiments, the compounds having structures I and II are useful for cleaning applications, removal of paint such as graffiti paint, and other similar applications.

Similarly, by varying the nature of the various R groups of structures I and II, the compounds are, in various embodiments, phase transfer materials, coalescing solvents, compatibilizing solvents, or interfacial modification materials. In some such embodiments, $R^1$ is a cation; in other embodiments $R^1$ is not a cation. For example, in some embodiments, the compounds having structures I and II are able to make otherwise immiscible solvents miscible. In one such embodiment, a compound of structure I wherein $R_1$ is ethyl, $R_2$, $R_3$, $R_8$, and $R_9$ are hydrogen, $R_4$ is methyl, a is 2, b and c are 0, and $\alpha$ is 1, the compound is capable of making a mixture of methanol and hexane miscible. Miscibility of the two otherwise immiscible solvents is observed from vol/vol ratios of about 5 vol % to 95 vol % methanol, or about 40 vol % to 60 vol % methanol, or about 50 vol % methanol. The same compound, surprisingly, is also useful to make blends of water and methanol miscible. Miscibility of the otherwise immiscible set of solvents is observed from vol/vol ratios of about 5 vol % to 95 vol % methanol, or about 40 vol % to 60 vol % methanol, or about 50% methanol, when the compound of structure I wherein $R_1$ is ethyl, $R_2$, $R_3$, $R_8$, and $R_9$ are hydrogen, $R_4$ is methyl, a is 2, b and c are 0, and a is 1 is incorporated. Similar results are seen in embodiments where $\alpha$ is increased from 1 to 2. Miscibility of the solvents is gained with an addition of about 0.01 vol % to 50 vol % of the compound of structure I based on the total volume of the combined solvents, or about 0.1 vol % to 20 vol %, or about 1 vol % to 10 vol % of the compound of structure I.

Various other embodiments, the compounds having structures I and II are similarly useful in imparting miscibility to otherwise immiscible solvent sets. What is particularly surprising about the compounds of structures I and II is that they are capable of imparting miscibility to a wide range of solvents, e.g. from very nonpolar solvents, such as hexane, with very polar solvents, such as methanol; to mixtures of polar solvents such as methanol and water.

Due to the relatively high molecular weight and relatively low vapor pressures of some compounds having structures I and II, when compared to many commonly employed solvents such as lower alkyls having six or less carbon atoms, lower alcohols having six or less carbon atoms, water, ketones such as acetone and methyl ethyl ketone, acetates such as ethyl acetate, and the like, one or more compounds of the invention are advantageously employed in one or more embodiments as coalescing solvents. Coalescing solvents are those used to form a single phase during the drying and curing of a coating formulation, thus they must have lower vapor pressure than the "main" solvent but must provide for a miscible blend with the coating materials in the absence of the main solvent. Latex paints, for example, cure by the process of coalescence, where first the water, and then the trace, or coalescing, solvent, evaporate and draw together and soften the latex binder particles and fuse them together into irreversibly bound networked structures, so that the paint will not redissolve in the solvent/water that originally carried it. The coalescing solvent must be miscible with the "main" solvent—in the case of a latex, water—in order for it to work effectively. Again, the surprising miscibility of some compounds having structures I and II with other solvents—and even their ability, in embodiments, to impart miscibility to otherwise immiscible solvent blends, makes them excellent coalescing solvents for a number of different formulations.

For example, in some embodiments, the presence of about 0.5 wt % to 25 wt % of one or more compounds of the invention are mixed with various latexes having water as the main solvent. Upon drying coatings of such latexes, in embodiments, a continuous film forms. This is true even under conditions in which, for example, discontinuous films are observed to form when the one or more compounds of the invention are not added to the latex prior to coating and drying. In other embodiments, about 1 wt % to 10 wt % of one or more compounds of the invention is added to various latexes to form a continuous film upon drying of the latex. In still other embodiments, about 5 wt % is added to a latex to form a continuous film upon drying of the latex. No special mixing is required, in various embodiments, to incorporate the one or more compounds of the invention into latexes as coalescing solvents; no instabilities are observed when the one or more compounds of the invention are added and mixed into various latexes.

In some embodiments, the value of $\alpha$ is substantially greater than 2, for example in some embodiments $\alpha$ is between about 10 and 100. In other embodiments, $\alpha$ is between about 100 and 250. Such embodiments impart, in embodiments, interfacial modification or phase transfer properties to the compounds of structures I and II. In other embodiments where $\alpha$ is substantially greater than 2, the compounds of structure I provide barrier layer properties to films wherein the compounds are incorporated. In such embodiments, the compounds of structure I result in enhanced processability and physical properties, such as thermal stability, compared to conventional poly(vinyl alcohol) barrier films but retain the desirable aspects of barrier layers incorporating poly(vinyl alcohol), namely, oxygen diffusion barrier properties.

In some embodiments, the reaction of an oxocarboxylic acid or ester thereof with a tetrol or higher polyol to result in structures I and II is limited by compatibility of the two chemical species; that is, the oxocarboxylic acid or ester thereof is immiscible with the tetrol or higher polyol. In such embodiments, a solvent may be used to provide solubility of both materials, thereby increasing miscibility. Solvents that may be used in such reactions include aromatic solvents such as toluene, benzene, and the like; ethers such as diethyl ether or tetrahydrofuran; dimethyl formamide; dimethyl sulfoxide; hydrocarbons such as hexane, pentane, and the like; or any other solvent found to be useful in providing miscibility without reacting with one or both reagents or with the acid catalysts typically employed in the ketal formation reaction. In other embodiments where miscibility is a limiting factor in the reaction, incorporating some amount of a surfactant provides miscibility. Surfactants that can be employed in the reaction include any conventional surfactant that is not reactive with the reagents and is not reactive in the presence of the acid catalysts typically employed in the ketal formation reaction. For example, nonionic surfactants such as polyethylene glycol-propylene glycol block copolymers with alkyl endgroups, are useful in such reactions and are not reactive with any of the reagents employed in the ketalization reaction.

In other embodiments where miscibility is a limiting factor in the reaction, incorporating some amount of the product ketal provides miscibility. For example, in a reaction vessel with an oxocarboxylate and a tetrol or higher polyol that are not miscible, adding 5% or more by weight of the corresponding ketal adduct, based on the weight of oxocarboxylate and polyol, to the flask results, in embodiments, in a homogeneous mixture. In some embodiments, 10% by weight of the corresponding ketal adduct, based on the weight of oxocarboxylate and polyol, is required in order to form a homogenous mixture. In other embodiments, more than 10% by weight of the corresponding ketal adduct, based on the weight of oxocarboxylate and polyol, is required in order to form a homogenous mixture.

In still other embodiments where miscibility of the reagents is a limiting factor in the reaction, transesterification is employed after ketalization to provide compounds of interest that are not easily reacted in the ketalization reaction. For example, octadecyl pyruvate and erythritol are not, in certain embodiments, miscible without a solvent or surfactant. However, methyl pyruvate, ethyl pyruvate, or the like may be reacted with erythritol to form the product bisketal having two methyl ester or ethyl ester moieties, followed by transesterification with octadecyl alcohol to form the octadecyl ester of the bisketal.

Esterification or transesterification of various polyketal structures of the invention is also usefully employed to impart functional groups to the polyketals. In certain particularly useful embodiments contemplated by structures I and II, one or more $R^1$ moieties include one or more hydroxyl functionalities capable of reacting with one or more electrophiles. Such structures are obtained, in embodiments, by reacting the carboxylic acid or ester functionalities of structure I or II with a second polyol, which is a diol, triol, or higher polyol that may be the same or different from the first polyol, the first polyol being the tetrol or higher polyol used to form the polyketals of structures I and II. Thus, the polyketals of structures I and II are converted to polyketal polyols.

The formation of such polyketal polyols are carried out, in embodiments, using conventional techniques of esterification or transesterification to functionalize the compounds of structure I and II. Conventional techniques include, in some embodiments, addition of heat and/or catalyst(s) to a mixture of a polyketal of structures I or II with a second polyol. Alternatively, esterification or transesterification of an oxocarboxylate may be carried out, in some embodiments, prior to ketalization with a tetrol or higher polyol to yield a polyketal polyol of structure I or II. Such embodiments are employed where the esterification or transesterification is accomplished using a polyol that is incapable of forming substantial amounts of cyclic ketal reaction products. For example, 1,6 hexanediol or diethylene glycol do not readily form a cyclic ketals; so they are more readily available for an esterification or transesterification reaction with an oxocarboxylate.

In some embodiments, polyketal polyols of the invention are the products of esterification of the carboxyl moieties present on a polyketal of structures I and II with a second polyol that is a diol or higher polyol. The second polyol may be the same as the first polyol, which is the polyol used in a ketalization reaction to form the polyketal of structures I and II, or it may be a different polyol. The polyketal polyol has at least two hydroxyl functionalities present on the $R_1$ groups of structures I and II.

Suitable second polyols, that is, diols and higher polyols used in the esterification or transesterification reactions of the polyketals of structure I or II to result in polyketal polyols, include the tetrols and higher polyols described above. Additional useful polyols include diols, for example, 1,2-ethanediol (ethylene glycol), 1,2-propanediol (propylene glycol), 1,3-propanediol, 2,2-dimethyl-1,3-propanediol (neopentyl glycol), 2-butyl-2-ethyl-1,3-propanediol, 3-mercaptopropane-1,2-diol (thioglycerol), dithiothreitol, 1,2-butanediol, 1,3-butanediol, 1,4-butanediol, 2,3-butanediol, 1,5-pentanediol, 3-methyl-1,5-pentanediol, 1,6-hexanediol, 2-ethyl-1,3-hexanediol, cyclohexane-1,2-diol, cyclohexane-1,4-diol, 1,4-dimethylolcyclohexane, 1,4-dioxane-2,3-diol, 3-butene-1,2-diol, 4-butenediol, 2,3-dibromobutene-1,4-diol, 1,8-octanediol, 1,10-decanediol, 1,12-dodecanediol, benzene-1,2-diol (catechol), 3-chlorocatechol, indane-1,2-diol, tartaric acid, and 2,3-dihydroxyisovaleric acid, diethylene glycol (DEG), triethylene glycol, tetraethylene glycol, dipropylene glycol, tripropylene glycol, tetrapropylene glycol, xylene glycol, 1,3-benzenediol (resorcinol), 1,4-benzenediol (hydroquinone), o, m, or p-benzene dimethanol, o, m, or p-glycol phthalates, o, m, or p-bis-1,2-ethylene glycol phthalates, o, m, or p-bis-1,2-propylene glycol phthalates, o, m, or p-bis-1,3-propylene glycol phthalates, diols prepared by hydrogenation of dimer fatty acids, hydrogenated bisphenol A, hydrogenated bisphenol F, propoxylated bisphenol A, isosorbide, 2-butyne-1,4-diol, 3-hexyne-3,5-diol (SURFYNOL® 82, available from Air Products of Allentown, Pa.) and other alkyne-based polyol products marketed under the SURFYNOL® brand name by Air Products of Allentown, Pa.; and also include triols, for example, 1,2,3-propanetriol (glycerol), 1,1,1-trimethylolpropane, 1,1,1-trimethylolethane, pentaerythritol, 1,2,3-butanetriol, 1,3,4-butanetriol, 1,2,4-butanetriol, 1,2,3-heptanetriol, 4-menthane-1,7,8-triol, 1,2,5-trihydroxy pentane, 1,2,6-trihydroxyhexane, 1,2,7-trihydroxyheptane, 1,2,3-trihydroxyoctane, 1,2,3-trihydroxynonane, 1,2,4-trihydroxynonane, 1,2,3-trihydroxyundecane, 1,2,3-trihydroxydodecane, 1,2,11-trihydroxyundecane, 1,2,12-trihydroxydodecane, and the like.

The group of suitable second polyols also includes tetrols that do not have at least two pairs of hydroxyls that are contiguous or semicontiguous, such as dipentaerythritol and pentaerythritol derivatives and other polyhydric alcohol derivatives such those sold under the trade name CHARMOR® by Perstorp Polyols, Inc. of Toledo, Ohio; and other polyols and polymeric polyols bearing hydroxyl groups that are not contiguous or semi-contiguous, such as polyether polyols based on ethylene glycol, for example CARBOWAX® polyethylene glycols (available from Dow® Company of Midland, Mich.), polyether diols and polyols based on propylene glycol or combinations of ethylene glycol and propylene glycol, such as those sold by the Dow® Company of Midland, Mich., and polyether glycols such as those produced by the INVISTAT™ Company of Wichita, Kans. under the trade name TERETHANE®; dendritic polyols, for example those sold under the trade name BOLTORN® by Perstorp Polyols, Inc. of Toledo, Ohio; polycarbonatediols of varying molecular weights, such as L467m, L600m, and L565m, available from Asahi Kasei Corporation (Tokyo, Japan); polyols based on hydroxylated vegetable oils, such as those sold under the trade name BiOH®, available from the Cargill Company of Wayzata, Minn.; hydroxyl-terminated polybutadienes, such as HTPB R45M, sold by Aerocon Systems of San Jose, Calif., polyols produced by the Everchem Company of Media, Pa., or Maskimi Polyol Sdn. Bhd. of Kajang, Selango Darul Ehsan, Malaysia, and the polyols employed in the Union Carbide Company (South Charleston, W. Va.) publication by Carey et al., "Rapid Method for Measuring the Hydroxyl Content of Polyurethane Polyols" (published on the internet at http://www.polyurethane.org/s_api/doc_paper.asp?CID=1044&DID=4060).

Various polyketal polyols of the invention are, in embodiments, useful in many of the applications described above. For example, compounds having structure I or II wherein $R^1$ is $HO-(CH_2-CH_2-O-)_x$, are, in various embodiments, plasticizers, nonionic surfactants, interfacial modifiers, or phase transfer materials.

In other embodiments, polyketal polyols having structures I or II are employed as polyols in subsequent syntheses. For example, where structure I is a polyketal polyol, self condensation of structure I is carried out in embodiments to form dimers, oligomers, and polymers. Similar condensation reactions are contemplated employing one or more additional diols or higher polyols and one or more diacids or diester compounds. Alternatively, the polyketal polyols react, in embodiments, with compounds such as diisocyanates, alkyl carbonates, lactones, acrylates, methacrylates, glycidyl or other epoxy functional compounds, or allyl compounds. Such reactions result in various polymer precursors which usefully participate in further reactions to form, in various embodiments, dimers, oligomers, polymers, and crosslinked networks.

In various embodiments, compounds having structure I or II are subjected to subsequent reactions that result in dimeric, oligomeric, or polymeric compounds having structures III and IV, respectively:

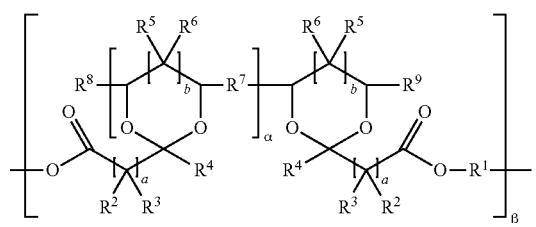

III wherein $R^1$, $R^2$, $R^3$, $R^4$, $R^5$, $R^6$, $R^7$, $R^8$, a, b, and a of structure III are the same as those as defined for structure I, and β is an integer of at least 2;

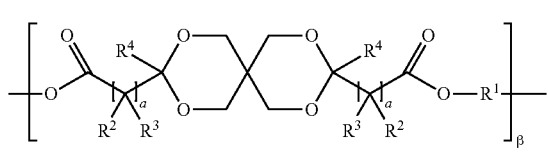

IV wherein $R^1$, $R^2$, $R^3$, $R^4$, a, and α are as defined for structure II and β is an integer of at least 2.

Additional embodiments of structures I, II, III, and IV are discussed in Sections A-H, below.

A. Dimerization and Oligomerization Polyketals and Polyketal Polyols

The polyketal polyols having structures III and IV are, in embodiments, dimers or oligomers. A dimer is represented by either structure III or IV where the value of is 2; an oligomer is represented by values of β of about 3 to 12. By adjusting and optimizing reaction conditions, it is possible, in embodiments, to foam a high percent of dimer. In some embodiments, the polyketals having structure I can be dimerized or oligomerized by employing a second polyol of structure III wherein β is between 2 and about 12. In such embodiments, the techniques employed to make such polyols are similar to those employed to make the polyketal polyols as described above. In some such embodiments, a stoichiometric balance of a compound having structure I and a second polyol is suitable to form a dimer or oligomer of structure III instead of a monomeric polyketal polyol. Structure IV similarly arises from structure II.

One example of a dimerization reaction is shown in FIG. 1A. In one embodiment, dropwise addition of diol into a reaction flask of bisketal ester results in formation of a significant yield of dimer corresponding to one diol group with two bisketal groups. Other methods to obtain dimers where higher oligomers are not desirable are readily envisioned.

Oligomers of polyketals and polyketal polyols, for example those having a degree of polymerization (β) of about 2 to 12, are readily obtained by adjusting reaction conditions to optimize the formation of repeat unit structures. For example, in the reaction of a diol with a bisketal ester, providing a 1:1 stoichiometry and adjusting the time and temperature of the reaction accordingly results, in embodiments, in a mixture of oligomeric poly(bisketal)s.

In some embodiments, esterification or transesterification of polyketal acids or esters to give polyols is carried out by employing a catalyst. The catalyst may be any of the known esterification or transesterification catalysts in general. For example, acidic catalysts such as a toluenesulfonic acid, sulfuric acid, sulfamic acid, or a sulfonic acid are employed in various embodiments. In other embodiments an organometallic catalyst is employed, for example a catalyst based on titanium or tin, such as titanium tetrabutoxide (Ti(OBu)$_4$), or tin (II) octanoate. The choice of catalyst is not particularly limited within the scope of the invention.

In various embodiments, the dimers and oligomers of the compounds having structures I and II are useful in the same applications as those described above. Thus, in various embodiments, dimers and oligomers of compounds having structures I or II are plasticizers, surfactants, phase transfer materials, interfacial modifiers, and the like.

The compounds having structures III and IV are also capable of further reaction in embodiments where one or more residual hydroxyl, ester, or acid functionalities reside within the $R^1$ functionality. Thus, where reactions in sections B to H employ "monomeric", e.g. non-dimerized or non-oligomerized, species of structures I and II, dimers, oligomers, and polymers thereof having structures III and IV are also suitably employed in various embodiments due to their reactivity in the systems as described.

B. Polyketal Polyesters

The polyketals having structures I and II are, in embodiments of the invention, polymerized via esterification or transesterification. By forming a polyketal polyol, or by reacting a polyketal that is not a polyol with one or more diols or higher polyols, transesterification can lead to dimers or oligomers, as is described below, and also to polymers. Bisketal esters, that is esters having structure II or esters having structure I wherein a is 1, react with diols to form linear oligomers and polymers. Trisketals and higher polyketals, that is polyketals of structure I wherein α is 2, as well as triols and higher polyols, can also be employed to form the corresponding branched, hyperbranched, dendritic, or crosslinked network polymer. Importantly, mixtures of e.g. bisketals and a minor amount of trisketal or a higher polyketal, or mixtures of diols and a minor amount of triols or higher polyols, can be advantageously employed to give variable degrees of branching and/or crosslinking.

Figure 1B:
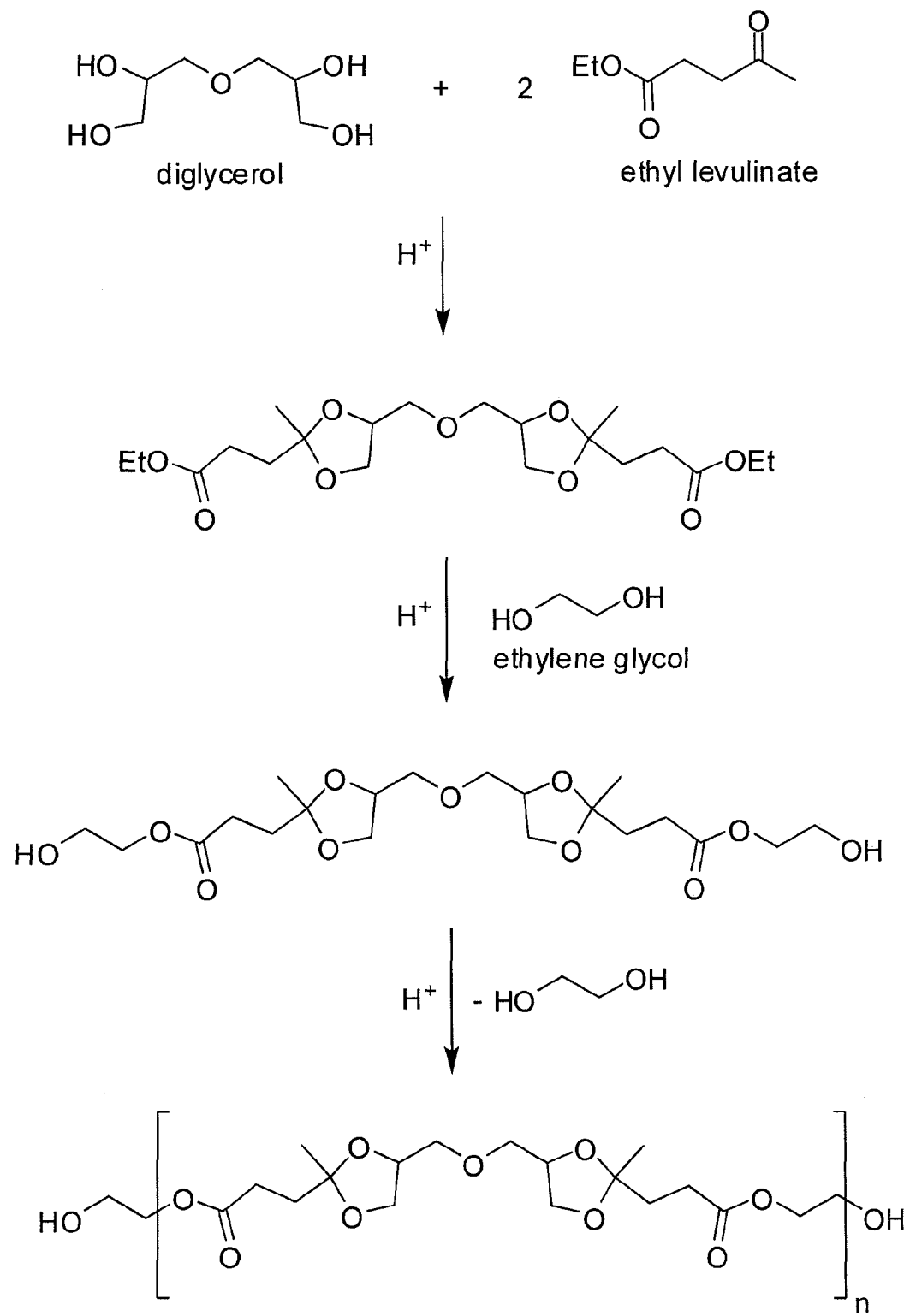

The polyketal polyesters of the invention are represented by the compounds having structures III and IV, wherein the values of are more than about 12. In some embodiments the value of β is between about 12 and 100; in other embodiments the value of β is about 100 to 500; in still other embodiments the value of β is as high as about 1000. In embodiments, the value of α in structure III is 1. A representative example of polyester synthesis via self-condensation of a bisketal diol is shown in FIG. 1B.

The polyketal polyesters of the invention are, in embodiments, synthesized using conventional transesterification polymerization catalysts and conditions. For example, without limiting the catalyst species employed, any of the catalysts described in section A. above are suitable catalysts for the reaction to form various polyketal polyesters of the invention. In embodiments, reaction conditions and reagents are optimized to reach high molecular weight, maximize crystalline content, provide transparent, colorless films, or provide other properties idea for one or more other applications.

The polyesters of the invention have, in embodiments, excellent thermal stability and have superior tensile properties. In some embodiments, the polyesters of the invention are stable in air at temperatures of up to 250° C. In other embodiments, the polyesters of the invention are stable in air at temperatures up to about 300° C. In still other embodiments, the polyesters of the invention are stable in air at temperatures of over 300° C.

C. Polyketal Copolyesters

Figure 1C:
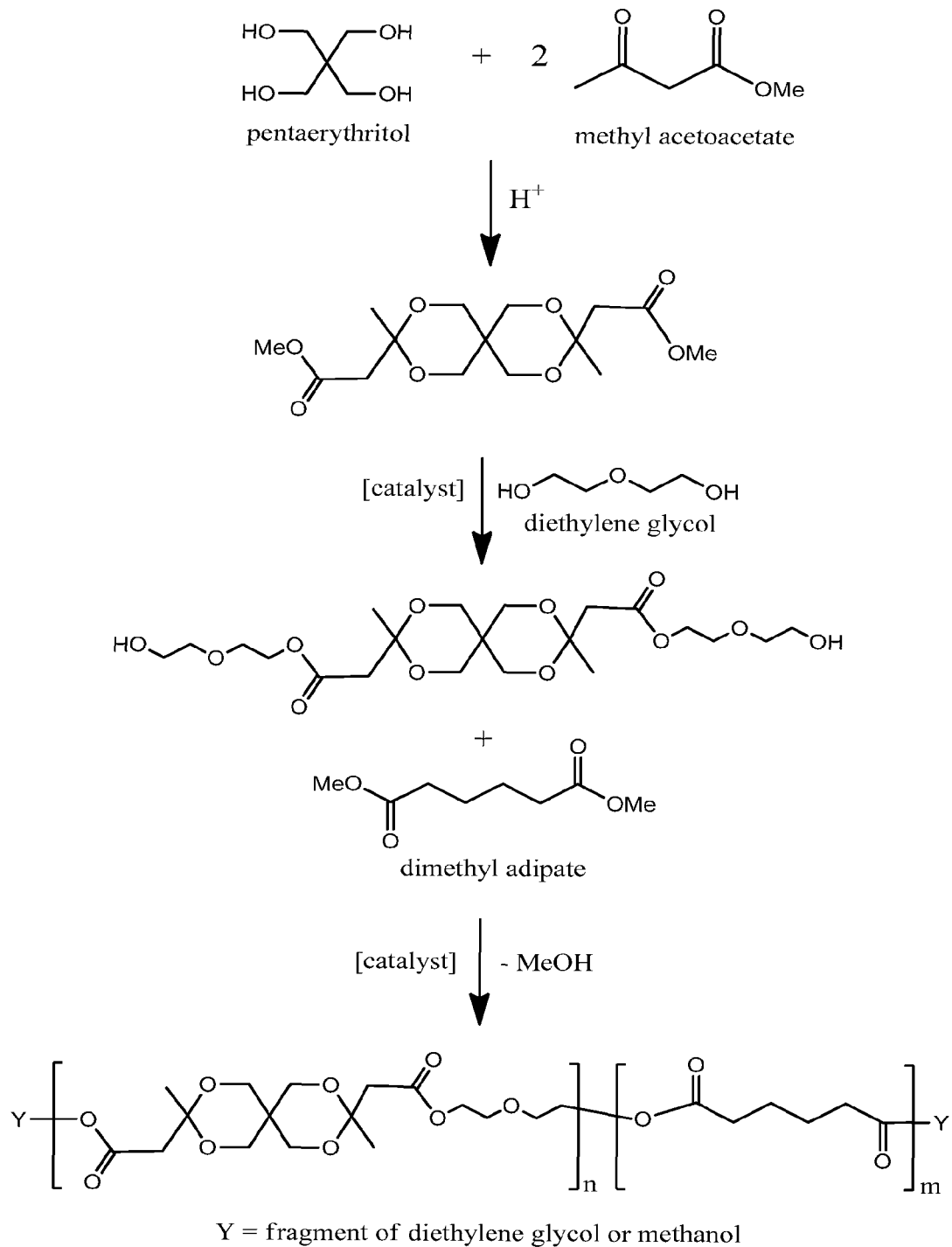

Polyester copolymers are formed, in embodiments, by reacting a polyketal acid or ester, a polyketal polyol or a dimer or oligomer thereof, with one or more additional diacids or diesters, diols, or a mixture thereof to give the corresponding copolyester. For example, a bisketal polyol can be polymerized with, for example, adipic acid or methyl isophthalate, to give the corresponding copolyester. A representative example of such a copolymerization is shown in FIG. 1C. Any of the diols listed in previous sections are suitable for use in a copolymerization reaction to provide polyketal copolyesters.

The polyketal copolyesters of the invention are represented by the compounds having structures III and IV, wherein the value of β is 1 or greater; that is, there is at least one repeat unit of structure III or IV in the copolymer. In some embodiments the value of β is between about 2 and 100; in other embodiments the value of β is about 100 to 500. In embodiments, the value of α in structure III is 1; in other embodiments the value of α is 2. In still other embodiments, a mixture of compounds of structure III, wherein a mixture of α values are used; for example, a mixture of compounds wherein α is 1 is employed, in embodiments, with a minor amount of a compound of structure III wherein the value of α is 2 to impart some degree of branching or crosslinking. Many related variations are readily envisioned.

Non-limiting examples of suitable diacids (or esters of diacids) suitable for use in synthesizing the polyketal copolyesters of the invention include aliphatic, cycloaliphatic or aromatic dicarboxylic acids, for example, succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, or hydrogenated dimerized fatty acids. The methyl, ethyl, propyl, butyl or phenyl esters of the acids listed above are suitable substitutes for the diacid component, as well as acid anhydrides (such as o-phthalic, maleic or succinic acid anhydride or a mixture thereof.

In embodiments, the copolyesters of the invention are synthesized using conventional transesterification polymerization catalysts and conditions. For example, without limiting the catalyst species employed, any of the catalysts described in section A. above are suitable catalysts for the reaction to form various polyketal copolyesters of the invention. In embodiments, reaction conditions are optimized to reach high molecular weight. Such reaction conditions include, in embodiments, the techniques, conditions, and catalysts employed in polyesterification reactions described in U.S. patent application Ser. No. 11/915,549, the entirety of which is incorporated herein by reference.

Crosslinked or branched analogs of various polyketal copolyesters of the invention are readily formed by employing a major proportion of diacids or esters thereof, and bisketal acids or esters thereof, with a minor proportion of, in embodiments, trisketal or higher acid or ester thereof, or tricarboxylic acid or higher polyacid or ester thereof. It will be easily understood that trisketals and higher polyketals, as well as triols and higher polyols and triacids and higher polyacids, can be employed to form the corresponding crosslinked polymer or branched polymer. Importantly, mixtures of e.g. bisketals and a minor amount of trisketal or a higher polyketal; or mixtures of diols and a minor amount of triols or higher polyols; or mixtures of diacids and a minor amount of a triacid or higher polyacid; or a combination of any of these can be advantageously employed to give variable degrees of branching and/or crosslinking. Some examples of suitable triacids include 1,3,5-trimethylcyclohexane-1,3,5-tricarboxylic acid, cis or trans aconitic acid, propane-1,2,3-tricarboxylic acid, hemmellitic acid, isocitric acid, and the like.

In other embodiments, polyketal polyols or dimers or oligomers thereof are employed in the ring opening reaction of one or more lactones to form the corresponding copolyester. Ring opening polymerization of lactones is carried out using one or more catalysts and using reaction conditions suitable for ring opening polymerization. Catalysts and reaction conditions employed in such reactions are any of those used in the art for ring opening reactions of lactones. For example, some ring opening polymerization catalysts are based on transition metals such as zinc, tin, or titanium. Without limiting the species of catalysts or reaction conditions employed, any of the catalysts or reaction conditions described in Hori et al., U.S. Pat. No. 5,516,883 or Schechtman et al., U.S. Pat. No. 5,648,452 are useful. Activated carbon as employed by Endo et al., EP1857484 or organic catalysts employed as described in a web-published article from IBM Company of Armonk, N.Y., at www.almaden.ibm.com/st/chemistry/ps/catalysts/RingOpening/ may be used to affect the ring opening polymerization of lactones using the polyketal polyols of the invention as the initiating polyol. The above examples are not limiting as to the type of catalyst or set of reaction conditions that can be employed in a ring opening polymerization of lactones.

Suitable lactones for the ring opening polymerization initiated by one or more polyketal polyols of the invention include, without limitation, propiolactone, pivalolactone, diketene, dimethyldiketene, β-butyrolactone, 4-butyrolactone, 4-valerolactone, δ-caprolactone, ε-caprolactone, 5-ethenyl-5-methyloxolan-2-one, gluconolactone, glucuronolactone, D-galactonolactone, coumarin, hydrocoumarin, ascorbic acid lactone, α-angelicalactone, 2-acetylbutyrolactone, 6-propyloxan-2-one, 6-ethyloxan-2-one, ribonolactone, arabonolactone, λ-nonalactone, bicyclononalactone, 5-nonalactone, λ-decalactone, pantolactone, 2-dehydropantolactone, 5-butoxolan-2-one, isocrotonolactone, 6-hexyloxan-2-one 5-heptyloxolan-2-one, 5-propyloxolan-2-one, 6-[(E)-pent-2-enyl]oxan-2-one, cocolactone, isocitric lactone, 2-hydroxy-6-methylpyran-4-one, 1-oxacyclododecan-2-one, ε-dodecalactone, 1-oxacyclopentadecan-2-one, 1-oxacycloheptadecan-2-one, L-arabino-1,4-lactone, 4-hydroxy-4-methyloxan-2-one, homoserine lactone, 4-methyl-7-propan-2-yloxepan-2-one, and the like.

In one embodiment of a lactone ring opening polymerization, one or more polyketal polyols of the invention are employed in the ring opening polymerization of SEGETOLIDE™ (available from Segetis, Inc. of Golden Valley, Minn.) or its dimer to form the corresponding levulinate-glycerol ketal polyester. The structure of SEGETOLIDE™ and its dimer, as well as methods for the ring opening polymerization of both compounds, are found in U.S. patent application Ser. No. 11/915,549, the contents of which are incorporated by reference herein in their entirety. The methods disclosed therein are suitable, in embodiments, for initiating the ring opening polymerization using the polyketal polyols of the invention as initiators.

The techniques used to synthesize one or more copolyesters of the invention are, in embodiments, the same as the techniques employed to synthesize homopolyesters as described in section B. Applications for copolyesters of the invention are similar, in embodiments, to those for homopolymers, except that a broader range of physical properties is available by the use of comonomers. For example, the incorporation of terephthalate as a diester in the copolymerization reaction leads, in embodiments, to increased crystalline content, which in turn increases the utility of the copolymer for applications for which polyesters are commonly known in the literature.

The thermal and environmental stability of one or more copolymers of the invention, insofar as they relate to the polyketal repeat units present in one or more embodiments, is excellent. As with one or more polyesters of the polyketals of the invention formed by their condensation with polyols, the copolyesters based on one or more polyketals of the invention are, in some embodiments, stable in air up to 250° C. In other embodiments, the copolyesters of the invention are stable in air up to 300° C. In yet other embodiments, the copolyesters of the invention are stable in air at temperatures in excess of 300° C. The copolyesters of the invention also have, in embodiments, excellent tensile properties that make them useful for a wide variety of commercial applications.

D. Polyketal Polyisocyanates

Polyketal polyols of structures I, II, III, and IV are employed, in embodiments, in the formation of polyketal polyisocyanates. The polyketal polyols that are the precursors to polyketal polyisocyanates are any of the polyketal polyols described above; thus, a polyketal polyol corresponding to structure I or II, may be employed; similarly, an oligomer or polymer of structure III or IV may be employed as starting materials for one or more polyketal polyisocyanates of the invention. In some embodiments employing structures I or III, the value of $\alpha$ is 1; in other such embodiments the value of $\alpha$ is 2. In yet other such embodiments, the value of $\alpha$ is as high as 100. When employing structures III or IV, the value of $\beta$ is between about 2 and 12; in other such embodiments the value of $\beta$ is up to about 100.

In such embodiments, at least one $R^1$ in any of structures I, II, III, or IV contains one or more hydroxyl moieties that are capable of reacting with a diisocyanate or higher polyisocyanate to form a polyketal polyisocyanate by forming a urethane linkage. Suitable diisocyanates useful in forming one or more polyketal polyisocyanates of the invention include, without limitation, those represented by formula OCN—Z—NCO, in which Z represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms, or a divalent aromatic hydrocarbon group having 6 to 15 carbon atoms.

Non-limiting examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or TDI), bis-(4-isocyanatocyclohexyl)methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, 1,5-diisocyanato naphthalene; and mixtures thereof.

Also suitable for making one or more polyketal polyisocyanates of the invention are polyisocyanates containing 3 or more isocyanate groups. Nonlimiting examples of suitable polyisocyanates include 4-isocyanatomethyl-1,8-octamethylene diisocyanate, aromatic polyisocyanates such as 4,4',4"-triphenylmethane diisocyanate, and polyphenyl polymethylene polyisocyanates obtained by phosgenating aniline/formaldehyde condensates.

One or more polyketal polyisocyanates of the invention are synthesized, in some embodiments, in the form of a polyketal polyisocyanate adduct. Suitable polyketal polyisocyanate adducts are those containing isocyanurate, uretdione, biuret, urethane, allophanate, carbodiimide and/or oxadiazinetrione groups.

In some embodiments, diisocyanates employed to make one or more polyketal polyisocyanates of the invention include the various isomers of diphenylmethane diisocyanate and mixtures thereof, IPDI, 4,4'-dicyclohexyl-methane diisocyanate, and polymeric isocyanates based on diphenylmethane diisocyanate, such as Mondur™ MRS (available from Bayer MaterialScience LLC of Pittsburgh, Pa.).

Figure 1D:
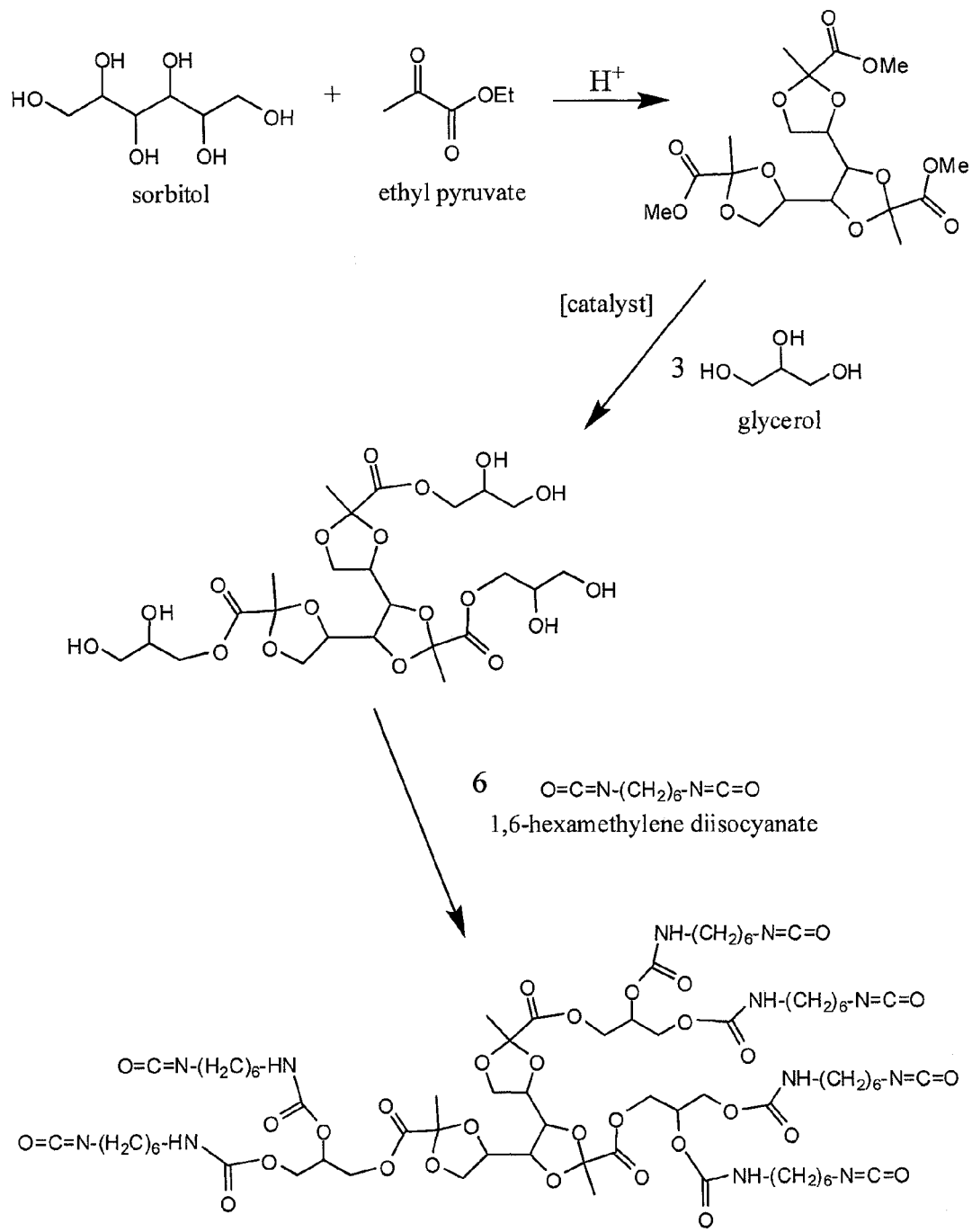

A representative synthetic scheme for one embodiment of a polyketal polyisocyanate of the invention is shown in FIG. 1D.

Methods used to make one or more polyketal polyisocyanates of the invention include conventional techniques known in the literature for the synthesis of polyisocyanates from polyols and diisocyanates. A representative technique for making one or more polyketal polyisocyanates of the invention is that employed in U.S. patent application Ser. No. 11/915,549, which is incorporated herein by reference in its entirety. The technique of the incorporated Application employs an excess of diisocyanate, as determined by hydroxyl equivalents per mole of polyol, in the presence of dibutyltin dilaurate to give the corresponding polyisocyanate.

One or more polyisocyanates of the invention are useful, in embodiments, for the subsequent synthesis of polyurethanes, polyureas, and poly(urethane ureas), and other related structures as outlined in section E. below.

E. Polyketal Polyurethanes, Polyketal Poly(urethane urea)s, Poly(ester urethane)s, and Poly(ester urethane urea)s The various polyketal polyols and polyketal polyisocyanate structures of the invention described in any of the embodiments above are employed, in embodiments, in the synthesis of polyketal polyurethanes, polyketal poly(urethane urea)s, and related structures. Polyketal polyols as described above are reacted, in some embodiments, with polyisocyanates that are any one of, or a blend of, the polyisocyanates listed in section D. above. Whereas a stoichiometric excess of polyisocyanate relative to the polyol results in a polyisocyanate as described in section D., a 1:1 stoichiometric ratio of polyketal polyol and diisocyanate results in the formation of a linear polyketal polyurethane having more than one repeat unit corresponding to the repeat unit of structures III or IV; that is, for structure III, $\beta$ is at least 1 and in embodiments is between about 2 to 100, or between about 100 and 1000. The polyisocyanate employed may be difunctional or have higher functionality. Blends of diisocyanates with polyisocyanates having three or more isocyanate moieties are employed, in embodiments, to provide a tailored level of branching or crosslinking in the resulting polymer matrix.

In some embodiments, polyketal polyurethanes are formed by the reaction of one or more polyketal polyols of the invention with one or more polyketal polyisocyanates of the invention. In other embodiments, one or more polyketal polyols are reacted with one or more polyisocyanates that are not polyketal polyisocyanates. In still other embodiments, one or more polyketal polyisocyanates are reacted with one or more polyols that are not polyketal polyols, to form a polyurethane. Useful polyols for such embodiments include both polyketal polyols and any of the polyols listed above as polyols, first polyols, or second polyols. Various other embodiments employing one or more polyketal polyols, polyketal polyisocyanates, polyols, and polyisocyanates are easily envisioned. Blends of polyisocyanate functional and polyhydroxylated materials are used, in embodiments, to form polyketal polyurethanes having a varying range of ketal content and crosslink density and a wide range of available physical properties including glass transition temperature, tensile strength, ductility, and the like.

The reaction of an isocyanate group with an amine is known to form a urea linkage. Thus, in embodiments, one or more polyketal polyisocyanates, which already have one urethane linkage per isocyanate group, are reacted with one or more polyamines to form a poly(urethane urea). Suitable polyamines for forming one or more polyketal poly(urethane urea)s of the invention include, for example, hydrazine, ethane-1,2-diamine, 1,6-hexanediamine, but-2-ene-1,4-diamine, Metformin, butane-1,4-diamine, propane-1,2-diamine, benzene-1,3-diamine, 2-methylbenzene-1,3-diamine, 4-chlorobenzene-1,3-diamine, methanediamine, 1,3,5-triazine-2,4,6-triamine, N-(2-aminoethyl)ethane-1,2-diamine, N-(6-aminohexyl)hexane-1,6-diamine, N,N'-bis(2-aminoethyl)ethane-1,2-diamine, N-[2-(3-aminopropylamino)ethyl]propane-1,3-diamine, 4-(3,4-diaminophenyl)benzene-1,2-diamine, spermine (N,N'-bis(3-aminopropyl)butane-1,4-diamine), a polyethyleneimine, a polyoxyalkyleneamine having two or more amine groups, such as those sold under the trade name JEFFAMINE®, (available from the Huntsman Corp. of Salt Lake City, Utah), or any diamine or higher amine compound such as those sold under the trade name ELASTAMINE® (available from the Huntsman Corporation).

It is known that an isocyanate can be reacted with water to form a primary amine group and carbon dioxide; the primary amine is then available to react with another isocyanate group to form a urea linkage. Thus, in embodiments, one or more polyketal polyisocyanates of the invention are reacted with water to form one or more polyketal poly(urethane urea)s via a this known pathway. In some such embodiments, the evolution of carbon dioxide acts as a foaming agent as the reaction progresses, thus providing for a foamed polyketal poly(urethane urea) matrix. Water reacts with isocyanate groups to create carbon dioxide gas, which fills and expands cells created during the mixing process, and causes the formation of urea groups in a polyurethane reaction. Polyurethane and poly(urethane urea) foams have wide utility in the industry for applications such as automobile cushions, mattress material, furniture cushions, and the like.

The various polyketal polyurethanes and polyketal poly(urethane urea)s of the invention have a variable range of ketal content and a wide range of physical properties including glass transition temperature, clarity, rigidity and elasticity.

In a particularly useful range of embodiments, polyketal polyurethanes or polyketal poly(urethane urea)s are present as blocks in a copolymer with other polyurethane or poly(urethane urea) blocks. Such block copolymers are easily achieved by controlling stoichiometry of the reactions to reach the desired residual endgroups, then employing those endgroups as initiation points for an additional polymerization reaction with a different monomer mixture. For example, a bisketal diisocyanate of the invention may be reacted with ethylene glycol to form a polyurethane oligomer; the stoichiometry of the reaction is adjusted, using conventional techniques, to result in hydroxyl endgroups. The hydroxyl terminated polyurethane oligomer is then reacted with toluene diisocyanate to provide a diblock type polyurethane polymer.

In another useful range of embodiments, a polyketal polyester or copolyester can be synthesized according to the methods set forth above by homopolymerization or copolymerization of a bisketal diol. The resulting polyester of structures III or IV will inherently have, or may be reacted to provide, residual hydroxyl endgroups; the structures III and IV further have values of β of about 2 to 12, or about 12 to 100. The endgroups are useful in a subsequent reaction to form a polyurethane by reacting the hydroxyl terminated polyester or copolyester with a polyisocyanate or a polyketal polyisocyanate to produce a poly(ester urethane) polymer. Likewise, other similar embodiments may result in a poly(ester urethane urea) copolymer; the techniques employed in forming polyketal polyurethanes and polyketal poly(urethane urea)s may be usefully employed in making block copolymers with hydroxyl terminated polyketal polyesters and polyketal copolyesters. It will be understood by one of skill that further variations are possible. For example, when poly(ethylene glycol) is used as the polyol to make a polyester prior to reaction with a polyisocyanate, the resulting block copolymer will be a polyketal poly(ester ether urethane) or a polyketal poly(ester ether urethane urea).

Many other embodiments will be readily envisioned; it will be appreciated that the ketal content of the resulting polymer is variable in various embodiments, and a wide range of physical properties such as glass transition temperature, tensile strength, elasticity, and ductility are attainable in various embodiments of the invention.

The reactions and processes used to form various polyketal polyurethanes and polyketal poly(urethane urea)s, as well as poly(ester urethane)s and poly(ester urethane urea)s of the invention employ conventional techniques of polyurethane or polyurea synthesis; such techniques typically involve blending the two reagents in a stoichiometry that will result in oligomeric or polymeric molecular weights. In embodiments where polyurethane linkages are formed, the polymerization reaction is catalyzed. Catalysts useful in polyurethane formation include, in embodiments, tertiary amines. Nonlimiting examples of suitable tertiary amines include dimethylcyclohexylamine, 1,4-diazabicyclo[2.2.2]octane (also called DABCO or TEDA), and bis-(2-dimethylaminoethyl)ether. In other embodiments, organometallic compounds, such as dibutyltin dilaurate, potassium octanoate, or bismuth octanoate may be used to catalyze polyurethane formation. In some embodiments where polyurea linkages are formed, no additional catalyst is required to effect the reaction.

Processes that can be used to make these materials include, in embodiments, reaction injection molding, prepolymerization to a coatable syrup followed by coating and curing, and the like. The various polyketal polyurethanes, polyketal poly(urethane urea)s, poly(ester urethane)s, poly(ester urea)s, and poly(ester urethane urea)s of the invention are not particularly limited as to the methods employed in making and processing.

Foamed formulations employing the various polyketal polyurethanes, polyketal poly(urethane urea)s, polyketal poly(ester urethane)s, and polyketal poly(ester urethane urea)s of the invention are useful embodiments of the invention. Foams are formed during the polymerization reaction, typically by the addition of one or more blowing agents. One example is the use of carbon dioxide evolved in the reaction of isocyanate with water, as described above. In other embodiments, a blowing agent is added to the polymer during processing to facilitate foaming when the polymer is heated, for example in a thermoforming process. Suitable blowing agents include water, certain halocarbons such as HFC-245fa (1,1,1,3,3-pentafluoropropane) and HFC-134a (1,1,1,2-tetrafluoroethane), and hydrocarbons such as n-pentane. In some embodiments, blowing agents are incorporated into e.g. the polyketal polyol prior to the polymerization; in other embodiments the blowing agent is added as an auxiliary stream. Halocarbons and hydrocarbons are chosen such that they have boiling points at or near room temperature; these blowing agents volatilize into a gas during the exothermic polymerization reaction. In addition, high density microcellular foams can be formed without the addition of blowing agents by mechanically frothing or nucleating the polyol component prior to use.

In some embodiments, surfactants are employed to modify the characteristics of the foam during the foaming process. In embodiments, they are used to emulsify the liquid components, regulate cell size, and stabilize the cell structure to prevent collapse and surface defects. Rigid foam surfactants produce, in embodiments, very fine cells and very high closed cell content. In other embodiments, flexible foam surfactants stabilize the reaction mass while maximizing open cell content to prevent the foam from shrinking. The need for, and choice of, surfactant is determined, in embodiments, by choice of polyisocyanate, polyol, component compatibility, system reactivity, process conditions and equipment, tooling, part shape, and shot weight.

Various embodiments of the polyketal polyurethanes, polyketal poly(urethane urea)s, poly(ester urethane)s, and poly(ester urethane urea)s of the invention are useful in a broad range of applications. Polyurethane polymers, in general, are compounds of exceptional industrial utility; they find numerous applications because the final properties of the resulting polymer can be influenced greatly through selection of active hydrogen monomers (typically, polyhydroxyl compounds) and isocyanates used, and by selecting the conditions used to prepare the finished polymer products. Polyurethanes are lightweight, strong, durable and resistant to abrasion and corrosion. Depending on choice of monomers, a polyurethane is stiff or flexible. Typically, incorporation of urea type linkages results in a more rigid material. However, with the broad range of monomer chemistry as well as the range of linkages available from ester, urethane, and urea moieties in various embodiments provides extensive flexibility in choice of structure that leads to a broad range of properties and, in turn, applications.

Without providing any particular limitations, the various polyketal polyurethanes, polyketal poly(urethane urea)s, poly(ester urethane)s, and poly(ester urethane urea)s of the invention are useful, in embodiments, as adhesives or sealants, particularly for exterior uses or building construction applications where extremely challenging conditions are encountered; as binders; as coating materials where durability and/or challenging environmental conditions exist; in reactive spray coatings of 100% solids; as elastomers for applications such as rollers and belts for carrying heavy and/or abrasive materials, roller blades, and other footwear parts such as shoe soles; as vibration damping materials; and in the fabrication of medical devices, for example for surface modification, as a protective coating, or within moving parts (e.g. for elastomeric materials). In foamed form, these materials also find utility as insulation materials; low density vibration damping materials; flexible foam for indoor furniture such a seat cushions and mattresses, and other similar applications such as automobile seat cushions.

F. Polyketal Ester Polycarbonates

Polyketal polyols having structures I, II, III, or IV are useful, in embodiments, for the synthesis of polycarbonates. Where compounds of structures I or III are employed, the polyketal polyols useful in the synthesis of polycarbonates typically have a of 1 or 2. In embodiments, dimers, oligomers, or polymers having structures III or IV may are used to synthesize one or more polyketal polycarbonates of the invention, wherein the value of β is 2, or between about 3 and 12, or between about 12 and 100.

Polycarbonate synthesis is carried out, in embodiments, by employing any known and conventional technique for making polycarbonates. One such technique employs phosgene. For example, in one such embodiment, a bisketal diol is treated with sodium hydroxide, followed by an interfacial reaction between the sodium alkoxide of the bisketal diol and phosgene. Alternatively, one or more polyketal polycarbonates of the invention are synthesized, in embodiments, by transesterification of a polyketal ester with a difunctional carbonate having the general structure

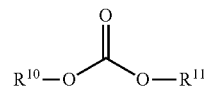

where $R^{10}$ and $R^{11}$ may be the same or different and are, in embodiments, a linear, cyclic, or branched alkyl, alkenyl, or alkynyl group; an aralkyl group, or an aromatic group; or $R^{10}$ and $R^{11}$ together with the carbonate bond forms, in some embodiments, a cyclic carbonate. In such embodiments, a polycarbonate is formed by a ring opening reaction. The reaction to form polycarbonates A polyketal polycarbonate is also formed, in embodiments, by reacted a dibromo compound with potassium carbonate. Thus, in one such embodiment employing the reaction conditions set forth in the reference article, a bisketal having two or more $R^1$ groups containing a primary bromo moiety is reacted with potassium carbonate to form a polyketal polycarbonate of the invention.

Polyketal ester polycarbonates employ, in embodiments, one or more polyketal polyols of the invention; they further incorporate one or more acyclic or cyclic dialkyl carbonate monomers or another source of carbonate bond such as potassium carbonate or phosgene.

The polyketal ester polycarbonates of the invention have a range of available properties due to the broad range of polyketal polyols of the invention that are available as starting materials. Polycarbonates are known to be tough, transparent, thermally stable materials suitable for a range of engineering plastics applications. Suitable applications for one or more polycarbonates of the invention include, but are not limited to, fabrication of items requiring molding, laminating, thermoforming such as extruding or coextruding, or machining or other conventional means of working. Examples of useful items include compact discs, riot shields, baby bottles and other water/drink bottles and food containers, electrical components, automobile headlamps, as a component of a safety glass laminate, eyeglass lenses, safety helmets, and the like.

Various polyketal ester polycarbonates of the invention do not employ Bisphenol A (4,4'-dihydroxy-2,2-diphenylpropane), the most commonly employed polycarbonate polyol starting material. Bisphenol A has been the subject of toxicity concerns since the 1930s, particularly in food or drink contact applications (e.g., baby bottles, water/drink bottles, food containers). One or more polycarbonates of the invention are, in one or more embodiments, are useful for food or drink applications where it is desirable to eliminate Bisphenol A.

Additionally, some aliphatic polyketal ester polycarbonates of the invention are, in some embodiments, biodegradable. Biodegradable polycarbonates are useful for one or more applications, for example, in food or drink contact applications, to enable disposable embodiments of various containers. Other applications where biodegradability is advantageous include disposable medical supplies such as eye shields and the like. In various embodiments, the polyketal ester polycarbonates of the invention advantageously supply the desirable properties of polycarbonates and additionally supply biodegradability thereof.

In some embodiments, polyketal ester polycarbonates of the invention, when terminated by hydroxyl endgroups, are suitable as diols for use in polyurethane synthesis. Polyketal ester polycarbonate diols are synthesized, in some embodiments, by employing polyketal polyols in the synthesis of a polycarbonate and controlling stoichiometry of the polymerization in order to provide hydroxyl functionality at the ends of the polymer. In other embodiments, a polycarbonate is transesterified at each end with a diol to provide hydroxyl endgroup. Polyketal ester polycarbonates having hydroxyl endgroups are reacted with a diisocyanate to form a polyketal poly(carbonate urethane). Polyketal poly(carbonate urethane)s are synthesized using, in some embodiments, the techniques described above to make polyketal polyurethanes. In other embodiments, techniques used to form the Polyketal poly(carbonate urethane)s of the invention are those outlined in Moore et al., *Novel Co-Polymer Polycarbonate Diols for Polyurethane Elastomer Applications*, Proceedings of the Polyurethanes Expo 2003, Oct. 1-3, 2003 (© 2003, American Chemistry Council).

G. Polyketal Acrylates and Methacrylates, and Their Polymerized Products

Polyketal polyols having structures I, II, III and IV are useful, in embodiments, for the synthesis of acrylate or methacrylate adducts thereof. Any of the above embodiments of the invention wherein a polyketal has one or more hydroxyl functionalities are, in embodiments, functionalized with one or more acrylic functionalities. Such embodiments include structures of compounds I and III wherein $\alpha$ is 1; or wherein $\alpha$ is 2; or wherein $\alpha$ is between about 3 and 100. Such embodiments also include structures of compounds III and IV wherein $\beta$ is 2; or wherein $\beta$ is about 2 to 12; or wherein $\beta$ is between about 3 and 100.

As used herein, the term "acrylic functionality" means an acrylate, methacrylate, or other similar moiety that is capable of subsequent polymerization or crosslinking reactions utilizing a free radical or redox mechanism. Acrylic functionality is imparted, in embodiments, to one or more of the polyketal polyols of the invention by employing conventional techniques for the reaction of alkanols to form acrylates and methacrylates. In one such embodiment a polyketal polyol or a dimer, oligomer, or polymer thereof having at least one free hydroxyl group is employed in an esterification reaction with acrylic acid or methacrylic acid to form a polyketal acrylate. Another embodiment employs acrylyl chloride or methacrylyl chloride in a reaction with a polyketal polyol of structures I, II, III, or IV having at least one free hydroxyl group to form the corresponding acrylic functional polyketal and HCl. The HCl is advantageously scavenged by a base, for example ammonia, to capture the acid and prevent unwanted side reactions.

In a related set of embodiments, a polyketal polyisocyanate of the invention may be reacted with a hydroxyl-functional acrylate or methacrylate to form a urethane moiety linking the polyketal to the acrylate or methacrylate moiety. For example, a polyketal polyisocyanate such as the structure shown in FIG. 1D is reacted with a 3-methacrylyl-2-hydroxylpropyl ester to give the corresponding polyketal urethane methacrylate. In another example, the polyketal polyisocyanate shown in FIG. 1D is reacted with 2-hydroxypropyl acrylate to give the corresponding polyketal urethane acrylate. Polyurethane acrylates are known in the literature and are typically formed by synthesizing polyurethane from a diol and a diisocyanate, followed by endcapping the polyurethane isocyanate endgroup with a hydroxy functional acrylate or methacrylate as described herein above. Alternatively, the polyurethane is hydroxy endcapped and is esterified with acrylic acid or methacrylic acid. For example, Barbeau, et al., *Journal of Polymer Science Part B: Polymer Physics*, 38(21), 2750-68 (2000) show a typical reaction scheme for a prepolymer that is a polyurethane having isocyanate endgroups, endcapped with an acrylate group. In some embodiments, the polyketal polyisocyanates of the invention are acrylate functionalized using this or a similar method. The acrylate functionality is then polymerized to give an acrylate polymer network. In yet another variation of this chemistry, an isocyanate endcapped material is crosslinked with a hydroxy-functional polymer, such as poly(2-hydroxypropyl acrylate) or poly(vinyl alcohol); see, for example, Decker et al., *Macromol. Mater. Eng.* 286, 5-16 (2001). In some embodiments, the polyketal polyisocyanates of the invention are functionalized with an acrylate polymer using this or a similar method.

The various polyketal acrylates and polyketal methacrylates of the invention have, in various embodiments, one or more acrylic functionalities present as $R^1$ fragments in structures I, II, III, or IV. The $\alpha,\beta$-unsaturated portion of acrylic functionalities are capable of radical, cationic, or anionic polymerization to result in a polymer network. Such reactions are widely used in the industry and one or more acrylate functional polyketals of the invention may be reacted using any of the known techniques of polymerization or crosslinking of acrylate functionalities. Many references are available that discuss these techniques. Radical polymerization or crosslinking reactions initiated by thermal, redox, electromagnetic radiation such as ultraviolet (UV), or electron beam (ebeam) are the most common of these known techniques. Some useful references discussing such means of polymerization of acrylate functional materials are Decker et al., *Macromol. Mater. Eng.* 286, 5-16 (2001); Burlant, W., U.S. Pat. No. 3,437,514; Endruweit, et al., *Polymer Composites* 2006, 119-128; Decker, C., *Pigment and Resin Technology* 30(5), 278-86 (2001); and Jönsson et al., *Progress in Organic Coatings* 27, 107-22 (1996). Other known and useful methods are those taught by U.S. Pat. Nos. 3,437,514; 3,528,844; 3,542,586; 3,542,587; 3,641,210. Such polymerization reactions are particularly advantageous where one or more polyketals of the invention are polymerized or crosslinked, for example, in situ in a coated formulation, in a syrup preparation for coating, and the like. Any of the techniques employed in these references may be advantageously employed to react the acrylate functional polyketals of the invention, resulting in linear, branched, or crosslinked polymer networks.

Many useful extensions of the above embodiments of the invention are readily envisioned wherein the acrylate functional polyketals are employed. For example, in one embodiment, a bisketal diol is acrylate functionalized and employed as a crosslinker when blended with additional acrylate functional compounds, typically monoacrylate functional compounds, in a radical polymerization reaction. In other embodiments, any one or more of the polyketal polymers described above are provided with acrylic functionality by employing the reactions described above, to form polyketal acrylate prepolymers. In some such embodiments, the polyketal acrylate prepolymers are processed, for example by coating, extruding, mold filling, and so forth, with or without additional solvents, prior to reaction of the acrylate groups. The acrylate functional polyketal polymers may further be blended with one or more additional acrylate functional compounds and/or additional vinyl functional compounds. After processing, the polyketal acrylate prepolymers are reacted to form a polymerized and/or crosslinked network. The resulting networks are thermoset or thermoplastic, depending on whether or not the network is crosslinked. It is readily understood that the properties of the networks will vary greatly depending on both the nature of the compounds used and crosslink density.

Additional acrylate functional compounds include compounds having one or more acrylate, alkylacrylate, acrylamide, or alkylacrylamide residues. Non-limiting examples of useful acrylate functional compounds include acrylic acid, methacrylic acid, acrylamide, methacrylamide, N-hydroxymethyl acrylamide, methacryloxyethyl phosphate, acrylonitrile, methacrylonitrile, 2-acrylamido-2-methylpropanesulfonic acid and salts thereof; maleic acid, its salt, its anhydride and esters thereof; monohydric and polyhydric alcohol esters of acrylic and alkylacrylic acid such as 1,6 hexane diol diacrylate, neopentyl glycol diacrylate, 1,3 butylene dimethacrylate, ethylene glycol diacrylate, trimethylolpropane triacrylate, pentaerythritol triacrylate, pentaerythritol tetracrylate, etc.; other oxygenated derivatives of acrylic acid and alkylacrylic acids, e.g., glycidyl methacrylate, hydroxyethyl methacrylate, hydroxypropyl methacrylate, etc.; halogenated derivatives of the same, e.g., chloroacrylic acid and esters thereof; and diacrylates and dimethacrylates, e.g., ethylene glycol diacrylate. In some embodiments, the additional acrylate functional compounds are present in blends with acrylate functional polyketals of up to about 50 mole percent, such as between about 1 and about 40 mole percent, of additional acrylate functional compounds.

Additional vinyl functional compounds include non-acrylate functional $\alpha,\beta$-unsaturated compounds capable of copolymerizing with the acrylate functional compounds and/or acrylate functional polyketals. Non-limiting examples of additional vinyl compounds include aromatic polyvinyl compounds such as divinyl benzene, aromatic monovinyl compounds such as styrene, methyl substituted styrenes such as $\alpha$-methyl styrene, vinyl toluene, t-butyl styrene, chlorostyrene, and the like; aliphatic monovinyl compounds such as $\alpha$-olefins, e.g. propylene, 1-octene, and the like. Other additional vinyl functional compounds useful in blends with the acrylate functional polyketals are the divinyl and tetravinyl compounds disclosed in U.S. Pat. Nos. 3,586,526; 3,586,527; 3,586,528; 3,586,529; 3,598,530; 3,586,531; 3,591,626; and 3,595,687.

H. Allyl Functional Polyketals

Polyketal acids and esters having structures I, II, III and IV are useful, in embodiments, for the synthesis of allyl adducts thereof. Any of the above embodiments of the invention wherein a polyketal has one or more acid or ester groups are, in embodiments, functionalized with one or more allyl functionalities. Such embodiments include structures of compounds I and III wherein $\alpha$ is 1; or wherein $\alpha$ is 2; or wherein $\alpha$ is between about 3 and 100. Such embodiments also include structures of compounds III and IV wherein $\beta$ is 2; or wherein $\beta$ is about 2 to 12; or wherein is between about $\beta$ and 100.

As used herein, the term "allyl functionality" means a —$CH_2$—$CH$=$CH_2$ moiety that is capable of subsequent polymerization or crosslinking reactions utilizing a free radical or redox mechanism. Allylic polyketals are polyketals, polyketal polyols, polyketal polyamines, dimers, oligomers, and polymers thereof having allyl functionality.

Allyl alcohol is employed, in embodiments, to synthesize allyl derivatives of the polyketal acids or esters thereof by esterification or transesterification reaction using any of the known techniques commonly employed in the literature. For example, allyl alcohol is esterified with a free carboxylic acid in the presence of an organic sulfonic acid esterification catalyst and a polymerization inhibitor in U.S. Pat. No. 2,249,768. In other embodiments, allyl alcohol is employed in a transesterification reaction of the carboxylate moiety present on a polyketal. Suitable methods of transesterification to form allyl esters of any of the polyketal esters of the invention are disclosed in Remme et al., *Synlett* 2007, 3, 491-3 and U.S. Pat. No. 5,710,316; other suitable methods are disclosed in Singh et al., *J. Org. Chem.* 2004, 69, 209-12 and Chavan et al., *Synthesis* 2003, 17, 2695-8. Allyl monohalides are also employed, in embodiments, to synthesize one or more allyl esters of the polyketals of the invention by employing a polyketal ester and a catalyst that is palladium halide or platinum halide, a technique employed in, for example, U.S. Pat. No. 3,699,155. These and other methods are used, in embodiments, to synthesize allylic esters of the polyketals of the invention.

The one or more allylic polyketals of the invention are, in embodiments, polymerized using any of the techniques known in the literature. For example, heating allyl monomers in the presence of thermal free-radical initiators gives polymeric products. Typically, allyl polymers are made by charging the allyl monomer and a free-radical initiator to a reactor, and heating the mixture at a temperature effective to polymerize the monomer (see, e.g. "Kirk-Othmer Encyclopedia of Chemical Technology," $4^{th}$ ed., Volume 2, pp. 161-179). Improved methods of polymerizing allyl compounds are also usefully employed with one or more allylic polyketals of the invention. For example, U.S. Pat. No. 5,420,216 discloses that gradual addition of initiator is key to high conversion in allyl polymerization.

In some embodiments of the invention, one allyl group per molecule provides sufficient reactivity to result in high conversion or high molecular weight of the radically polymerized product. In other embodiments, two or more reactive double bonds per molecule yields solid, high molecular weight polymers by initiation with a suitable free-radical catalyst. Such embodiments are useful to provide, for example, heat-resistant cast sheets and thermoset moldings. In some such embodiments, the reactivity of compounds having more than one allyl group permits polymerization in two stages: a solid prepolymer containing reactive double bonds is molded by heating; then completion of polymerization gives cross-linked articles of superior heat resistance. In embodiments, the relatively slow rate of polymerizations is controlled more readily than in the polymerization of polyfunctional vinyl compounds to give soluble prepolymers containing reactive double bonds.

One useful embodiment of one or more allylic polyketals of the invention employs minor proportions of one or more polyfunctional allylic polyketals for cross-linking or curing preformed vinyl-type polymers. Among the preformed polymers cured by minor additions of allyl ester monomers and catalysts followed by heat or irradiation are polyethylene, PVC, and acrylonitrile-butadiene-styrene (ABS) copolymers. These reactions are examples of graft copolymerization in which specific added peroxides or high energy radiation achieves optimum cross-linking. In other embodiments, small proportions of mono- or polyfunctional allylic polyketals are added as regulators or modifiers of vinyl polymerization for controlling molecular weight and polymer properties. In yet other embodiments, polyfunctional allylic polyketals of high boiling point and compatibility are employed as stabilizers against oxidative degradation and heat discoloration of polymers.

One useful embodiment of one or more thermoset allylic polyketals of the invention is in moldings and coatings for electronic devices requiring high reliability under long-term adverse environmental conditions. These devices include electrical connectors and insulators in communication, computer, and aerospace systems. Other embodiments are readily envisioned.

I. Epoxy Functional Polyketals

Polyketal acids, esters, polyols, and polyisocyanates having structures I, II, III and IV are useful, in embodiments, for the synthesis of glycidyl adducts thereof. Any of the above embodiments of the invention wherein a polyketal has one or more hydroxyl functionality are, in embodiments, functionalized with one or more glycidyl functionalities. Such embodiments include structures of compounds I and III wherein α is 1; or wherein α is 2; or wherein α is between about 3 and 100. Such embodiments also include structures of compounds III and IV wherein β is 2; or wherein β is about 2 to 12; or wherein β is between about 3 and 100.

Polyketal acids and esters having structures I, II, III and IV are useful, in embodiments, for the synthesis of allyl adducts thereof. Any of the above embodiments of the invention wherein a polyketal has one or more acid or ester groups are, in embodiments, functionalized with one or more allyl functionalities.

As used herein, the term "glycidyl functionality" means a methyl oxirane, or epoxy, moiety that is capable of subsequent polymerization or crosslinking reactions utilizing a ring opening reaction. Glycidyl polyketals are polyketals, polyketal polyols, and dimers, oligomers, and polymers thereof having one or more glycidyl functionalities.

Glycidyl alcohol is employed, in some embodiments, to synthesize glycidyl esters of the polyketal acids or esters thereof by esterification or transesterification reaction using any of the known techniques commonly employed in the literature. For example, Chanda, M. and Roy, S., eds., *Plastics Technology Handbook*, 4$^{th}$ ed., © 2007 Taylor & Francis Group, LLC, pp. 4-114 to 4-116; and U.S. Pat. No. 5,536,855 describe some of the methods that are useful, in embodiments, to react one or more polyketal acids or esters of the invention with glycidyl alcohol. In other embodiments, glycidyl alcohol is reacted with one or more polyketal polyisocyanates of the invention to give the corresponding polyketal glycidyl urethanes, using techniques commonly employed to react an alcohol with an isocyanate group.

In other embodiments, an epihalohydrin such as epichlorohydrin is used to functionalize one or more polyketal polyols of the invention. The reaction between an alcohol and epichlorohydrin to form a glycidyl ether is known in the literature. For example, the reaction of the alcohol Bisphenol A with epichlorohydrin is a well known reaction by which epoxy resins are formed. A similar process is used in some embodiments of the invention to form one or more epoxy functional polyketals of the invention. For example, U.S. Pat. No. 5,420,312 describes techniques of forming glycidyl ethers of alcohols. This and other conventional techniques employed to react epichlorohydrin with an alcohol are, in embodiments, employed using the polyketal polyols of the invention to form glycidyl ethers. Epichlorohydrin is also, in embodiments, reacted directly with carboxylic acids to form the corresponding glycidyl ester; the reaction involves ring opening of the glycidyl moiety, followed by dehydrochlorination to re-form the oxirane ring. In embodiments, glycidyl esters of one or more polyketal acids of the invention are formed by reacting a polyketal acid of the invention having one or more free carboxylic acid groups with one or more equivalents of epichlorohydrin. Such a reaction is carried out, in one or more embodiments, by employing the techniques of Bukowska, et al., *J. Chem. Tech. and Biotech.*, 74: 1145-1148 (1999); Otera et al., Synthesis (12), 1019-1020 (1986); U.S. Pat. No. 3,576,827; British Patent No. GB 884,033; and German Patent Appl. No. DE 15945/70; or by other techniques found in the literature. In still other embodiments, the ionic salts of the polyketal carboxylates of the invention are reacted with an epihalohydrin, such as epichlorohydrin, to form the corresponding glycidyl esters. In such embodiments, the techniques employed by, for example, Maerker et al., J. Org. Chem. 26, 2681-2688 (1961) are useful, among other techniques.

Another technique employed, in some embodiments, to provide glycidyl functionality to one or more polyketal esters of the invention is to react an unsaturated ester of a polyketal with a peroxide. For example, U.S. Pat. No. 5,036,154 discloses a method whereby an ethylenically unsaturated ester group, such as an allyl ester, is reacted with hydrogen peroxide in the presence of an alkali metal or alkaline earth metal salt of tungstic acid, phosphoric acid, and a phase transfer catalyst to give the epoxidized product of the unsaturated moiety. Such a technique is used, in embodiments, to form a glycidyl ester of a polyketal of the invention from the corresponding allyl ester, the allyl ester functionalized polyketals of the invention having been described in section H. above. Other techniques employed in the literature are similarly useful to obtain one or more epoxidized products of allyl esters of the invention. For example, esterification of various polyketals of the invention with an unsaturated fatty acid ester is followed, in embodiments, by reacting the unsaturated site with hydrogen peroxide, as is described by Du et al., *J. Am. Org. Chem. Soc.* 81(4) 477-480 (2004).

One or more epoxy functionalized polyketals of the invention are, in embodiments, subsequently polymerized using standard techniques from the literature. The polymerization of epoxy groups, for example with amines, amides, or anhydrides, is widely known. A useful summary of compounds and mechanisms of curing epoxy groups is found in Chanda, M. and Roy, S., eds., *Plastics Technology Handbook*, 4$^{th}$ ed., © 2007 Taylor & Francis Group, LLC, pp. 4-116 to 4-122. Any of the techniques employed or referenced therein are used, in various embodiments, to polymerize the epoxy groups present on one or more polyketal glycidyl esters of the invention to form the corresponding linear or crosslinked polymer.

Applications of epoxy polymers are numerous and broad in scope. Due to their high strength, variable crosslink density, and variable chemical starting materials, epoxies have found broad applicability for numerous applications. Many of the most common applications are set forth in Chanda, M. and Roy, S., eds., *Plastics Technology Handbook*, 4$^{th}$ ed., © 2007 Taylor & Francis Group, LLC, pp. 2-80 to 2-81, 7-26, and 4-124 to 4-125. The epoxy resins formed by curing the epoxy functional polyketal esters of the invention are, in various embodiments, useful in one or more of these applications.

The polyketal compounds and dimers, oligomers, and polymers having structures I, II, III, and IV, further as embodied in sections A. to I., are useful in a wide variety of industrially useful and significant applications. The various polyketal polymers of the invention are, in embodiments, used in blends, optionally obtained by reactive extrusion. Blends include blends of various species of the polyketal polymers of the invention as well as blends with such polymers as aliphatic/aromatic copolyesters, as for example polybutylene terephthalate adipate (PBTA), polybutylene terephthalate succinate (PBTS), and polybutylene terephthalate glutarate (PBTG); biodegradable polyesters such as polylactic acid, poly-ε-caprolactone, polyhydroxybutyrates such as poly-3-hydroxybutyrates, poly-4-hydroxybutyrates and polyhydroxybutyrate-valerate, polyhydroxybutyrate-propanoate, polyhydroxybutyrate-hexanoate, polyhydroxybutyrate-decanoate, polyhydroxybutyrate-dodecanoate, polyhydroxy-butyrate-hexadecanoate, polyhydroxybutyrate-octadecanoate, and polyalkylene succinates and their copolymers with adipic acid, lactic acid or lactide and caprolactone and their combinations, and the like; polystyrene and copolymers thereof; polyurethanes; polycarbonates; polyamides such as Nylon 6 and Nylon 6,6; polyolefins such as polyethylene, polypropylene, and copolymers thereof; or any other industrially useful polymeric compounds. Blends also include, in some embodiments, composites with gelatinized, destructed and/or complexed starch, natural starch, flours, and other materials of natural, vegetable or inorganic origin.

One or more polyketal polymers of the invention are, in some embodiments, blended with polymers of natural origin, such as starch, cellulose, chitosan, alginates, natural rubbers or natural fibers (such as for example jute, kenaf, hemp). The starches and celluloses can be modified, such as starch or cellulose esters with a degree of substitution of between 0.2 and 2.5, hydroxypropylated starches, or modified starches with fatty chains, among others.

The various polyketal compounds and polymers made therefrom according to the invention, and blends of thereof, possess properties and values of viscosity that render them suitable for use, by appropriately adjusting the molecular weight, in numerous practical applications, such as films, injection-molded products, extrusion coated products, fibers, foams, thermoformed products, extruded profiles and sheets, extrusion blow molding, injection blow molding, rotomolding, stretch blow molding and the like.

In the case of films, production technologies like film blowing, casting, and coextrusion can be used. Moreover such films can be subject to monoaxial or biaxial orientation in line or after film production. It is also possible that the stretching is obtained in presence of an highly filled material with inorganic fillers. In such a case, the stretching can generate micropores and the so obtained film can be suitable for hygiene applications.

The various polyketal compounds and polymers made therefrom according to the invention are suitable for the production of films. A "film" is defined, for the purposes of various embodiments of the invention, as a sheet type material that is flexible to e.g. bending and is between about 1 μm to 5 mm thick. Films may be made using one or more polyketal polymers of the invention; or they can be made using another polymer blended with a polyketal compound. Films employing various polyketal compounds and polymers made therefrom of the invention are, in embodiments, one-directional or two-directional, single layer or multilayer, and employ one or more polyketal polymers of the invention as a single component or in a blend with other materials, as described above. The films are useful for various applications including agricultural mulching films; printable films for graphics or text; cling films (extensible films) for foodstuffs, films for bales in the agricultural sector and for wrapping of refuse; shrink films such as for example for pallets, mineral water, six pack rings, and so on; bags and liners such as for collection of refuse, holding foodstuffs, gathering mowed grass and yard waste, and the like; thermoformed single-layer and multilayer packaging for foodstuffs, such as for example containers for milk, yoghurt, meat, beverages, etc.; and in multilayer laminates with layers of paper, plastic materials, aluminum, and metalized films for a wide variety of applications.

The various polyketal compounds and polymers made therefrom of the invention are also useful for coatings that form a layer on top of a film, an article, and the like. A coating may be up to several millimeters thick, or it may be a single molecular layer. Coatings of the invention are applied, in embodiments, by extrusion coating, die coating, slot coating, brush coating, spray coating, or any other generally known technique employed in the coating industry. Coatings employing various polyketal compounds and polymers made therefrom of the invention are useful as protective coatings, paint components, adhesives or glues, barrier layers, and the like. One or more coatings of the invention are applied, in embodiments, with or without additional solvent(s), such as coalescing solvents, and with our without additives such as UV blocking agents, antibacterial agents, colorants, fillers, and the like. One or more coatings of the invention are, in some embodiments, crosslinked after application.

Various polyketal compounds and polymers made therefrom of the invention are also useful in forming articles. An "article", as defined for the purposes of the invention, includes objects that are be rigid or flexible; that exist as standalone objects or as part of an assembly or laminate; and that include one or more polyketal compounds and polymers made therefrom of the invention or a blend thereof, optionally with one or more additional materials. Some examples of useful articles that include various polyketal compounds and polymers made therefrom of the invention are punnets for foodstuffs, I-beams for construction, casings for e.g. pens, computer screens, and the like; parts for automobile construction, table tops, and the like; decorative items such as lamp parts, jewelry, vases, architectural features, and the like; children's toys; drink bottles; and many other articles. The invention is not particularly limited in terms of what articles may be formed employing the various polyketal compounds and polymers made therefrom of the invention.

Articles that can be formed include foamed articles. Foaming of polyurethanes are discussed above; those techniques and others generally known in the industry are used, in embodiments, to form foamed articles from the various polyketal compounds and polymers made therefrom of the invention. Foamed articles include both rigid and flexible foams. Some examples of useful foamed materials include cushions for automobile seats, interior or exterior furniture, and the like; foamed or foamable beads for the production of pieces formed by sintering; foamed blocks made up of pre-foamed particles; foamed sheets, thermoformed foamed sheets, and containers obtained therefrom for the packaging of foodstuffs.

Articles also include fibrous articles. Examples of fibrous articles include standard scale fibers, microfibers, nanofibers, and composite fibers. Composite fibers have, in embodiments, a core constituted by a rigid polymer such as PLA, PET, PTT, etc. and an external shell made with one or more polyketal compounds and polymers made therefrom of the invention; other composite fibers have various section configurations (from round to multilobed). Fibers also include flaked fibers, woven and non-woven fabrics or spun-bonded or thermobonded fabrics for the sanitary sector, the hygiene sector, the agricultural sector, georemediation, landscaping and the clothing sector.

The present invention contemplates, in one embodiment, a polyketal having structure I:

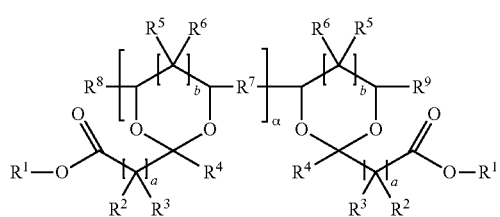

wherein
α is an integer of at least 1;
$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ may be the same or different for each occurrence;

$R^2$, $R^3$, $R^4$, $R^5$, and $R^6$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ may be the same or different for each occurrence;

$R^7$ is a covalent bond, methylene, ethylene, hydroxymethylene, oxygen, or —CH$_2$—O—CH$_2$— and $R^7$ is the same or different for each occurrence;

$R^8$ and $R^9$ are independently hydrogen, a linear, branched, or cyclic alkyl, a linear, branched, or cyclic alkenyl, alkynyl, aryl, alkaryl, or a polymeric moiety; and optionally contains one or more heteroatoms;

a is 0 or an integer of 1 to 12; and b is 0 or 1 wherein b=0 indicates a five membered ring,

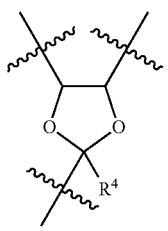

b=1 indicates a 6 membered ring,

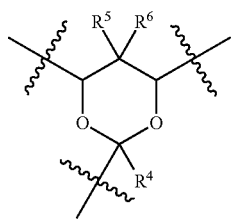

and b may be the same or different for each occurrence.

The $R^1$ group of the polyketal I is, in embodiments, ethyl, butyl, or 2-ethylhexyl. The $R^1$ group of the polyketal I is, in embodiments, the residue of a polyol. The polyol is, in embodiments, ethylene glycol, diethylene glycol, pentaerythritol, 1,6-hexanediol, glycerol, or diglycerol. The $R^1$ group of the polyketal I contains, in embodiments, one or more isocyanate, acrylate, methacrylate, allyl, or oxirane groups. In embodiments of the polyketal I, all $R^2$ and $R^3$ are hydrogen, all $R^4$ are methyl, and all values of a equal 2. In embodiments of the polyketal I, all values of b equal 0. In embodiments of the polyketal I, all values of b equal 1 and all $R^5$ and $R^6$ are hydrogen. In embodiments of the polyketal I, α equals 1 or 2 and $R^8$ and $R^9$ are hydrogen. In embodiments of the polyketal I, α equals 1 and b equals 0. In embodiments of the polyketal I, α is between about 2 and 1000, all values of b equal 1, and all $R^5$ and $R^6$ are hydrogen. In some such embodiments, α is between about 10 and 100. In some such embodiments, one or more of $R^8$ and $R^9$ are residues of a polymer. In some such embodiments, the polymer residue is a poly(vinyl alcohol) residue, poly(vinyl acetate) residue, polyethylene residue, polypropylene residue, or a random or block copolymer residue thereof.

The present invention contemplates a formulation comprising the polyketal having structure I. The formulation comprises, in embodiments, one or more additional polymers. The one or more additional polymers comprise, in embodiments, poly(3-hydroxybutyrate-co-3-hydroxyvalerate), poly(vinyl chloride), poly(lactic acid), or polystyrene. In the formulation, the polyketal having structure I is, in embodiments, a plasticizer, a toughener, a surfactant, a coalescing solvent, a compatibilizer, a barrier layer compound, an interfacial modifier, or a phase transfer compound. The formulation can further comprise one or more solvents. The one or more solvents comprise, in embodiments, two immiscible solvents, wherein the formulation comprises a homogeneous mixture. In some embodiments of the formulation comprising two immiscible solvents, wherein the formulation comprises a homogeneous mixture, the polyketal of structure I is about 0.01 vol % to 50 vol % percent based on total volume of the one or more solvents, and the homogeneous mixture comprises between about 5 vol % to 95 vol % methanol based on the total volume of the one or more solvents. In other embodiments of the formulation comprising two immiscible solvents, wherein the formulation comprises a homogeneous mixture, the polyketal of structure I is present at about 0.1 vol % to 20 vol % based on the total volume of the one or more solvents. In other embodiments of the formulation comprising two immiscible solvents, wherein the formulation comprises a homogeneous mixture, the polyketal of structure I is present at about 1 vol % to 10 vol % based on the total volume of the one or more solvents. In some embodiments of the formulation comprising two immiscible solvents, wherein the formulation comprises a homogeneous mixture, the two immiscible solvents comprise a hexane methanol blend or a methanol water blend. In some embodiments of the formulation comprising a hexane methanol blend or a methanol water blend, the methanol is present at about 50 vol % based on the total volume of the one or more solvents. In some embodiments of the formulation comprising a hexane methanol blend or a methanol water blend, the polyketal $R_1$ is butyl, $R_2$, $R_3$, $R_8$, and $R_9$ are hydrogen, a is 2, b and c are 0, and α is 1. In embodiments, the formulation comprising the polyketal of structure I is a coating formulation. In embodiments, the formulation comprising the polyketal of structure I is an adhesive formulation.

The present invention contemplates an article comprising the polyketal having structure I. In embodiments, the article comprising the polyketal having structure I is coated, cast, extruded, coextruded, profile extruded, blow molded, injection molded, co-injection molded, thermoformed, or reaction injection molded. In embodiments, the article comprising the polyketal having structure I comprises two or more layers and the polyketal of structure I is present in at least one layer. In embodiments, the article comprising the polyketal having structure I comprises a film, a sheet, a fiber, a foamed article, a woven fabric, a nonwoven fabric, or a pressure sensitive adhesive tape, or a paint coating.

The present invention contemplates a bisketal having structure II:

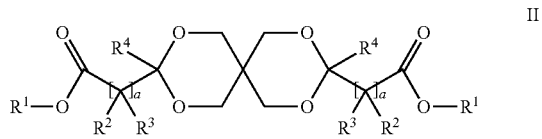

wherein:

$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$ and $R^3$ are independently hydrogen, a linear, branched, or cyclic alkyl, a linear, branched, or cyclic alkenyl, alkynyl, aryl, or alkaryl; and optionally contains one or more heteroatoms; and $R^2$ and $R^3$ are the same or different for each occurrence;

$R^4$ is a linear, branched, or cyclic alkyl, a linear, branched, or cyclic alkenyl, alkynyl, aryl, or alkaryl; and optionally contains one or more heteroatoms; and $R^4$ is the same or different for each occurrence; and a is 0 or an integer of 1 to 12.

In some embodiments of the bisketal of structure II, one or more $R^1$ is ethyl, butyl, or 2-ethylhexyl. In some embodiments of the bisketal of structure II, one or more $R^1$ is the residue of a polyol. In some embodiments of the bisketal of structure II wherein one or more $R^1$ is the residue of a polyol, the one or more polyol is ethylene glycol, diethylene glycol, pentaerythritol, 1,6-hexanediol, glycerol, or diglycerol. In some embodiments of the bisketal of structure II, one or more $R^1$ comprises one or more isocyanate, acrylate, methacrylate, allyl, or oxirane groups. In some embodiments of the bisketal of structure II, all $R^2$ and $R^3$ are hydrogen, all $R^4$ are methyl, and all values of a equal 2.

The present invention contemplates a formulation comprising one or more bisketals of structure II. In some embodiments of the formulation comprising one or more bisketals of structure II, the formulation further comprises one or more polymers. The one or more polymers comprise, in embodiments, poly(3-hydroxybutyrate-co-3-hydroxyvalerate), poly(vinyl chloride), poly(lactic acid), or polystyrene. In some embodiments of the formulation comprising one or more bisketals of structure II, one or more bisketals is a plasticizer, a toughener, a surfactant, a barrier layer compound, a coalescing solvent, a compatibilizing agent, an interfacial modifier, or a phase transfer compound. In some embodiments of the formulation comprising one or more bisketals of structure II, the formulation is a coating formulation. In some embodiments of the formulation comprising one or more bisketals of structure II, the formulation is an adhesive formulation. In some embodiments of the formulation comprising one or more bisketals of structure II, the formulation further comprises one or more solvents. In some embodiments of the formulation comprising one or more bisketals of structure II and further comprising one or more solvents, the one or more solvents comprise two immiscible solvents and the formulation comprises a homogeneous mixture. In some embodiments of the formulation comprising one or more bisketals of structure II, the formulation further comprises one or more additives. In some embodiments of the formulation comprising one or more bisketals of structure II wherein the formulation further comprises one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof.

The present invention contemplates an article comprising the polyketal having structure II. In embodiments, the article comprising the polyketal having structure II is coated, cast, extruded, coextruded, profile extruded, blow molded, injection molded, co-injection molded, thermoformed, or reaction injection molded. In embodiments, the article comprising the polyketal having structure II comprises two or more layers and the polyketal of structure II is present in at least one layer. In embodiments, the article comprising the polyketal having structure II comprises a film, a sheet, a fiber, a foamed article, a woven fabric, a nonwoven fabric, or a pressure sensitive adhesive tape, or a paint coating.

The present invention contemplates a polymeric composition comprising one or more repeat units comprising structure III:

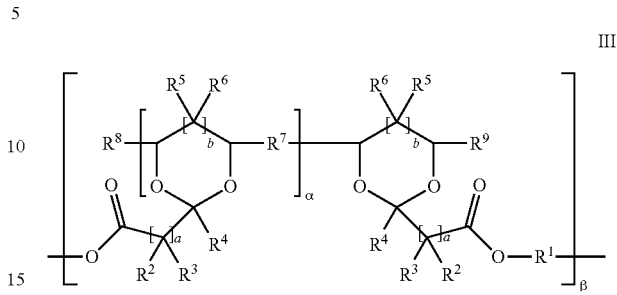

wherein $R^1$ is a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$, $R^3$, $R^4$, $R^5$, and $R^6$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ is the same or different for each occurrence;

$R^7$ is a covalent bond, methylene, ethylene, hydroxymethylene, oxygen, or —$CH_2$—O—$CH_2$— and $R^7$ is the same or different for each occurrence;

$R^8$ and $R^9$ are independently hydrogen, a linear, branched, or cyclic alkyl, a linear, branched, or cyclic alkenyl, alkynyl, aryl, alkaryl, or a polymeric moiety; and optionally contains one or more heteroatoms;

a is 0 or an integer of 1 to 12; and b is 0 or 1 wherein b=0 indicates a five membered ring,

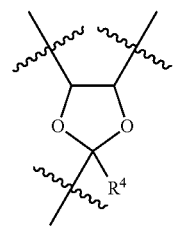

b=1 indicates a 6 membered ring,

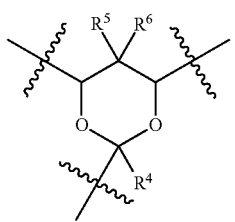

and b may be the same or different for each occurrence;

α is an integer of at least 1; and

β is an integer of at least 1.

In some embodiments of the polymeric composition having structure III, a equal 2, all $R^2$ and $R^3$ are hydrogen, and all $R^4$ are methyl. In some embodiments of the polymeric composition having structure III, all b equal 0. In embodiments of the polymeric composition having structure III, all values of b equal 1 and all $R^5$ and $R^6$ are hydrogen. In embodiments of the polymeric composition having structure III, a equals 1 or 2 and $R^8$ and $R^9$ are hydrogen. In embodiments of the polymeric composition having structure III, α equals 1 and b equals 0. In embodiments of the polyketal I, α is between about 2 and 1000, all values of b equal 1, and all $R^5$ and $R^6$ are hydrogen. In some embodiments of the polymeric composition having structure III, β is about 1. In some embodiments of the polymeric composition having structure III, β is between about 2 and 12. In some embodiments of the polymeric composition having structure III, β is between about 12 and 100. In some embodiments of the polymeric composition having structure III β is between about 100 and 1000. In some embodiments of the polymeric composition having structure III, one or more additional repeat units comprise one or more ester groups, ether groups, or a combination thereof. In some such embodiments the additional repeat units comprising one or more ester groups comprise isophthalate, terephthalate, or adipate residues. In some embodiments of the polymeric composition having structure III, one or more additional repeat units comprise urethane, (urethane urea), (ester urethane), (ester urethane urea), (ester ether urethane), or (ester ether urethane urea) groups. In some embodiments of the polymeric composition having structure III, one or more additional repeat units comprise carbonate groups. In some embodiments of the polymeric composition having structure III, one or more additional repeat units comprise the residue of one or more polymerized acrylate, methacrylate, oxirane, or allyl groups.

The present invention contemplates a formulation comprising the polymeric composition having structure III. In embodiments, the formulation comprising the polymeric composition having structure III further comprises one or more additional polymeric compounds. In embodiments, the one or more additional polymeric compounds comprise poly(3-hydroxybutyrate-co-3-hydroxyvalerate), poly(vinyl chloride), poly(lactic acid), or polystyrene. In embodiments of the formulation comprising the polymeric composition having structure III, the polymeric composition having structure III is a plasticizer, a toughener, a surfactant, a barrier layer compound, an interfacial modifier, a compatibilizer, or a phase transfer compound. In embodiments, the formulation comprising the polymeric composition having structure III further comprises one or more additives. In embodiments of the formulation comprising the polymeric composition having structure III and one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof. In embodiments, the formulation comprising the polymeric composition having structure III formulation is a coating formulation. In embodiments, the formulation comprising the polymeric composition having structure III is an adhesive formulation. In embodiments, the formulation comprising the polymeric composition having structure III, the formulation further comprises one or more solvents.

The present invention contemplates an article comprising the polymeric composition having structure III. In embodiments, the article comprising the polymeric composition having structure III is coated, cast, extruded, coextruded, profile extruded, blow molded, thermoformed, injection molded, coinjection molded, or reaction injection molded. In embodiments, the article comprising the polymeric composition having structure III comprises two or more layers and the polymeric composition of structure III is present in at least one layer. In embodiments, the article comprising the polymeric composition having structure III comprises a film, a sheet, a fiber, a foamed article, a woven fabric, a nonwoven fabric, or a pressure sensitive adhesive tape, or a paint coating.

The present invention contemplates a polymeric composition having one or more repeat units comprising structure IV:

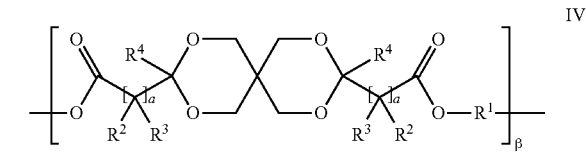

wherein
$R^1$ is a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;
$R^2$ and $R^3$ are independently hydrogen, a linear, branched, or cyclic alkyl, a linear, branched, or cyclic alkenyl, alkynyl, aryl, or alkaryl; and optionally contains one or more heteroatoms; and $R^2$ and $R^3$ are the same or different for each occurrence;
$R^4$ is a linear, branched, or cyclic alkyl, a linear, branched, or cyclic alkenyl, alkynyl, aryl, or alkaryl; and optionally contains one or more heteroatoms; and $R^4$ is the same or different for each occurrence;
a is 0 or an integer of 1 to 12; and
β is an integer of at least 1.

In some embodiments of the polymeric composition having structure IV, all a equal 2, all $R^2$ and $R^3$ are hydrogen, and all $R^4$ are methyl. In some embodiments of the polymeric composition having structure IV, β is about 1. In some embodiments of the polymeric composition having structure IV, β is between about 2 and 12. In some embodiments of the polymeric composition having structure IV, β is between about 12 and 100. In some embodiments of the polymeric composition having structure IV, β is between about 100 and 1000. In some embodiments of the polymeric composition having structure IV, one or more additional repeat units comprise one or more ester groups, ether groups, or a combination thereof. In some such embodiments the additional repeat units comprise one or more ester groups comprise isophthalate, terephthalate, or adipate residues. In some embodiments of the polymeric composition having structure IV, one or more repeat units comprise urethane, (urethane urea), (ester urethane), (ester urethane urea), (ester ether urethane), or (ester ether urethane urea) groups. In some embodiments of the polymeric composition having structure N, one or more additional repeat units comprise one or more carbonate groups. In some embodiments of the polymeric composition having structure N, one or more repeat units comprise the residue of one or more polymerized acrylate, methacrylate, oxirane, or allyl groups.

The present invention contemplates a formulation comprising the polymeric composition having structure IV. In embodiments, the formulation comprising the polymeric composition having structure IV further comprises one or more additional polymeric compounds. In embodiments, the one or more additional polymeric compounds comprise poly(3-hydroxybutyrate-co-3-hydroxyvalerate), poly(vinyl chloride), poly(lactic acid), or polystyrene. In embodiments of the formulation comprising the polymeric composition having structure IV, the polymeric composition having structure IV is a plasticizer, a toughener, a surfactant, a barrier layer compound, an interfacial modifier, a compatibilizer, or a phase transfer compound. In embodiments, the formulation comprising the polymeric composition having structure IV further comprises one or more additives. In embodiments of the formulation comprising the polymeric composition having structure IV and one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof. In embodiments, the formulation comprising the polymeric composition having structure IV formulation is a coating formulation. In embodiments, the formulation comprising the polymeric composition having structure IV is an adhesive formulation. In embodiments, the formulation comprising the polymeric composition having structure IV, the formulation further comprises one or more solvents.

The present invention contemplates an article comprising the polymeric composition having structure IV. In embodiments, the article comprising the polymeric composition having structure IV is coated, cast, extruded, coextruded, profile extruded, blow molded, thermoformed, injection molded, coinjection molded, or reaction injection molded. In embodiments, the article comprising the polymeric composition having structure IV comprises two or more layers and the polymeric composition of structure III is present in at least one layer. In embodiments, the article comprising the polymeric composition having structure III comprises a film, a sheet, a fiber, a foamed article, a woven fabric, a nonwoven fabric, or a pressure sensitive adhesive tape, or a paint coating.

The present invention contemplates a polyketal having structure V:

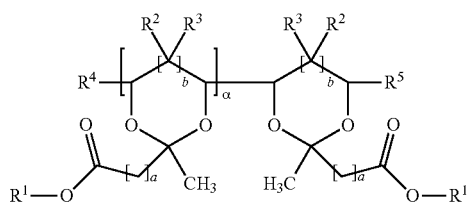

V wherein $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$ and $R^3$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ is the same or different for each occurrence;

$R^4$ and $R^5$ are independently hydrogen, a linear, branched, or cyclic alkyl, a linear, branched, or cyclic alkenyl, alkynyl, aryl, alkaryl, or a polymeric moiety; and optionally contain one or more heteroatoms;

a is 0 or an integer of 1 to 12 and a is the same or different for each occurrence;

b is 0 or 1 wherein b=0 indicates a five membered ring,

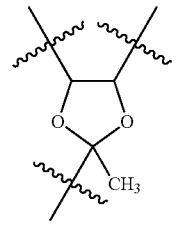 [SMILES: *C1OC(*)(C)OC1*]

b=1 indicates a 6 membered ring,

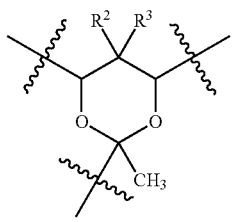

and b may be the same or different for each occurrence; and
α is an integer of at least 1.

In some embodiments of the polymeric composition having structure V, one or more $R^1$ is ethyl, butyl, or 2-ethylhexyl. In some embodiments of the polymeric composition having structure V, one or more $R^1$ is the residue of a polyol. In some embodiments of the polymeric composition having structure V wherein $R^1$ is the residue of a polyol, the polyol is ethylene glycol, diethylene glycol, pentaerythritol, 1,6-hexanediol, glycerol, or diglycerol. In some embodiments of the bisketal of structure V, one or more $R^1$ comprises one or more isocyanate, acrylate, methacrylate, allyl, or oxirane groups. In some embodiments of the polymeric composition having structure V, all values of a equal 2. In some embodiments of the polymeric composition having structure V, all values of b equal 0. In some embodiments of the polymeric composition having structure V, all values of b equal 1 and all $R^3$ and $R^4$ are hydrogen. In some embodiments of the polymeric composition having structure V, α equals 1 or 2 and $R^4$ and $R^5$ are hydrogen. In some embodiments of the polymeric composition having structure V, α is between about 2 and 1000, all values of b equal 1, and all $R^3$ and $R^4$ are hydrogen. In some such embodiments, the value of a is between about 10 and 100. In some embodiments of the polymeric composition having structure V, one or more of $R^4$ and $R^5$ are residues of a polymer. In some embodiments of the polymeric composition having structure V wherein one or more of $R^4$ and $R^5$ are residues of a polymer, the polymer is poly(vinyl alcohol), poly(vinyl acetate), polyethylene, polypropylene, or a random or block copolymer thereof.

The present invention contemplates a formulation comprising the polyketal having structure V. The formulation comprising the polyketal having structure V comprises, in embodiments, one or more polymers. The one or more polymers comprise, in embodiments, poly(3-hydroxybutyrate-co-3-hydroxyvalerate), poly(vinyl chloride), poly(lactic acid), or polystyrene. In the formulation, the polyketal having structure V is, in embodiments, a plasticizer, a toughener, a surfactant, a coalescing solvent, a compatibilizer, a barrier layer compound, an interfacial modifier, or a phase transfer compound. The formulation comprising the polyketal having structure V can further comprise one or more solvents. The one or more solvents comprise, in embodiments, two immiscible solvents, wherein the formulation comprises a homogeneous mixture. In some embodiments of the formulation comprising the polyketal having structure V and further comprising two immiscible solvents wherein the formulation comprises a homogeneous mixture, the polyketal of structure V is about 0.01 vol % to 50 vol % percent based on total volume of the one or more solvents, and the homogeneous mixture comprises between about 5 vol % to 95 vol % methanol based on the total volume of the one or more solvents. In other embodiments of the formulation comprising the polyketal having structure V and further comprising two immiscible solvents wherein the formulation comprises a homogeneous mixture, the polyketal of structure V is present at about 0.1 vol % to 20 vol % based on the total volume of the one or more solvents. In other embodiments of the formulation comprising the polyketal having structure V, further comprising two immiscible solvents wherein the formulation comprises a homogeneous mixture, the polyketal of structure V is present at about 1 vol % to 10 vol % based on the total volume of the one or more solvents. In some embodiments of the formulation comprising the polyketal having structure V and further comprising two immiscible solvents wherein the formulation comprises a homogeneous mixture, the two immiscible solvents comprise a hexane methanol blend or a methanol water blend. In some embodiments of the formulation comprising the polyketal having structure V and further comprising a hexane methanol blend or a methanol water blend, the methanol is present at about 50 vol % based on the total volume of the one or more solvents. In some embodiments of the formulation comprising the polyketal having structure V and further comprising a hexane methanol blend or a methanol water blend, $R_1$ is butyl, $R_4$ and $R_5$ are hydrogen, a is 2, b is 0, and α is 1. In embodiments, the formulation comprising the polyketal of structure V is a coating formulation. In embodiments, the formulation comprising the polyketal of structure V is an adhesive formulation.

The present invention contemplates an article comprising the polyketal having structure V. In embodiments, the article comprising the polyketal having structure V is coated, cast, extruded, coextruded, profile extruded, blow molded, injection molded, co-injection molded, thermoformed, or reaction injection molded. In embodiments, the article comprising the polyketal having structure V comprises two or more layers and the polyketal of structure V is present in at least one layer. In embodiments, the article comprising the polyketal having structure V comprises a film, a sheet, a fiber, a foamed article, a woven fabric, a nonwoven fabric, or a pressure sensitive adhesive tape, or a paint coating.

The present invention contemplates a polyketal having the structure VI:

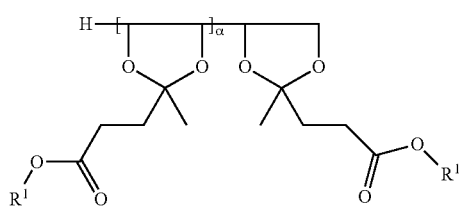

VI wherein
$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence; and
α is 1 or 2.

In embodiments of the polyketal having structure VI, one or more $R^1$ is ethyl, butyl, or 2-ethylhexyl. In embodiments of the polyketal having structure VI, one or more $R^1$ is the residue of a polyol. In embodiments of the polyketal having structure VI wherein one or more $R^1$ is the residue of a polyol, the polyol is ethylene glycol, diethylene glycol, pentaerythritol, 1,6-hexanediol, glycerol, or diglycerol. In some embodiments of the bisketal of structure VI, one or more $R^1$ comprises one or more isocyanate, acrylate, methacrylate, allyl, or oxirane groups.

The present invention contemplates a formulation comprising the polyketal having structure VI. The formulation comprising the polyketal having structure VI comprises, in embodiments, one or more polymers. The one or more polymers comprise, in embodiments, poly(3-hydroxybutyrate-co-3-hydroxyvalerate), poly(vinyl chloride), poly(lactic acid), or polystyrene. In the formulation, the polyketal having structure VI is, in embodiments, a plasticizer, a toughener, a surfactant, a coalescing solvent, a compatibilizer, a barrier layer compound, an interfacial modifier, or a phase transfer compound. The formulation comprising the polyketal having structure VI can further comprise one or more solvents. The one or more solvents comprise, in embodiments, two immiscible solvents, wherein the formulation comprises a homogeneous mixture. In some embodiments of the formulation comprising the polyketal having structure VI and further comprising two immiscible solvents wherein the formulation comprises a homogeneous mixture, the polyketal of structure VI is about 0.01 vol % to 50 vol % percent based on total volume of the one or more solvents, and the homogeneous mixture comprises between about 5 vol % to 95 vol % methanol based on the total volume of the one or more solvents. In other embodiments of the formulation comprising the polyketal having structure VI and further comprising two immiscible solvents wherein the formulation comprises a homogeneous mixture, the polyketal of structure VI is present at about 0.1 vol % to 20 vol % based on the total volume of the one or more solvents. In other embodiments of the formulation comprising the polyketal having structure VI, further comprising two immiscible solvents wherein the formulation comprises a homogeneous mixture, the polyketal of structure VI is present at about 1 vol % to 10 vol % based on the total volume of the one or more solvents. In some embodiments of the formulation comprising the polyketal having structure VI and further comprising two immiscible solvents wherein the formulation comprises a homogeneous mixture, the two immiscible solvents comprise a hexane methanol blend or a methanol water blend. In some embodiments of the formulation comprising the polyketal having structure VI and further comprising a hexane methanol blend or a methanol water blend, the methanol is present at about 50 vol % based on the total volume of the one or more solvents. In some embodiments of the formulation comprising the polyketal having structure VI and further comprising a hexane methanol blend or a methanol water blend, $R_1$ is butyl and α is 1. In embodiments, the formulation comprising the polyketal of structure VI is a coating formulation. In embodiments, the formulation comprising the polyketal of structure VI is an adhesive formulation.

The present invention contemplates an article comprising the polyketal having structure VI. In embodiments, the article comprising the polyketal having structure VI is coated, cast, extruded, coextruded, profile extruded, blow molded, injection molded, co-injection molded, thermoformed, or reaction injection molded. In embodiments, the article comprising the polyketal having structure VI comprises two or more layers and the polyketal of structure VI is present in at least one layer. In embodiments, the article comprising the polyketal having structure VI comprises a film, a sheet, a fiber, a foamed article, a woven fabric, a nonwoven fabric, or a pressure sensitive adhesive tape, or a paint coating.

The present invention contemplates a polymeric composition comprising one or more repeat units comprising structure VII:

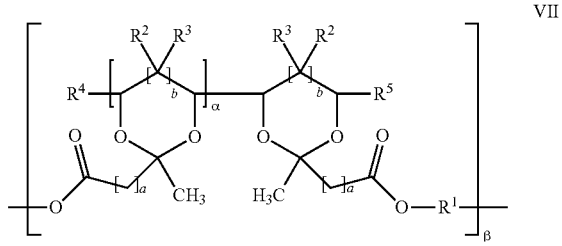

wherein $R^1$ is a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$ and $R^3$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ is the same or different for each occurrence;

$R^4$ and $R^5$ are independently hydrogen, a linear, branched, or cyclic alkyl, a linear, branched, or cyclic alkenyl, alkynyl, aryl, alkaryl, or a polymeric moiety; and optionally contain one or more heteroatoms;

a is 0 or an integer of 1 to 12 and a is the same or different for each occurrence;

b is 0 or 1 wherein b=0 indicates a five membered ring,

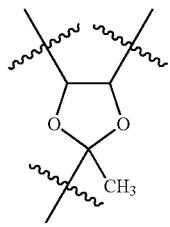 [SMILES: *C1OC(*)(C)OC1*]

b=1 indicates a 6 membered ring,

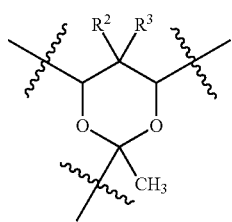

and b may be the same or different for each occurrence; and

α is an integer of at least 1; and

β is an integer of at least 1.

In embodiments of the polymeric composition comprising one or more repeat units comprising structure VII, all a equal 2. In embodiments of the polymeric composition comprising one or more repeat units comprising structure VII, all b equal 0.

In some embodiments of the polymeric composition having structure VII, all values of b equal 1 and all $R^3$ and $R^4$ are hydrogen. In some embodiments of the polymeric composition having structure VII, α equals 1 or 2 and $R^4$ and $R^5$ are hydrogen. In some embodiments of the polymeric composition having structure VII, α is between about 2 and 1000, all values of b equal 1, and all $R^3$ and $R^4$ are hydrogen. In some such embodiments, the value of α is between about 10 and 100. In some embodiments of the polymeric composition having structure VII, one or more of $R^4$ and $R^5$ are residues of a polymer. In some embodiments of the polymeric composition having structure VII wherein one or more of $R^4$ and $R^5$ are residues of a polymer, the polymer is poly(vinyl alcohol), poly(vinyl acetate), polyethylene, polypropylene, or a random or block copolymer thereof. In embodiments of the polymeric composition comprising one or more repeat units comprising structure VII, one or more additional repeat units comprise one or more ester groups, ether groups, or a combination thereof. In some such embodiments the additional repeat units comprise one or more ester groups comprise isophthalate, terephthalate, or adipate residues. In embodiments of the polymeric composition comprising one or more repeat units comprising structure VII, one or more additional repeat units comprise urethane, (urethane urea), (ester urethane), (ester urethane urea), (ester ether urethane), or (ester ether urethane urea) groups. In embodiments of the polymeric composition comprising one or more repeat units comprising structure VII, one or more additional repeat units comprise a carbonate group. In embodiments of the polymeric composition comprising one or more repeat units comprising structure VII, one or more repeat units comprise a polymerized residue of an acrylate, methacrylate, oxirane, or allyl group.

The present invention contemplates a formulation comprising the polyketal having structure VII. In embodiments, the formulation comprising the polyketal having structure VII further comprises one or more additional polymeric compounds. In embodiments, the formulation comprising the polyketal having structure VII and one or more additional polymeric compounds, the one or more additional polymeric compounds comprise poly(3-hydroxybutyrate-co-3-hydroxyvalerate), poly(vinyl chloride), poly(lactic acid), or polystyrene. In embodiments of the formulation comprising the polyketal having structure VII, the polyketal having structure VII is a plasticizer, a toughener, a surfactant, a barrier layer compound, an interfacial modifier, a compatibilizer, or a phase transfer compound. In embodiments, the formulation comprising the polyketal having structure VII further comprises one or more additives. In embodiments, the formulation comprising the polyketal having structure VII and one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof. In embodiments, the formulation comprising the polyketal having structure VII is a coating formulation. In embodiments, the formulation comprising the polyketal having structure VII is an adhesive formulation. In embodiments, the formulation comprising the polyketal having structure VII further comprises one or more solvents.

The present invention contemplates an article comprising the polyketal having structure VII. In embodiments, the article comprising the polyketal having structure VII is coated, cast, extruded, coextruded, profile extruded, blow molded, injection molded, co-injection molded, thermoformed, or reaction injection molded. In embodiments, the article comprising the polyketal having structure VII comprises two or more layers and the polyketal of structure VII is present in at least one layer. In embodiments, the article comprising the polyketal having structure VII comprises a film, a sheet, a fiber, a foamed article, a woven fabric, a nonwoven fabric, or a pressure sensitive adhesive tape, or a paint coating.

The present invention contemplates a polymeric composition comprising one or more repeat units comprising structure VIII:

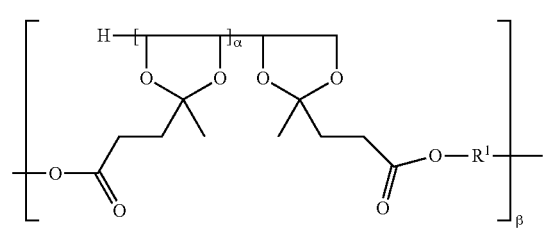

wherein $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

α is 1 or 2; and

β is an integer of at least 1.

In embodiments of the polymeric composition having structure VIII, α is 1. In embodiments of the polymeric composition having structure VIII, β is about 1. In embodiments of the polymeric composition having structure VIII, β is between about 2 and 12. In embodiments of the polymeric composition having structure VIII, β is between about 12 and 100. In embodiments of the polymeric composition having structure VIII, β is between about 100 and 1000. In embodiments, the polymeric composition having structure VIII comprises one or more additional repeat units comprising one or more ester groups, ether groups, or a combination thereof. In some such embodiments the additional repeat units comprise one or more ester groups comprise isophthalate, terephthalate, or adipate residues. In embodiments, the polymeric composition having structure VIII comprises one or more repeat units comprising urethane, (urethane urea), (ester urethane), (ester urethane urea), (ester ether urethane), or (ester ether urethane urea) groups. In embodiments, the polymeric composition having structure VIII comprises one or more repeat units comprising carbonate groups. In embodiments, the polymeric composition having structure VIII comprises a polymerized residue of an acrylate, methacrylate, oxirane, or allyl group.

The present invention contemplates a formulation comprising one or more polymeric compositions having structure VIII. In embodiments of the formulation comprising one or more compositions having structure VIII the formulation further comprises one or more additional polymeric compounds. In embodiments of the formulation comprising one or more compositions having structure VIII and further comprising one or more additional polymeric compounds, the one or more additional polymeric compounds comprise poly(3-hydroxybutyrate-co-3-hydroxyvalerate), poly(vinyl chloride), poly(lactic acid), or polystyrene. In embodiments of the formulation comprising one or more compositions having structure VIII, the one or more polymeric compositions is a plasticizer, a toughener, a surfactant, a barrier layer compound, an interfacial modifier, a compatibilizer, or a phase transfer compound. In embodiments of the formulation comprising one or more compositions having structure VIII, the formulation further comprises one or more additives. In embodiments of the formulation comprising one or more compositions having structure VIII and further comprising one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof. In embodiments of the formulation comprising one or more compositions having structure VIII, the formulation is a coating formulation. In embodiments of the formulation comprising one or more compositions having structure VIII, the formulation is an adhesive formulation. In embodiments of the formulation comprising one or more compositions having structure VIII, the formulation further comprises one or more solvents.

The present invention contemplates an article comprising the polyketal having structure VIII. In embodiments, the article comprising the polyketal having structure VIII is coated, cast, extruded, coextruded, profile extruded, blow molded, injection molded, co-injection molded, thermoformed, or reaction injection molded. In embodiments, the article comprising the polyketal having structure VIII comprises two or more layers and the polyketal of structure VIII is present in at least one layer. In embodiments, the article comprising the polyketal having structure VIII comprises a film, a sheet, a fiber, a foamed article, a woven fabric, a nonwoven fabric, or a pressure sensitive adhesive tape, or a paint coating.

The present invention contemplates a bisketal having structure IX:

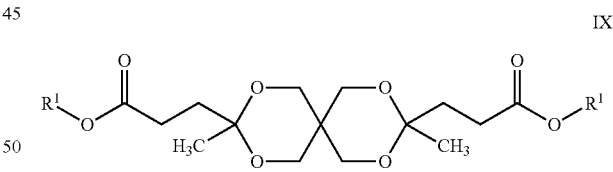

wherein $R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence. In some embodiments of the bisketal of structure IX, one or more $R^1$ is ethyl, butyl, or 2-ethylhexyl. In some embodiments of the bisketal of structure IX, one or more $R^1$ is the residue of a polyol. In some embodiments of the bisketal of structure IX wherein one or more $R^1$ is the residue of a polyol, the one or more polyol is ethylene glycol, diethylene glycol, pentaerythritol, 1,6-hexanediol, glycerol, or diglycerol. In some embodiments of the bisketal of structure IX, one or more $R^1$ comprises one or more isocyanate, acrylate, methacrylate, allyl, or oxirane groups.

The present invention contemplates a formulation comprising one or more bisketals of structure IX. In some embodiments of the formulation comprising one or more bisketals of structure IX, the formulation further comprises one or more polymers. The one or more polymers comprise, in embodiments, poly(3-hydroxybutyrate-co-3-hydroxyvalerate), poly(vinyl chloride), poly(lactic acid), or polystyrene. In some embodiments of the formulation comprising one or more bisketals of structure IX, one or more bisketals is a plasticizer, a toughener, a surfactant, a barrier layer compound, a coalescing solvent, a compatibilizing agent, an interfacial modifier, or a phase transfer compound. In some embodiments of the formulation comprising one or more bisketals of structure IX, the formulation is a coating formulation. In some embodiments of the formulation comprising one or more bisketals of structure IX, the formulation is an adhesive formulation. In some embodiments of the formulation comprising one or more bisketals of structure IX, the formulation further comprises one or more solvents. In some embodiments of the formulation comprising one or more bisketals of structure IX and further comprising one or more solvents, the one or more solvents comprise two immiscible solvents and the formulation comprises a homogeneous mixture. In some embodiments of the formulation comprising one or more bisketals of structure IX, the formulation further comprises one or more additives. In some embodiments of the formulation comprising one or more bisketals of structure IX wherein the formulation further comprises one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof.

The present invention contemplates an article comprising the polyketal having structure IX. In embodiments, the article comprising the polyketal having structure IX is coated, cast, extruded, coextruded, profile extruded, blow molded, injection molded, co-injection molded, thermoformed, or reaction injection molded. In embodiments, the article comprising the polyketal having structure IX comprises two or more layers and the polyketal of structure IX is present in at least one layer. In embodiments, the article comprising the polyketal having structure IX comprises a film, a sheet, a fiber, a foamed article, a woven fabric, a nonwoven fabric, or a pressure sensitive adhesive tape, or a paint coating.

The present invention contemplates a polymeric composition having one or more repeat units comprising structure X:

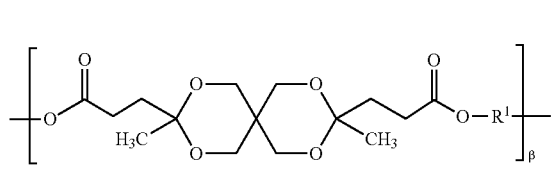

wherein $R^1$ is a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence, and β is an integer of at least 1. In embodiments of the polymeric composition having structure X, β is about 1. In embodiments of the polymeric composition having structure X, β is between about 2 and 12. In embodiments of the polymeric composition having structure X, β is between about 12 and 100. In embodiments of the polymeric composition having structure X, β is between about 100 and 1000. In embodiments, the polymeric composition having structure X comprises one or more additional repeat units comprising one or more ester groups, ether groups, or a combination thereof. In some such embodiments the additional repeat units comprise one or more ester groups comprise isophthalate, terephthalate, or adipate residues. In some embodiments of the polymeric composition having structure X, one or more repeat units comprise urethane, (urethane urea), (ester urethane), (ester urethane urea), (ester ether urethane), or (ester ether urethane urea) groups. In some embodiments of the polymeric composition having structure X, one or more additional repeat units comprise one or more carbonate groups. In some embodiments of the polymeric composition having structure X, one or more repeat units comprise the residue of one or more polymerized acrylate, methacrylate, oxirane, or allyl groups.

The present invention contemplates a formulation comprising the polymeric composition having structure X. In embodiments, the formulation comprising the polymeric composition having structure X further comprises one or more additional polymeric compounds. In embodiments, the one or more additional polymeric compounds comprise poly(3-hydroxybutyrate-co-3-hydroxyvalerate), poly(vinyl chloride), poly(lactic acid), or polystyrene. In embodiments of the formulation comprising the polymeric composition having structure X, the polymeric composition having structure X is a plasticizer, a toughener, a surfactant, a barrier layer compound, an interfacial modifier, a compatibilizer, or a phase transfer compound. In embodiments, the formulation comprising the polymeric composition having structure X further comprises one or more additives. In embodiments of the formulation comprising the polymeric composition having structure X and one or more additives, the one or more additives comprise one or more crosslinkers, redox initiators, thermal initiators, UV initiators, UV stabilizers, colorants, thermal stabilizers, antibacterial agents, antifungal agents, antioxidants, plasticizers, fillers, adjuvants, or a mixture thereof. In embodiments, the formulation comprising the polymeric composition having structure X formulation is a coating formulation. In embodiments, the formulation comprising the polymeric composition having structure X is an adhesive formulation. In embodiments, the formulation comprising the polymeric composition having structure X, the formulation further comprises one or more solvents.

The present invention contemplates an article comprising the polymeric composition having structure X. In embodiments, the article comprising the polymeric composition having structure X is coated, cast, extruded, coextruded, profile extruded, blow molded, thermoformed, injection molded, coinjection molded, or reaction injection molded. In embodiments, the article comprising the polymeric composition having structure X comprises two or more layers and the polymeric composition of structure III is present in at least one layer. In embodiments, the article comprising the polymeric composition having structure III comprises a film, a sheet, a fiber, a foamed article, a woven fabric, a nonwoven fabric, or a pressure sensitive adhesive tape, or a paint coating.

EXPERIMENTAL SECTION

General Laboratory Procedures

Gas Chromatography (GC) and GC-Mass Spectrometry (GC-MS) Analyses

GC and GC-MS analyses are carried out according to standard laboratory techniques. Standard GC analysis is carried out by flame ionization detector. The integration peak areas of all peaks in the chromatogram are automatically calculated by an Agilent Technologies ChemStation (Agilent Technologies of Santa Clara, Calif.). The calculated peak areas are reported as a weighted percent (expressed as abundance) relative to the area of all of the detected peaks in the chromatogram (total area). These calculations are used elsewhere herein to report all percent yield, percent yield "based on theoretical", percent yield "as determined by GC", percent yield "as determined by GC-MS", and any other percent reaction statements resulting from GC or GC-MS analyses.

Gel Permeation Chromatography (GPC)

Molecular weight determination is carried out by GPC using a Waters Isocratic HPLC System (from Waters Corp. of Milford, Mass.) that includes a Waters 2414 Differential Refractometer, Waters 1515 Isocratic Pump, Waters 717 Autosampler, and Waters Column Heater and Empower GPC Software for molecular weight analysis. For samples with an expected molecular weight of 20,000-400,000 Daltons a PLgel Mixed D 5 μm column, 300×7.5 mm, is used; for samples with an expected molecular weight of less than 20,000 a PLgel Mixed E 5 μm column, 300×7.5 mm, is used; and for samples with an expected molecular weight between 20,000 and 2,000,000 a PLgel Mixed C 5 μm column, 300×7.5 mm is used. All columns were obtained from Polymer Labs, a division of Varian Inc. of Palo Alto, Calif. THF mobile phase is employed at 1 ml/min and weight average molecular weight ($M_w$) is calculated against polystyrene narrow molecular weight standards.

Differential Scanning Calorimetry (DSC)

1. Determination of Glass Transition Temperature ($T_g$)

Glass transition temperature is determined by following ASTM D-3418, employing a TA Q200 instrument with refrigerated cooling and TA Thermal Advantage software (from TA Instruments of New Castle, Del.). Homogeneous samples of between about 5 and 15 mg are prepared, weighed, placed in a Tzero pan and crimped with a Tzero lid, (pan and lid both available from TA Instruments). The mass of the sample is entered into the Thermal Advantage software. The thermal analysis is carried out according to one of the three sets of parameters below:

Parameter Set 1
Cycle 0: Equilibrate at −80° C.
Isotherm for 2.00 minutes
End of Cycle 0
Cycle 1: Ramp 10° C./min to 150° C.
Isotherm for 2.00 minutes
End of Cycle 1
Cycle 2: Ramp 10° C./min to −80° C.
Isotherm for 2.00 minutes
End of Cycle 2
Cycle 3: Ramp 10° C./min to 150° C.
Isotherm for 2.00 minutes
End of Cycle 3
Repeat at Cycle 0
Parameter Set 2
Cycle 0: Equilibrate at −150° C.
Isotherm for 5.00 minutes
End of Cycle 0
Cycle 1: Ramp 10° C./min to 150° C.
Isotherm for 5.00 minutes
End of Cycle 1
Cycle 2: Ramp 10° C./min to −150° C.
Isotherm for 5.00 minutes
End of Cycle 2
Cycle 3: Ramp 10° C./min to 150° C.
Isotherm for 5.00 minutes
End of Cycle 3
Repeat at Cycle 0
Parameter Set 3
Cycle 0: Equilibrate at −40° C.
Isotherm for 2.00 minutes
End of Cycle 0
Cycle 1: Ramp 10° C./min to 240° C.
Isotherm for 2.00 minutes
End of Cycle 1
Cycle 2: Ramp 10° C./min to −40° C.
Isotherm for 2.00 minutes
End of Cycle 2
Cycle 3: Ramp 10° C./min to 240° C.
Isotherm for 2.00 minutes
End of Cycle 3
Repeat at Cycle 0

2. Determination of Degradation Temperature

Degradation temperatures are determined using DSC according to ASTM E698-05.

Rheological Characterization

The viscosity of a material is determined by Brookfield viscometry, using a Brookfield DV2+Pro viscometer (available from the Brookfield Engineering Laboratories of Middleborough, Mass.). The appropriate spindle is chosen dependent on sample viscosity. Samples are analyzed at 25° C. unless a different temperature is stated.

Hydroxyl Number

Hydroxyl numbers are determined according to ASTM E1899-02.

Thermogravimetric Analysis (TGA)

TGA is conducted utilizing a TA Q50 with TA Thermal Advantage software (from TA Instruments of New Castle, Del.). A homogeneous sample weighing approximately 30 milligrams is placed into the TGA platinum sample pan. Samples are analyzed under a nitrogen atmosphere. The TGA temperature profile is listed below:

Equilibrate at 30° C.
Ramp 10° C./min to 800° C.

Dynamic Mechanical Analysis (DMA)

DMA is conducted utilizing a TA Q800 with liquid nitrogen cooling with TA Thermal Advantage software (from TA Instruments of New Castle, Del.). A uniform sample is prepared to fit the appropriate sample mounting clamp (extension, dual cantilever, compression, etc.). The appropriate sample dimensions are measured and entered into the Thermal Advantage software. Typical experimental run conditions are listed below:

Strain 0.1%
Frequency 1 Hz
Force Track 125%
Cycle:
Equilibrate at −100° C.
Isotherm for 5 min.
Ramp 3° C./min to 200° C.

Specific Gravity

Specific gravity is determined by the "weight per gallon" technique (ASTM D1475-98). A Gardner ASTM weight per gallon cup (83.2 mL) is first weighed. The cup is then filled with the sample and reweighed. The weight of the sample is determined by subtracting the cup weight from the [sample+cup] weight. The sample weight is then multiplied by 0.01202 to obtain the specific gravity.

Refractive Index

Refractive index is measured by placing several drops of the material to be tested on the refracting prism surface of a WYA Refractometer (obtained from Sun Instruments of Torrence, Calif.) and then closed by locking the light entrance prism. The refractive index was read once cross-hair was centered by adjusting the refractometer knob. The temperature of the refractometer was maintained at 25° C. during measurement by a circulating chiller.

Compounding

Compounding of commercially available polymeric materials is carried out using a variety of mixing equipment. Mixtures are formed using one of the following procedures.

1. HAAKE MiniLab II (from Thermo Scientific of Waltham, Mass.)

The experimental compound and selected polymer are pre-mixed by hand after weighing components into a vessel. The screws of the compounder are set to co-rotate at 150 rpm. The system is set under a continual nitrogen purge. Temperature settings are varied depending on the polymer that is being extruded, as indicated below. The material is fed into the compounder using either a manual feed (column and hand-held piston) or a pneumatic automatic feed. Blending time for the samples is between 10-15 minutes, with 10 minute runs being the most common.

Poly(vinyl chloride), $M_n$=55,000, $M_w$=97,000 from the Sigma Aldrich Company of St. Louis, Mo.: 165-170° C.

Poly(hydroxybutyrate-co-hydroxyvalerate) from Tianan Biologic of Zhejiang Province, China: 165° C.

Polystyrene from Entec Polymers of Orlando, Fla.: 180° C.

Polylactic acid from NatureWorks of Minnetonka, Minn.: 200° C.

2. HAAKE PolyLab (from Thermo Scientific of Waltham, Mass.)

The experimental compound and selected polymer are pre-mixed by hand (approximately 50 g batches) after weighing components into a vessel. Temperature settings in the compounder are varied depending on the polymer being compounded; for example, PVC is compounded at temperatures ranging between about 150° C. and 170° C. depending on blend composition. Lower mass loadings are sometimes run at a higher temperature. The screws are set to co-rotate at 100 rpm. The pre-mixed material is fed into the compounder via a gravity feed system. After adding all the material to the compounder, the system is set under a continual nitrogen purge. Blending time in the compounder is generally about 10 minutes at which time the screws are stopped and the material is removed from the mixer.

3. Daca Microcompounder (from Daca Instruments of Santa Barbara, Calif.)

The experimental compound and selected polymer are pre-mixed by hand (approximately 5 g batches) after weighing components into a vessel. The compounder is preheated to the set temperature and screws are set to co-rotate at 100 rpm. Temperature settings are varied depending on the polymer being extruded. For example, PVC is compounded at temperatures ranging between about 150° C. to 170° C. depending on blend composition. Lower mass loadings are sometimes run at a higher temperature. The pre-mixed material is fed manually into the compounder through the sample chamber via a hand-held piston. After adding all material to the compounder the system is set under a continual nitrogen purge. Blending time for the samples is generally about 10 minutes, followed by an additional 10 minutes to form an extruded rod from the blended sample.

Example 1

A 500 ml 3-neck round bottom flask was charged with 36.64 g (0.3 mol) erythritol (obtained from the Cargill Company of Wayzata, Minn.) and 346.01 g (2.4 mol) ethyl levulinate (obtained from the Sigma Aldrich Company of St. Louis, Mo.). The flask was equipped with a Dean Stark trap, mechanical stirrer, and thermocouple. The contents of the flask were heated to 80° C., at which point 15.99 µl of concentrated sulfuric acid (obtained from the Sigma Aldrich Company) was added to the reaction flask via a metered microliter pipette. A vacuum was applied to the reaction flask, slowly bringing the pressure down to 40 torr. This pressure was maintained with stirring while liquid was observed to collect in the Dean Stark trap. About 1 hour, 45 minutes after addition of sulfuric acid, the vacuum was released and a small sample was removed from the reaction flask. The vacuum was then reestablished. After an additional 1 hour, 15 minutes reaction time, liquid had stopped collecting in the Dean Stark trap. The vacuum was released, and the contents of the flask were allowed to cool to ambient temperature. A second sample was removed from the reaction flask.

Figure 2A:
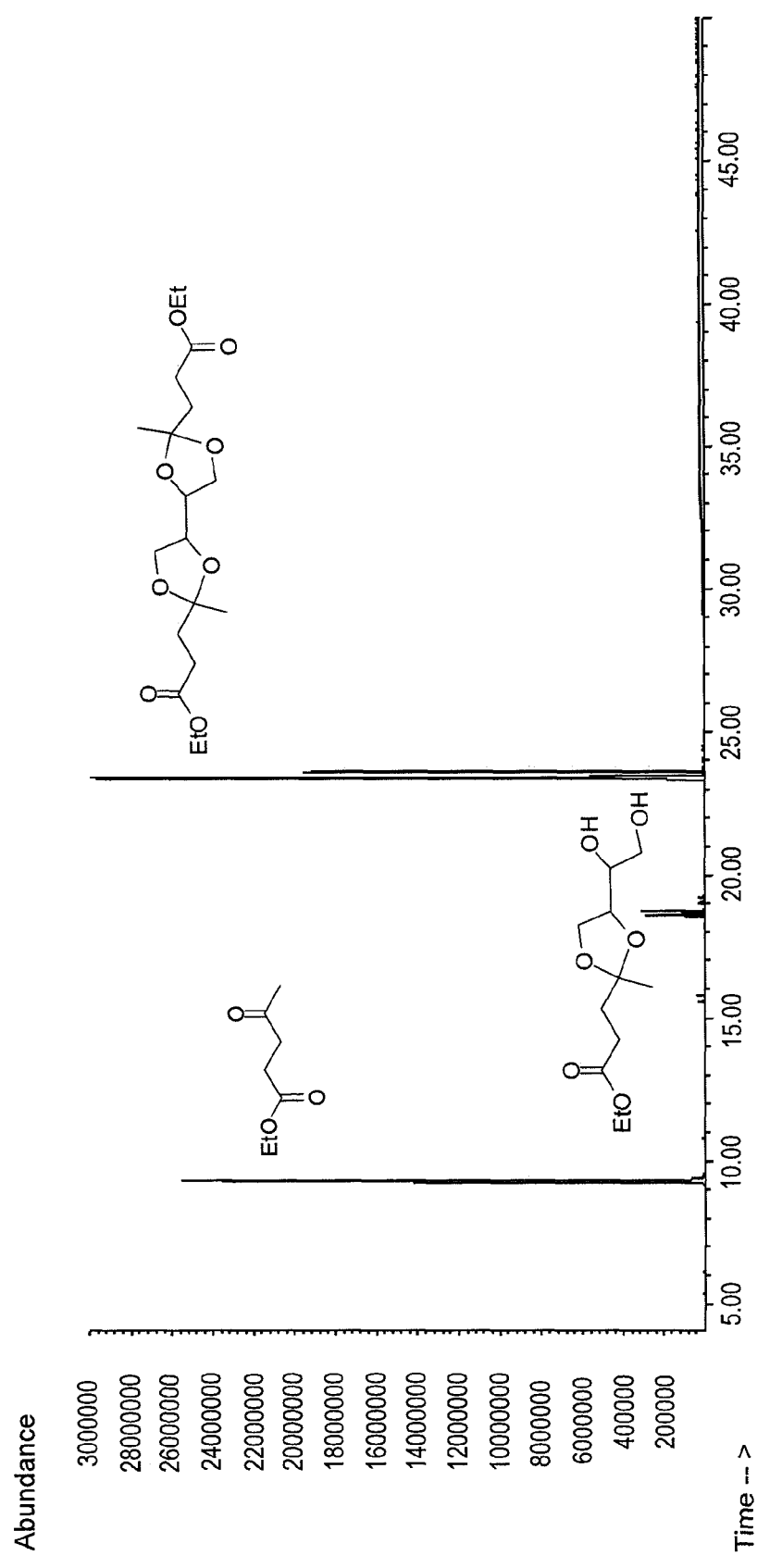
FIG. 2A-2B shows gas chromatographs of a reaction according to the invention.
Figure 2B:
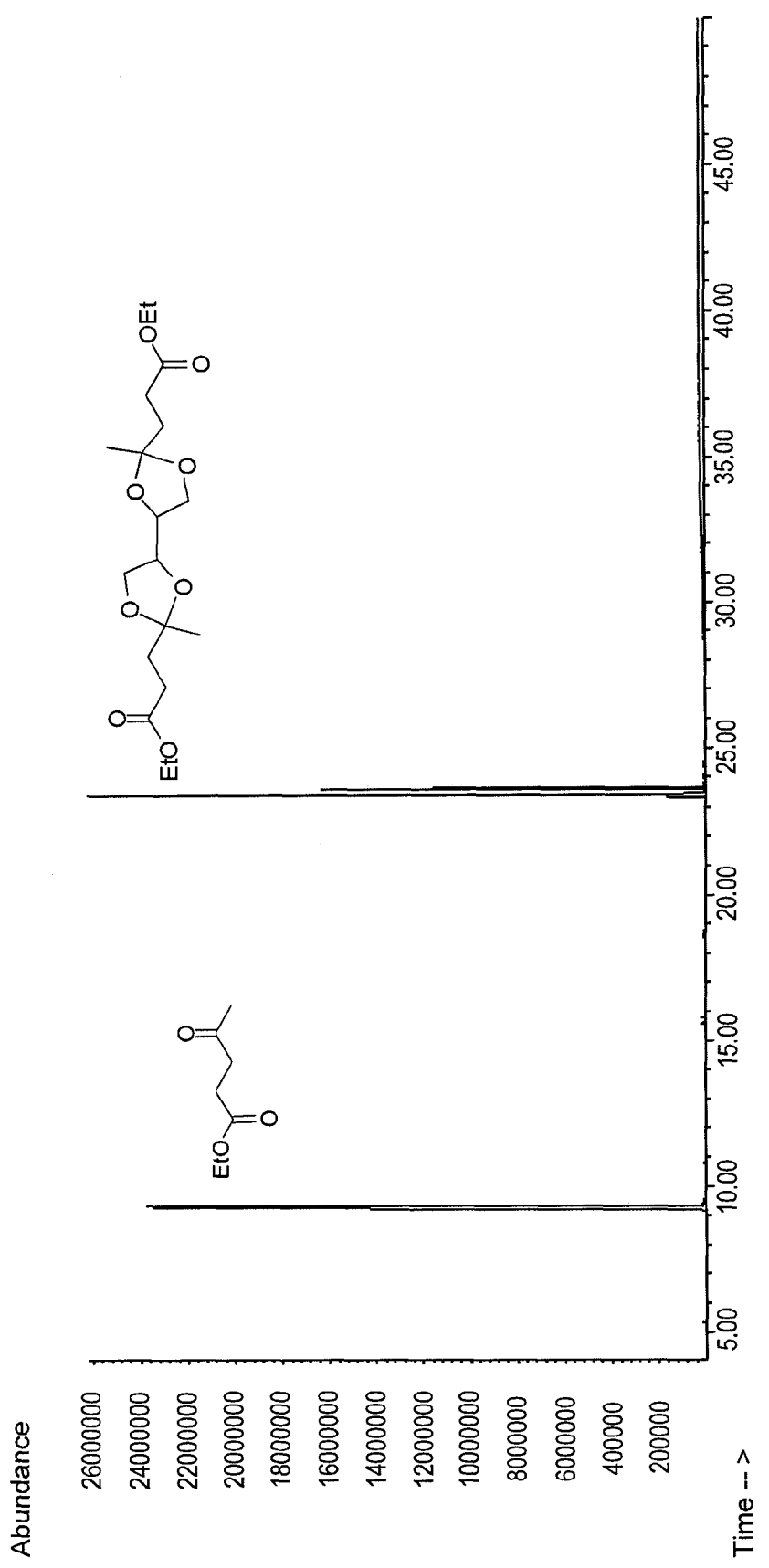

Both samples removed were analyzed by GC-MS. The GC portions of the analyses are shown in FIGS. 2A and 2B. FIG. 2A shows the GC of the sample removed after the initial 1 hour, 45 minutes of reaction time. FIG. 2B shows the GC of the sample removed after a total of 3 hours reaction time, or an additional 1 hour, 15 minutes after the first sample was taken. The percentages of products were calculated by disregarding the presence of ethyl levulinate, because of the excess molar equivalents of ethyl levulinate used in the reaction. Thus, the percentages of erythritol, the monoketal of erythritol with one molar equivalent of ethyl levulinate, and the bisketal of erythritol with two molar equivalents of ethyl levulinate were calculated by determination of their relative GC peak areas. The sample removed at 1 hour, 45 minutes was found to contain 93.03% of the bisketal, 6.97% of the monoketal, and 0% erythritol by GC peak area. The sample removed after the additional 1 hour, 15 minutes reaction time was found to contain 100% of the bisketal.

Examples 2-11

Using the procedure of Example 1, various polyketal compounds were synthesized. Table 1 shows reagents, temperature, and time of reaction as well as the percent yield of products obtained at the end of the reaction, as determined by GC-MS (GC peak area) employing the calculation described in Example 1. Unless noted, the pressure of the reaction vessel was 30 torr during the reaction.

Butyl levulinate was obtained from the Sigma Aldrich Company of St. Louis, Mo. Ethyl acetoacetate was obtained from Acros Organics of Geel, Belgium. Sorbitol was obtained from Acros Organics. Mannitol was obtained from the Sigma Aldrich Company. Pentaerythritol was obtained from the Sigma Aldrich Company. Diglycerol was obtained from Tokyo Kasei Kogyo of Tokyo, Japan. Sulfamic acid was obtained from the Sigma Aldrich Company. Amberlyst®-15 was obtained from the Rohm and Haas Company of Philadelphia, Pa.

TABLE 1

Synthetic conditions for polyketals and analysis of same.

| Expt. No. | Oxocarboxylate, g (mol) | Polyol, g (mol) | Catalyst, unit (mol) | Temp., °C. | Time, min. | Product, % by GC peak area |
|---|---|---|---|---|---|---|
| 2 | ethyl levulinate 951.52 (6.6) | erythritol 146.54 (1.2) | conc. $H_2SO_4$ 0.352 ml ($6.6 \times 10^{-4}$) | 90 | 240 | erythritol: 0 monoketal: 2.46 bisketal: 97.54 |
| 3 | ethyl levulinate 346.01 (2.4) | sorbitol 54.65 (0.3) | conc. $H_2SO_4$ 0.016 ml ($3 \times 10^{-4}$) | 105 | 480 | sorbitol: 0 monoketal: 0 bisketal: 0 trisketal: 100 |
| 4 | ethyl levulinate 346.01 (2.4) | mannitol 54.65 (0.3) | conc. $H_2SO_4$ 0.016 ml ($3 \times 10^{-4}$) | 105 | 480 | mannitol: 0 monoketal: 0 bisketal: 0 trisketal: 100 |
| 5 | butyl levulinate 947.21 (5.5) | erythritol 122.12 (1.0) | conc. $H_2SO_4$ 0.0293 ml ($5.5 \times 10^{-4}$) | 120 | 240 | erythritol: 0 monoketal: 1.00 bisketal: 99.00 |
| 6 | butyl levulinate 1205.58 (7) | sorbitol 182.17 (1) | conc. $H_2SO_4$ 0.053 ml (0.001) | 120 | 240 | sorbitol: 0 monoketal: 0 bisketal: 0 trisketal: 100 |
| 7 | ethyl levulinate 158.59 (1.1) | pentaerythritol 27.23 (0.2) | conc. $H_2SO_4$ 0.0293 ml ($5.5 \times 10^{-4}$) | 120 | 240 | erythritol: 0 monoketal: 0 bisketal: 100 |
| 8 | ethyl levulinate 237.88 (1.65) | diglycerol 49.85 (0.3) | conc. $H_2SO_4$ 0.0088 ml ($1.65 \times 10^{-4}$) | 90 | 480 | diglycerol: 0 monoketal: 0 bisketal: 100 |
| 9 | ethyl levulinate 237.88 (1.65) | erythritol 36.64 (0.3) | sulfamic acid 0.16 g ($1.65 \times 10^{-4}$) | 90 | 480 | erythritol: 0 monoketal: 0 bisketal: 100 |
| 10 | ethyl levulinate 237.88 (1.65) | erythritol 36.64 (0.3) | Amberlyst 15 (dry), 0.234 g ($5.5 \times 10^{-4}$)[(1)] | 90 | 480 | erythritol: 0 monoketal: 1.00 bisketal: 99.00 |
| 11[(2)] | ethyl acetoacetate 214.73 g (1.65) | erythritol 36.64 (0.3) | conc. $H_2SO_4$ 0.0088 ml ($1.65 \times 10^{-4}$) | 80 | 480 | erythritol: 0 monoketal: 0 bisketal: 100 |

[(1)]Molar equivalents of $H^+$
[(2)]Pressure of the reaction vessel was 100 torr.

Examples 12-15

An 896 g sample of the polyketal made according to Example 3 was added to the addition flask of a short path wiped film evaporator equipped with carbon blades. A vacuum was applied to the apparatus until the pressure in the apparatus reached 100 millitorr. While under vacuum the entire apparatus was heated to 150° C. The wiped film column blades were rotated at 70% at the maximum rate available on the apparatus. The cold finger of the wiped film apparatus was adjusted to 0° C. using a refrigerated chiller. Upon reaching the target temperature the contents of the reaction flask were dripped into the wiped film column at a rate of 160 drops/minute. After 3 hours, 15 minutes the contents of the addition flask had been emptied into the column. The non-distilled residue that was captured was analyzed by GPC, GC-MS, and $^1$H NMR.

Using the same procedure, the compounds according to Examples 1, 5, and 6 were purified and analyzed. The results of subsequent analyses are shown in Table 2.

TABLE 2

Compounds purified and analysis of purified products by GPC, GC-MS, and $^1$H NMR.

| Example No. | Polyketal, Example No. | % Polyketal, GPC | % Polyketal, GC-MS | % Polyketal, $^1$H NMR |
|---|---|---|---|---|
| 12 | 1 | 100 | 99.70 | 98.7 |
| 13 | 3 | 100 | 99.90 | 99.39 |
| 14 | 5 | 100 | 99.90 | 99.4 |
| 15 | 6 | 100 | 99.80 | 98.8 |

Example 16

A 250 ml, 3-neck round bottom flask connected with a Dean Stark trap was charged with 20.0 g (0.053 mol) of the compound made according to Example 2 and 42.42 g (0.32 mol) of 2-ethyl-1-hexanol (obtained from Acros Organics of Morris Plains, N.J.) A homogeneous solution formed upon mixing. To the mixture was added 0.42 g (0.0062 mol) of sodium ethoxide (obtained from the Acros Organics). The flask was then heated using a heating mantle. When the temperature of the contents of the flask reached 138° C. the contents were observed to start bubbling. After bubbling commenced, the temperature of the flask contents was slowly observed to reach 160° C., at which point the bubbling rate decreased. When bubbling stopped altogether, the temperature of the flask contents was increased to 175° C. Additional bubbling in the contents of the reaction flask was observed while the temperature was being raised. When the contents of the reaction flask reached 175° C. the bubbling stopped.

About 5.7 ml of liquid was observed in the Dean Stark trap at the point where no further bubbling was observed. The contents of the flask were allowed to cool to room temperature. The total reaction time from the point of the initial heating was 2 hours 10 minutes. After the contents of the flask reached room temperature they were filtered through using a KIMAX® Buchner fritted glass funnel with medium porosity (10-15 microns) (available from Gerresheimer Glass Inc. of Vineland, N.J.), and 1.0 g of monobasic potassium phosphate (obtained from Sigma Aldrich of St. Louis, Mo.) was added to the filtered contents of the reaction flask in an Erlenmeyer flask. This mixture was stirred overnight at room temperature. The contents of the flask were filtered again using a KIMAX® Buchner funnel with medium porosity (10-15 μm), and the filtrate was analyzed by GC-MS. The GC-MS showed that the transesterification was 96% complete.

The contents of the reaction flask were placed in a 250 ml single neck round bottom flask and mounted onto a rotary evaporator. The rotary evaporator was operated at 3.8 torr, at a bath temperature of 160° C., for about 30 minutes. The resulting material was again analyzed by GC-MS, which showed that substantially all of the excess 2-ethyl-1-hexanol was stripped from the contents of the flask.

Example 17

Using the technique employed in Example 16, 28.01 g (0.05 mol) of the compound synthesized according to Example 3, 58.49 g (0.45 mol) of 2-ethyl-1-hexanol and 0.58 g (0.0085 mol) of sodium ethoxide were reacted. Initial bubbling of the contents was observed to occur at about 136° C. and the reaction temperature at the end of the reaction was 174° C. GC-MS of the reacted contents of the flask showed that the reaction was 100% ethylhexyl ester of tris levulinate-sorbitol ketal.

Example 18

The refractive index, density, and viscosity at room temperature of polyketal materials were measured. The results of these measurements are shown in Table 3. The values obtained were compared to that of dioctyl phthalate (DOP) obtained from the Sigma Aldrich Company of St. Louis, Mo.

TABLE 3

Physical properties of polyketals.

| Properties | DOP | Polyketal of Example No. | | | | |
|---|---|---|---|---|---|---|
| | | 2 | 5 | 16 | 6 | 3 |
| Refractive index (25° C.) | 1.4866 | 1.456 | 1.456 | 1.4593 | 1.4646 | 1.4644 |
| Density (g/ml) | 0.981 | 1.123 | 1.079 | 1.035 | 1.211 | 1.034 |
| Viscosity (cp) | 54.1 | 83 | 76 | 136 | 1363 | 710 |

Examples 19-41

Various polyketals and DOP (dioctyl phthalate) were compounded with polyvinyl chloride (PVC) of number average molecular weight ($M_n$) 55,000, weight average molecular weight ($M_w$) 97,000 (obtained from the Sigma Aldrich Company of St. Louis, Mo.). First, a stabilized PVC mixture was formed by admixing 66.5 g of the polyvinyl chloride, 2.5 g of Vikoflex 7170 epoxidized soybean oil (from Arkema, Inc. of Philadelphia, Pa.) and 1.0 g Thermo-Chek SP175 thermal stabilizer (from Ferro Corp. of Cleveland, Ohio). Then 3.5 g of stabilized PVC mixture was then admixed with DOP or a polyketal compound to form a PVC/plasticizer admixture in the desired ratio. For example, to form a PVC/plasticizer mixture with 30 wt % plasticizer, 1.5 g of DOP or polyketal compound was admixed with the 3.5 g of stabilized PVC mixture.

The PVC/plasticizer mixtures were compounded using one of the standard Compounding procedures outlined in the General Laboratory Procedures section above. The glass transition temperature ($T_g$) for each extruded product was measured. The compounding of PVC with DOP and various polyketals of the invention, and the Tg of the resulting blends, is shown in Table 4.

TABLE 4

PVC compounding and resulting $T_g$ of the compounded PVC blends.

| Example No. | Compounding Procedure No. | Compounding Temp., ° C. | Polyketal, Example No. | Weight % polyketal in stabilized PVC | Tg, ° C. |
|---|---|---|---|---|---|
| 19 | 3 | 180 | None | N/A | 67.22 |
| 20 | 3 | 160 | N/A-DOP | 30 | −7 |
| 21 | 3 | 170 | 12 | 20 | 23.66 |
| 22 | 3 | 160 | 12 | 30 | −5.14 |
| 23 | 2 | 160 | 12 | 33.3 | −2.91 |
| 24 | 3 | 150 | 12 | 40 | −21.71 |
| 25 | 3 | 170 | 14 | 20 | 20.04 |
| 26 | 3 | 160 | 14 | 30 | −6.06 |
| 27 | 2 | 160 | 14 | 33.3 | −9.74 |
| 28 | 3 | 150 | 14 | 40 | −27.13 |
| 29 | 3 | 170 | 16 | 20 | 18.01 |
| 30 | 3 | 160 | 16 | 30 | −9.09 |
| 31 | 3 | 150 | 16 | 40 | −34.98 |
| 32 | 3 | 170 | 13 | 20 | 36.53 |
| 33 | 3 | 160 | 13 | 30 | 16.46 |
| 34 | 2 | 160 | 13 | 33.3 | 13.97 |
| 35 | 3 | 150 | 13 | 40 | −5.85 |
| 36 | 3 | 170 | 15 | 20 | 29.47 |
| 37 | 3 | 160 | 15 | 30 | 8.93 |
| 38 | 2 | 160 | 15 | 33.3 | 3.19 |
| 39 | 3 | 150 | 15 | 40 | −8.61 |
| 40 | 3 | 160 | 17 | 30 | 2.195 |
| 41 | 3 | 150 | 17 | 40 | −15.655 |

Examples 42-48

Various samples of compounded PVC blends were tested for durability by weight loss due to extraction and volatility according to ASTM D1239. The extractions were carried out in hexane, mineral oil, and a saturated solution of Ivory Soap (bar form, available from the Procter and Gamble Co. of Cincinnati, Ohio) obtained by flaking the soap and weighing the soap flakes and water into a flask sufficient to form a 1 wt % mixture of soap, and stirring until no further soap dissolved at ambient temperature. The weight loss from PVC, measured according to ASTM D1239, is expressed as weight percent in Table 5. The data show that one or more compounds of the invention provide extraction properties that are as good as or better than those of dioctyl phthalate.

Example 49

PVC powder type 2095 (obtained from Georgia Gulf Corporation of Atlanta, Ga.) was premixed with 1% by weight THERM-CHECK® SP175 (obtained from Ferro Corporation of Cleveland, Ohio) and 2.5% by weight epoxidized soybean oil (obtained from Arkema, Inc. of Philadelphia, Pa.) was hand mixed with PVC powder for approximately 2 minutes to form a stabilized PVC mixture. To the stabilized PVC mixture was added 33.33% by weight (50 phr) of dioctyl phthalate (obtained from the Sigma Aldrich Company of St. Louis, Mo.); this was mixed with a paddle mixer at approximately 50 rpm for 5 minutes, forming a crumbly powder.

The powder was transferred into the feed hopper of a 27 mm BRABENDER® twin-screw extruder (obtained from C.W. BRABENDER® Instruments, Inc. of South Hackensack, N.J.). The material was extruded at 155° C., 70 rpm, through a 2 mm rod die. The material was then cooled by a water bath and fed into a BRABENDER® pelletizer (obtained from C.W. BRABENDER® Instruments). Pelletized material was fed into a Nissei injection molder (obtained from Nissei America, Inc. of Anaheim, Calif.) with temperature set to 165° C. in all three heating zones as well as the nozzle. The mold was a geometry type 1 tensile bar (see General Laboratory Procedure), with temperature set at 25° C. The screw speed was set at 30% with a shot size of 5 mm and a 5% back pressure was used to fill the mold. Injection and transfer pressure was maintained at 46.5 MPa with a mold fill time of 1.01 sec, and recovery time of 11.5 sec. Automatic ejection was disabled and the parts were removed from the mold manually.

Figure 3A:
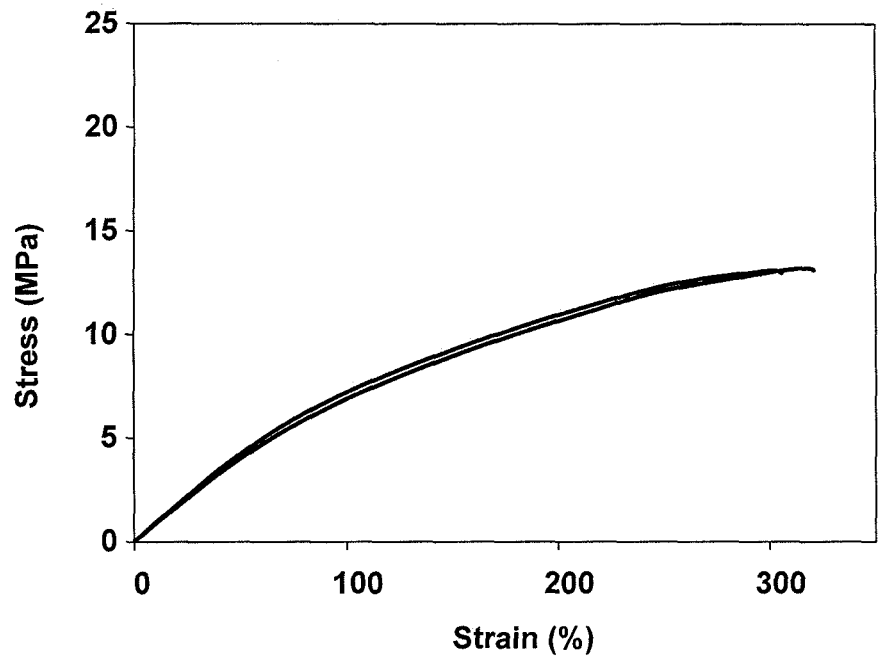
FIG. 3A-3B shows tensile data comparing a formulation of the invention to a control formulation.

The tensile properties of samples (3 samples per test) were measured according to the General Laboratory Procedure, with strain rate of 100 mm/min. The resulting plot of stress vs. strain is shown in FIG. 3A, and peak stress, percent strain at break, and Young's modulus at 2% strain are reported in Table 6.

Example 50

Figure 3B:
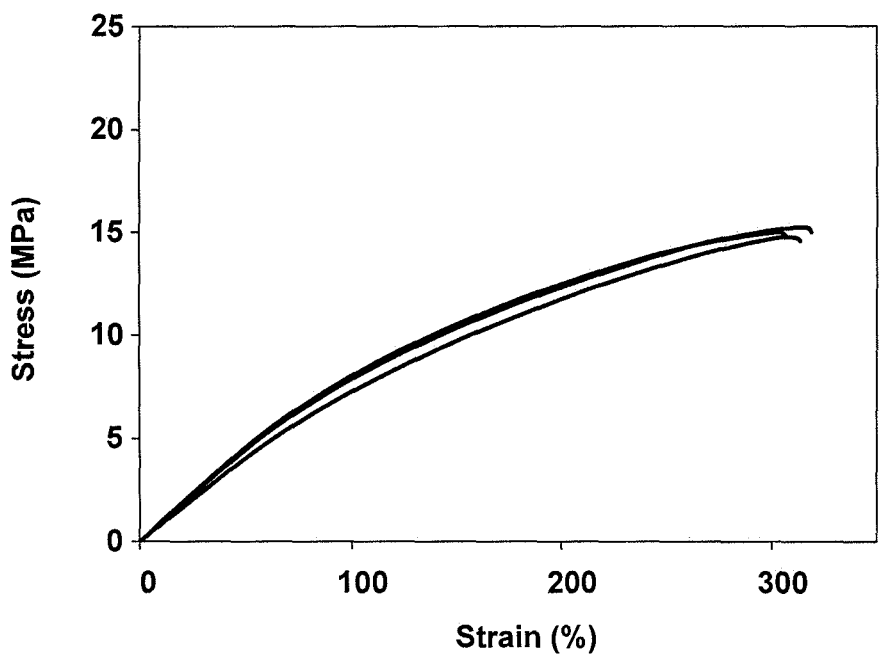

The procedure according to Example 49 was repeated, except that instead of dioctyl phthalate, 33.33% by weight (50 phr) of the polyketal compound prepared according to Example 14 was added to the stabilized PVC mixture. The resulting plot of stress vs. strain is shown in FIG. 3B, and peak stress, percent strain at break, and Young's modulus at 2% strain are reported in Table 6.

The data of Examples 49 and 50 taken together show that replacing dioctyl phthalate with the compound prepared according to Example 14 results in a compounded polymer having physical properties that are at least commensurate with those of the dioctyl phthalate compounded polymer.

TABLE 6

Tensile properties of plasticized PVC.

| Example No. | Peak Stress, Mpa | Strain at Break, % | Modulus at 2% Strain, MPa |
|---|---|---|---|
| 49 | 13.3 +/− 0.3 | 288.6 +/− 18.7 | 8.8 +/− 0.5 |
| 50 | 14.9 +/− 0.2 | 307.0 +/− 7.3 | 8.0 +/− 0.4 |

Examples 51-65

Using compounding method 1 as described in the General Laboratory Procedures section above, polyketals of the invention were compounded into various polymers, followed by DSC analysis of Tg for the blended materials. The polymers compounded were PHBV: Poly(hydroxybutyrate-co-hydroxyvalerate) from Tianan Biologic of Zhejiang Province, China PLA: Polylactic acid from NatureWorks of Minnetonka, Minn.

PS: Polystyrene from Entec Polymers of Orlando, Fla.

The blends and resulting Tg measurements are shown in Table 7.

TABLE 5

Percent weight loss of samples by extraction and volatilization.

| | | Extraction Loss, % by Weight | | | | | Volatile Loss, % by Weight | | |
|---|---|---|---|---|---|---|---|---|---|
| Example No. | Compounded Blend, Example No. | Hexane, ambient temp | Mineral oil, ambient temp | Soap, 1 wt %, ambient temp | Mineral Oil, 60° C. | Soap, 1 wt %, 60° C. | Activated carbon, 70° C. | 100% RH, 80° C. | 120° C. |
| 42 | 20 | −6.56% | −0.18% | −0.17% | −1.96% | −0.34% | −0.98% | 0.86% | 0.00% |
| 43 | 33 | 1.57% | −0.44% | 0.79% | −0.47% | 0.26% | 0.59% | 0.21% | 0.00% |
| 44 | 37 | 2.52% | −0.88% | −0.35% | −2.92% | −0.25% | −0.13% | −0.09% | −1.07% |
| 45 | 40 | −11.62% | −0.55% | 1.49% | N/A | N/A | N/A | N/A | N/A |
| 46 | 22 | 0.41% | −0.22% | 0.20% | −2.16% | −1.74% | −0.47% | 0.37% | −0.75% |
| 47 | 26 | 1.68% | −0.23% | −0.17% | −2.93% | −2.65% | 0.00% | 0.00% | −0.71% |
| 48 | 30 | −13.31% | 0.00% | 0.34% | −1.36% | −1.41% | −0.40% | 0.19% | −0.58% |

TABLE 7

Polyketal blends and resulting T$_g$ as measured by DSC.

| Example No. | Polymer | Polyketal of Example No. | Wgt % Polyketal | Tg, ° C. |
|---|---|---|---|---|
| 51 | PHBV | None | N/A | 4.53 |
| 52 | PHBV | 14 | 33.3 | <−80 |
| 53 | PHBV | 15 | 33.3 | −59 |
| 54 | PLA | None | N/A | 60.8 |
| 55 | PLA | 14 | 5 | 51.81 |
| 56 | PLA | 14 | 33.3 | 33.01 |
| 57 | PLA | 15 | 33.3 | 34.7 |
| 58 | PS | None | N/A | 96.55 |
| 59 | PS | 14 | 9.1 | 65.28 |
| 60 | PS | 14 | 23.1 | 41.83 |
| 61 | PS | 14 | 33.3 | 29.35 |
| 62 | PS | 14 | 50 | −44.83 |
| 63 | PS | 14 | 56.1 | −53.2 |
| 64 | PS | 13 | 33.3 | 24.08 |
| 65 | PS | 13 | 50 | −43.59 |

Example 66

A 250 ml 3-neck round bottom flask was charged with 20.05 grams (0.03 mol) of the compound prepared according to Example 13 and 1.61 grams (0.018 mol) of butane diol. The flask was equipped with a Dean Stark trap and condenser, a magnetic stirrer, and a thermocouple. The flask was heated to 140° C. at which point 0.96 g of titanium IV isopropoxide was added to the reaction flask via a 3 ml syringe. Nitrogen purge of the reaction flask was started while stirring the contents of the flask at 170 rpm. The temperature in the flask was raised over 1 hour to 180° C., then held at that temperature for 30 minutes, followed by raising the temperature to 190° C. and holding at that temperature for 30 additional minutes. Vacuum was then applied to the reaction flask, slowly bringing the pressure down to 200 torr. This pressure was maintained, and liquid was observed to collect in the Dean Stark trap. After 30 minutes, the temperature was increased to 200° C. and the vacuum was increased to 100 torr for an additional 30 minutes. Additional liquid was collected in the Dean Stark trap.

The contents of the Dean Stark trap were weighed and determined to represent 94 weight percent yield based on expected loss of ethanol.

Example 67

A 100 ml 3-neck round bottom flask was charged with 50.1 grams (0.12 mol) of the compound synthesized according to Example 14 and 5.25 grams (0.06 mol) of anhydrous butane diol (obtained from the Sigma-Aldrich Company of St. Louis, Mo.). The flask was equipped with Dean Stark trap and condenser, magnetic stirrer, nitrogen purge and a thermocouple. The flask was heated to 130° C. at which point 2 µL of titanium IV isopropoxide was added to the reaction flask by injecting it under the liquid level of the contents of the reaction flask via a metered microliter pipette. The reaction was heated to 210° C. over 40 minutes. Liquid was observed to collect in the Dean Stark trap. The reaction was allowed to react at 210° C. for 90 minutes, followed by 6.5 hours at 220° C. The contents of the flask were allowed to cool to ambient temperature under the nitrogen purge.

The reaction contents were analyzed by GPC. The peak percent area is shown in Table 8. The peak at retention time 9.353 corresponds to the compound of Example 14.

TABLE 8

Retention times and corresponding height and areas for the GPC peaks.

| Retention Time (min) | Area | % Area | Height |
|---|---|---|---|
| 8.169 | 219189 | 32.72 | 6645 |
| 8.423 | 126093 | 18.82 | 9096 |
| 8.779 | 171603 | 25.61 | 12564 |
| 9.353 | 153088 | 22.85 | 13412 |

Example 68

A 250 ml, 4-neck flask was charged with 100.0 g (0.267 mol) of the compound synthesized according to Example 12 and 51.05 g (0.419 mol) of 1,6-hexane diol (obtained from Acros Organics of Geel, Belgium). The flask was equipped with a magnetic stir bar, Dean Stark trap and condenser, thermocouple, and nitrogen inlet. The reaction flask was stirred and a vacuum was applied to a pressure of about 15 torr. While under vacuum, the flask was heated to 100° C. using a heating mantle and held at that temperature for 30 minutes. The vacuum was released and nitrogen was streamed in through the inlet. The flask was briefly opened and 30 µl of titanium isopropoxide (obtained from Acros Organics) was added neat, using a metered microliter pipette. The nitrogen stream was maintained with stirring, and the temperature of the reaction flask was increased to 200° C. Liquid was observed to collect in the Dean Stark trap. After 3 hours, liquid was observed to stop collecting in the Dean Stark trap. At this point, the trap was observed to hold 30.0 ml of liquid. The theoretical yield of ethanol in the reaction is 31.2 ml.

The contents of the reaction flask were cooled to ambient temperature. The contents of the reaction flask were analyzed by $^1$H NMR, and $^{13}$C NMR, GPC, and hydroxyl number. The NMRs showed no traces of ethyl ester or ethanol. The GPC data gave Mn of 1107 and Mw of 2909, for a polydispersity index of 1.8. Hydroxyl number was measured as 125 (theoretical 112), indicating molecular weight of 898.

Example 69

A 1 liter, 4 neck roundbottom flask was charged with 198.5 g (1.68 mol) 1,6-hexanediol (obtained from Acros Organics of Geel, Belgium) and 400 g (1.07 mol) of the compound synthesized according to Example 12. The flask was equipped with a thermocouple and Dean-Stark trap and condenser having a vacuum adapter. The horizontal glass tubing leading to the Dean-Stark trap was wrapped with heat tape. The apparatus was attached to a vacuum pump. The flask was heated to 100° C. using a heating mantle, and a vacuum of about 7-8 torr was applied to the flask for 30 to 60 minutes to dry and melt the 1,6-hexanediol.

The vacuum was released and the vacuum adapter was replaced with a connection to a bubbler. The round-bottom flask was further fitted with a mechanical stirrer and a nitrogen inlet. A moderate flow of nitrogen gas was swept through the headspace of the flask, and the controller for the heat tape was set to 2.5 out of a possible 10. Stirring was begun, and 120 µL (200 ppm based on total reactor charge) titanium tetrabutoxide (obtained from Acros Organics) was added via metered micropipette. The temperature set point of the controller was increased to 200° C. When the temperature inside the flask was observed to reach 170° C., a liquid was observed to begin collecting in the Dean-Stark trap. The reaction was continued until 125 mL of liquid had collected. The flask was cooled to ambient temperature and the contents of the flask were poured into a sealed bottle for storage.

$^{13}C$ and $^1H$ NMR analysis of the cooled flask contents showed no remaining ethanol or ethyl ester groups. GPC showed a small amount of residual 1,6-hexanediol but none of the compound of Example 12. Brookfield viscosity of the polyol was 9313 cP at 25° C. and 282 cP at 80° C. The hydroxyl value was 131 (theoretical value: 56). The glass transition temperature as determined by DSC was −49° C. No melting endotherm was observed.

Example 70

A 3-necked, 100 mL round bottom flask was charged with 50.1 g (0.13 mol) of the compound prepared according to Example 12 and 18.1 g (0.17 mol) of diethylene glycol (DEG, obtained from Fisher Scientific of Waltham, Mass.). The flask was equipped with an overhead mechanical stirrer, an inlet for nitrogen, and a Dean-Stark trap with overhead condenser and nitrogen inlet. The flask was purged with nitrogen and degassed with three vacuum/nitrogen cycles at room temperature, and then a nitrogen sweep was applied through the flask. The contents of the flask were then warmed to 173° C. under nitrogen purge. After the contents reached 173° C., 8.0 µl of titanium IV isopropoxide (obtained from the Sigma-Aldrich Company of St. Louis, Mo.) was injected into the reaction mixture under nitrogen purge. The nitrogen sweep was then discontinued. A J-KEM® Temperature Controller (obtained from J-KEM® Scientific, Inc. of St. Louis, Mo.) was used to monitor the temperature of an oil bath that was heated by a hot plate. The temperature was controlled by successive changes in the temperature setting of the hot plate. The temperature reached about 215° C. after about 130 minutes total reaction time, then was ramped to 230° C. over about the next 60 minutes and was held at between about 230° C. and 235° C. for the remainder of the reaction. Nitrogen was sweep was restarted after about 112 minutes of reaction time, when it was noticed that liquid had stopped collecting in the Dean Stark trap. After about 183 minutes after nitrogen sweep was restarted, the rate of liquid collection in the Dean Stark trap slowed down once again, and vacuum was applied to the system. The vacuum was observed to ramp from about 30 torr to about 5 torr over about 50 minutes. When no further liquid was observed to collect in the Dean Stark trap, the reaction was shut down by cooling the reaction to ambient temperature and releasing the vacuum. The total heating reaction time was about 353 minutes.

Figure 4:
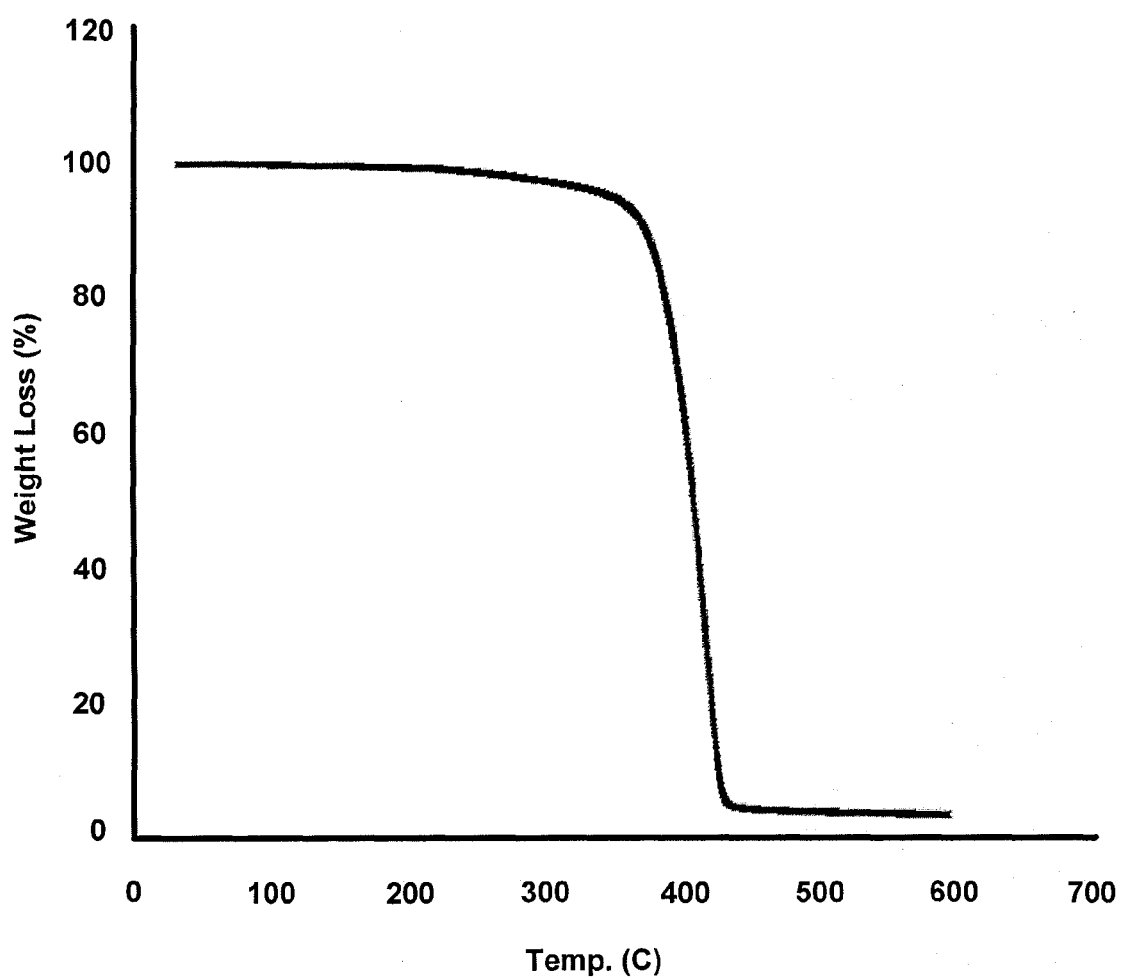
FIG. 4 shows thermogravimetric data for a compound of the invention.

The material in the reaction flask was light orange in color, viscous, transparent, and soluble in THF. The material was analyzed by GPC, DSC, and TGA. The weight average molecular weight was 163,798 g/mol; number average molecular weight was 10,920 g/mol, for a polydispersity of 15. DSC gave a glass transition temperature of −7° C. The TGA showed that the polymer was thermally stable up to a temperature of about 300° C. The TGA plot is shown in FIG. 4.

Examples 71-74

Using the synthetic technique employed in Example 70, additional copolymers were made using the polyketal compound of Example 12. Table 9 shows materials used, time of reaction, and GPC and DSC data measured for polymers made with 1,2-ethanediol (obtained from Fisher Scientific of Waltham, Mass.), 1,4-butanediol (obtained from Riedel-de-Haën Fine Chemicals of Seelze, Germany), 1,6-hexanediol (obtained from Acros Organics of Geel, Belgium) and 1,10-decanediol (obtained from Acros Organics). All polymers were transparent, and were colorless to orange in color.

TABLE 9

Synthetic data and measurements for polymers made from the polyketal of Ex. 12.

| Example No. | Diol | Diol, mol | Polyketal, mol | TPT, mol | Reaction time, min | $M_w$, g/mol | $M_n$, g/mol | Polydispersity index | Tg, ° C. |
|---|---|---|---|---|---|---|---|---|---|
| 71 | 1,2-ethane diol | 0.21 | 0.14 | $2.8 \times 10^{-5}$ | 345 | 7638 | 5875 | 1.3 | −7 |
| 72 | 1,4-butane diol | 0.18 | 0.14 | $2.7 \times 10^{-5}$ | 390 | 34174 | 6572 | 5.2 | −13 |
| 73 | 1,6-hexane diol | 0.17 | 0.14 | $2.7 \times 10^{-5}$ | 420 | 123658 | 9368 | 13.2 | −17 |
| 74 | 1,10-decane diol | 0.96 | 0.96 | $2.7 \times 10^{-5}$ | 415 | 54304 | 7758 | 7 | −33 |

Example 75

A 1 liter, 3-neck flask was charged with 351.8 g (0.940 mol) of the compound synthesized and purified according to Example 12 and 138.7 g (1.17 mol) of 1,6-hexane diol (obtained from Acros Organics of Geel, Belgium). The flask was equipped with a magnetic stir bar, Dean Stark trap and condenser, thermocouple, and nitrogen inlet. The reaction flask was stirred and a vacuum was applied to a pressure of 15 torr. While under vacuum, the flask was heated to 100° C. using a heating mantle and held at that temperature for 30 minutes. The vacuum was then released and nitrogen was streamed in through the inlet. The flask was briefly opened and 98 µl (200 ppm) of titanium isopropoxide (obtained from Acros Organics) was added neat, using a metered pipette. The nitrogen stream shut off and the flask was stirred and the temperature of the reaction flask was increased to 200° C. Liquid was observed to collect in the Dean Stark trap. After 2 hours, 48 ml of a liquid had collected in the Dean Stark trap and the rate of collection had slowed significantly. At this point, a nitrogen sweep through the flask was started and an additional 19.5 ml of liquid was observed to collect in the Dean Stark trap over the next 3 hours. At this point, a total of 67.5 ml of liquid had been collected. The theoretical yield of ethanol in the reaction is 68.3 ml. The contents of the reaction flask were cooled to ambient temperature.

The polyol contents of the reaction flask were analyzed by GPC, Brookfield viscosity, DSC and hydroxyl number. The GPC data gave Mn of 1975 and Mw of 4720, for a polydispersity index of 2.4. Hydroxyl number was 69 (theoretical 56), indicating molecular weight of 1626. Brookfield viscosity at 80° C. was 1837 cP. DSC gave a glass transition temperature of −31° C.

A 250 ml, 3-neck round bottom flask was charged with 200.0 g of the polyol synthesized in the above reaction. The flask was equipped with a magnetic stir bar, a nitrogen inlet, a nitrogen outlet, and a thermocouple. The flask was placed in a heating mantle and heated to 80° C. Nitrogen was blown in through the inlet and out of the outlet while the temperature was maintained with stirring for approximately 16 hours to result in the dried reaction product. A 500 ml resin kettle was charged with 60.49 g (0.242 mol) of methylene diphenyl-4,4'-diisocyanate (MDI, obtained from the Sigma-Aldrich Company of St. Louis, Mo.). The resin kettle was then clamped to its lid, which was equipped with a mechanical stirrer, nitrogen inlet, nitrogen outlet, and a thermocouple. Nitrogen was flowed through the inlet and out of the outlet, with stirring, while the flask was heated to 80° C. using a heating mantle. To the flask was added 164.5 g (0.10 mol) of the dried polyol. The heat and stirring were maintained for 3 hours, after which isocyanate value was measured by removing a sample from the resin kettle. The isocyanate number was measured to be 3.0 weight percent. The theoretical value was 5.3 weight percent.

A 250 ml, 3-neck roundbottom flask was charged with an undetermined amount of 1,3-propanediol (obtained from Sigma-Aldrich Company). The flask was equipped with nitrogen inlet, nitrogen outlet, thermocouple, and a magnetic stir bar, and heating with stirring and nitrogen flow for approximately 16 hours at 80° C., to provide dried 1,3-propanediol. A 20.0 g aliquot of the dried 1,3-propanediol were removed from the drying flask and placed in a beaker along with 50 of dibutyltin dilaurate (obtained from Air Products and Chemicals, Inc. of Allentown, Pa.).

The diol and tin catalyst were mixed briefly by hand, and then 5.7 g of the mixture was added to the resin flask containing the reaction product of above, which had been preheated to 80° C. under nitrogen flow. The mixture of was stirred for approximately 2 minutes.

The contents of the resin flask were partially emptied into a custom made Teflon mold measuring 25.4 cm×25.4 cm×0.5 mm. The mold was preheated in an oven to 110° C. After filling the mold with the mixture from the resin flask, the mold was covered with Teflon coated aluminum foil (BYTAC®, obtained from Fisher Scientific of Waltham, Mass.). A second sheet of Teflon coated aluminum foil was placed under the mold. A 0.1524 cm thick steel plate was placed on top and a second plate placed beneath the Teflon covered aluminum foil, to form a compression molding "sandwich". The sandwich was placed in a Carver Model 4122 pneumatic heated platen press (obtained from Carver, Inc. of Wabash, Ind.) of that was preheated to 105° C. The press was closed and pressure of 5,000 lbs applied to the sandwich. The heat and pressure were maintained for 1 hour. The mold was then removed from the press and placed in an oven at 110° C. for 24 hours. The sample was removed from the oven and a solid, flexible molded sheet comprising the material from the resin flask was removed from the mold.

A second compression molding sandwich was formed by layering the molded sheet on its two major sides Teflon coated aluminum foil sheets and steel plates. The second sandwich was placed in the press that was preheated to 192° C. The platens of the press were closed so as to contact the sandwich but without adding measurable pressure. This position was maintained for approximately 3 minutes in order to preheat the sandwich. The pressure was then increased to 5,000 lbs. and this was maintained for 5 minutes. The sandwich was removed from the press and allowed to cool for approximately 1 minute before removing a pressed film from the sandwich.

The pressed film was measured to be about 0.5 mm thick, was substantially uniform and without bubbles, was transparent, and had a very slight yellow color. The pressed film was characterized by DMA, DSC, and tensile testing. The DMA showed that the peak of the tan δ was at 33.1° C. DSC showed that the $T_g$ was 13.0° C. with a broad melting peak at about 208° C. Tensile testing was carried out according to ASTM D1708, using 100 mm/min; the strain at break was 409%, peak stress was 25.1 MPa; modulus was 6.40 MPa at 2% strain, 6.87 MPa at 100% strain, and 4.30 MPa at 300% strain.

Example 76

A 250 ml 4-neck round bottom flask was charged with 44.48 g (0.229 mol) of dimethyl terephalate (DMT, obtained from the Sigma-Aldrich Company of St. Louis, Mo.), 50.60 g (0.135 mol) of the compound made according to Example 12, and 49.86 g (0.553 mol) of 1,4-butane diol (obtained from the Sigma Aldrich Chemical Company). The flask was equipped with a Dean Stark trap and condenser, a nitrogen/vacuum inlet, and a mechanical stirrer. The flask was degassed with 5 vacuum/nitrogen cycles wherein the vacuum applied to the flask was approximately 9 torr. After the 5 degassing cycles, 29.3 μl (200 ppm) of titanium tetrabutoxide (obtained from Acros Organics of Geel, Belgium) was injected into the contents of the reaction flask with a metered micro pipette, and the contents of the reaction flask were degassed an additional 5 times. The flask was placed in an oil bath with the temperature set to 180° C. and was stirred, under nitrogen, for 2.5 hours after which time the oil bath temperature was increased to 190° C. and this temperature was maintained for 105 minutes; the temperature was then raised again to 200° C. and this temperature maintained for an additional 2 hours. Vacuum was then applied to the flask with a Teflon pump and over the ensuing 50 minutes, the pressure in the reaction flask decreased from about 75 torr to 25 torr. A second Teflon pump was then added in tandem with the first Teflon pump and the vacuum in the reaction flask was brought down to 5.5 torr; this pressure was maintained for about 2 hours and 45 minutes. The temperature in the flask was then slowly raised to 210° C. over the next 2.5 hours. The temperature of 210° C., and the pressure of 5.5 torr were maintained for the next 10.5 hours. Then the pressure in the flask was reduced again by replacing the Teflon pumps with an oil pump; the pressure in the reaction flask went from 1 torr to about 300 millitorr and this pressure was maintained for about 1.5 hours. The reaction flask was then backfilled with nitrogen and allowed to cool to ambient temperature.

The contents of the reaction flask were analyzed by GPC, DSC, and tensile testing. The GPC gave a weight average molecular weight of 232,000 g/mol and a polydispersity index of 17. The DSC gave a glass transition temperature of 4° C., a melting temperature of 133° C., and a heat of fusion $\Delta H_m$ of 23.4 J/g. The tensile testing, which was carried out with six samples employing the technique of ASTM D638, showed that the force at break was 13.0 MPa and a strain at break was 620%. The stress-strain profile for the six samples is shown in FIG. 5.

Figure 5:
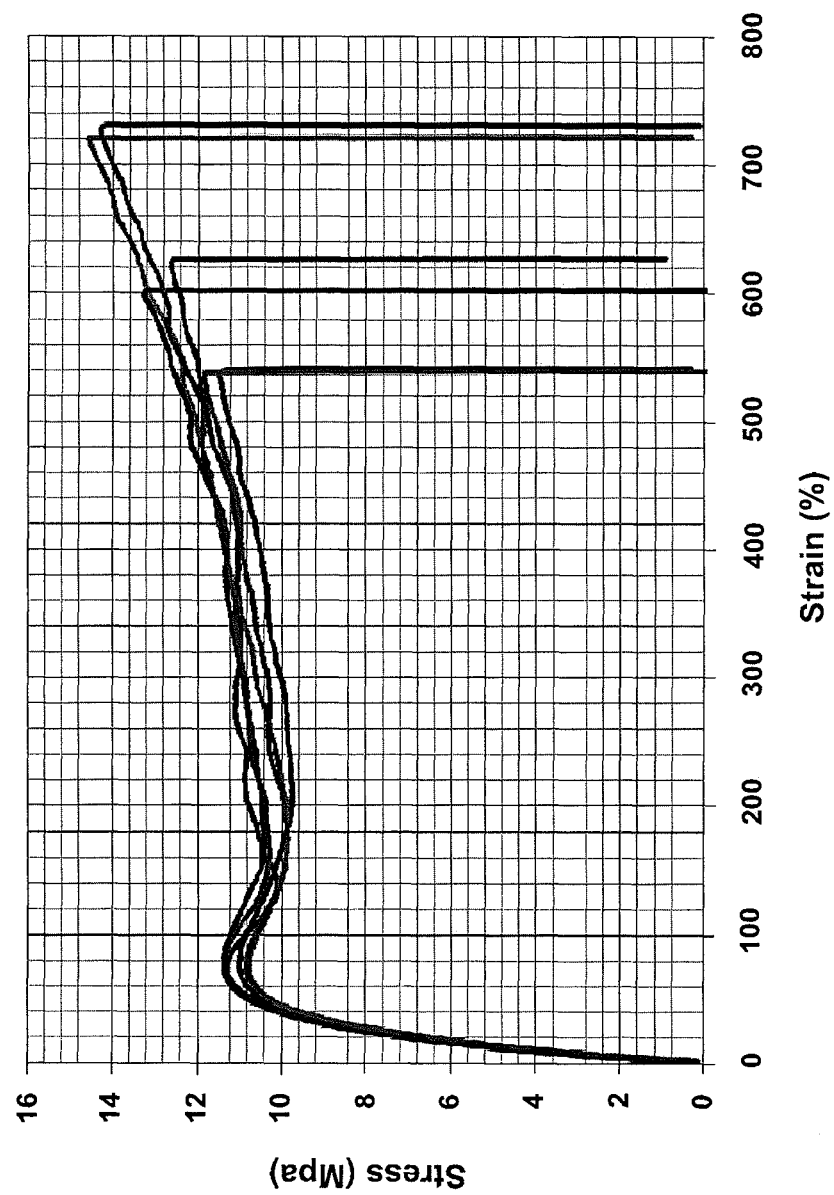
FIG. 5 shows tensile data for a compound of the invention.

The data in FIG. 5 show that the polyesters of the invention have tensile properties that make them suitable for use as structural materials. Packaging films, fibers, and other articles suitable for commercial applications can be made using the polyketal polyesters of the invention.

Examples 77-79

The glycerol ketal of butyl levulinate was synthesized and purified according to the procedures set forth in U.S. patent application Ser. No. 11/915,549. A copolymer of the glycerol ketal of butyl levulinate with butylene terephthalate (obtained from the Sigma-Aldrich Company of St. Louis, Mo.), or p(LGK-co-BT), was synthesized according to the techniques set forth in U.S. patent application Ser. No. 11/915,549. The molar ratio of monomers was 1:1. The molecular weight of the p(LGK-co-BT) copolymer was analyzed by GPC, which determined that the weight average molecular weight was about 215,000 with a polydispersity index of 10.

The materials were mixed with the polyketal synthesized and purified according to Example 14 using the procedure outlined in the General Laboratory Procedures for compounding using the Haake PolyLab, with the following modifications. The polymer and polyketal were fed into the compounder via a gravity feed system without hand mixing, and the temperature in the compounder was set to 140° C.

After compounding, the mixtures were analyzed by DSC to determine glass transition temperature and melt temperature. The mixtures and the DSC results are shown in Table 10.

TABLE 10

Effect on Tg, Tm of p(LGK-co-BT) when blended with the polyketal of Example 14.

| Example | Polyketal of Example 14, wt % | Tg (° C.) | Tm (° C.) |
|---|---|---|---|
| 77 | 0 | 16 | 115 |
| 78 | 10 | −4 | 112 |
| 79 | 20 | −16 | 111 |

Examples 80-85

The ability of the compounds of the invention to compatibilize mixtures of solvents that are otherwise immiscible was tested in the following six experiments.

Example 80

Equal volumes of hexane and methanol were place in a scintillation vial. The two solvents formed two clear and distinct layers. About 10 vol % of the polyketal synthesized according to the procedure of Example 14 was added based on the volume of the combined solvents. Upon brief shaking by hand, the two immiscible liquids formed a single layer.

Example 81

Equal volumes of water and methanol were placed in a scintillation vial. The two solvents formed two clear and distinctly visible layers. About 10 vol % of the polyketal synthesized according to the procedure of Example 14 was added based on the volume of the combined solvents. Upon brief shaking by hand, the two immiscible liquids formed a single layer.

Example 82

A centrifuge vial was charged with 3 ml methanol and 3 ml hexane. 80 µL of the compound synthesized and purified according to the procedure of Example 12 was added to the vial. Upon brief shaking by hand, most of the solvent mixture was homogeneous in appearance, with a very small layer of separated solvent remaining on the top of the volume of liquid. An additional 20 µL of the compound synthesized and purified according to the procedure of Example 12 was added to the vial. Upon brief shaking by hand, the mixture became completely homogeneous in appearance. The sample was then placed in a centrifuge and spun at 3000 rpm for about 10 minutes and was still a homogeneous mixture upon removal from the centrifuge.

Example 83

A centrifuge vial was charged with 3 ml methanol and 3 ml hexane. 80 µL of the compound synthesized and purified according to the procedure of Example 14 was added to the vial. Upon brief shaking by hand, most of the solvent mixture was homogeneous in appearance, with a very small layer of separated solvent remaining on the top of the volume of liquid. An additional 20 of the compound synthesized and purified according to the procedure of Example 14 was added to the vial. Upon brief shaking by hand, the mixture became completely homogeneous in appearance. The sample was then placed in a centrifuge and spun at 3000 rpm for about 10 minutes and was still a homogeneous mixture upon removal from the centrifuge.

Example 84

A centrifuge vial was charged with 3 ml water and 3 ml dichloromethane. Aliquots of the compound synthesized and purified according to the procedure of Example 12 was added to the vial, with brief hand shaking between aliquots. After a total of about 3 ml of the compound synthesized and purified according to the procedure of Example 12 was added, the sample did not become homogeneous.

Example 85

The procedure of Example 81 was repeated using the compound synthesized and purified according to the procedure of Example 14, with the same result.

Examples 86-89

Various polyketal compounds according to the invention were mixed with Rhoplex SG10M Latex (obtained from the Rohm and Haas Company of Philadelphia, Pa.). In each case, 0.25 g of the polyketal compound was added to 5.0 g of latex in a scintillation vial, and the vial was mixed by placing on a vortex shaker for 1 minute. The mixtures were then cast onto cleaned glass panels using a 6 mil (0.254 mm) notched draw down bar (obtained from the Pioneer-Dietecs Corporation of Weymouth, Mass.). These panels were then placed into a refrigerator at 4° C. for 2 hours. The resulting films were 3 mil thick. The films were examined visually for continuity of the film and for surface defects. The result of visual examination of the films is reported in Table 11.

TABLE 11

Visual assessment of films formed from blends of commercial latex with polyketal compounds.

| Example No. | Polyketal, Ex. No. | Appearance of Film |
|---|---|---|
| 86 | none | discontinuous film |
| 87 | 12 | continuous film, some fish eyes or air bubbles |
| 88 | 14 | discontinuous film, some fish eyes or air bubbles |
| 89 | 15 | discontinuous film, some fish eyes or air bubbles |

Examples 90-101

Smooth finish steel panels (obtained from the Q-Lab Corporation of Westlake, Ohio) were cleaned by washing four times with acetone, followed by wiping with a KIMWIPE® (obtained from the Kimberly-Clark Corporation of Irving, Tex.). The panels were then coated with paint samples by spraying or brushing a commercial paint formulation onto a panel and allowing the paint to dry for about 24 hours under ambient laboratory conditions. The commercial paint formulations used were:

1. Appliance Epoxy—Gloss White Rustoleum 7881, obtained from the Rust-Oleum Corporation, of Vernon Hills, Ill.
2. Zinsser Bulls Eye 1-2-3 Deep Tint (white), obtained from William Zinsser & Company, Inc. of Somerset, N.J.
3. Promar 200 Interior Latex Low Sheen ES Enamel, Extra White. B20w1251, obtained from the Sherwin-Williams Company of Cleveland, Ohio
4. Rhoplex SG10M latex, obtained from the Rohm and Haas Company of Philadelphia, Pa.

The panels were laid flat on a laboratory bench, and two drops of a polyketal were applied by a plastic eyedropper to each panel. The panel was undisturbed for about 10 minutes. Then the panels were wiped off using a KIMWIPE®. The wiped surfaces of the panels were visually inspected. The results of visual inspection are shown in Table 12.

TABLE 12

Observations after applying polyketal compounds to paint coated steel panels, followed by wiping the areas of application.

| Example No. | Paint Formulation, No. | Polyketal, Example No. | Observations |
|---|---|---|---|
| 90 | 1 | 12 | No effect on film |
| 91 | 1 | 14 | No effect on film |
| 92 | 1 | 15 | No effect on film |
| 93 | 2 | 12 | Penetrated and removed surface layer of film. Definite circle where solvent was applied. |
| 94 | 2 | 14 | Penetrated and removed surface layer of film. Definite circle where solvent was applied. |
| 95 | 2 | 15 | No effect on film |
| 96 | 3 | 12 | Penetrated and removed surface layer of film. Removed down to bare metal in places. Definite circle where solvent was applied. |
| 97 | 3 | 14 | Penetrated and removed surface layer of film. Removed down to bare metal in places. Definite circle where solvent was applied. |
| 98 | 3 | 15 | Penetrated and removed surface layer of film. Definite circle where solvent was applied. |
| 99 | 4 | 12 | Penetrated and removed surface layer of film. Removed down to bare metal. Definite circle where solvent was applied. |
| 100 | 4 | 14 | Penetrated and removed surface layer of film. Removed down to bare metal. Definite circle where solvent was applied. |
| 101 | 4 | 15 | Penetrated and removed surface layer of film. Removed down to bare metal. Definite circle where solvent was applied. |

The present invention may suitably comprise, consist of, or consist essentially of, any of the disclosed or recited elements. The invention illustratively disclosed herein can be suitably practiced in the absence of any element which is not specifically disclosed herein. The various embodiments described above are provided by way of illustration only and should not be construed to limit the claims attached hereto. It will be recognized that various modifications and changes may be made without following the example embodiments and applications illustrated and described herein, and without departing from the true spirit and scope of the following claims.

What is claimed:

1. A polyketal having structure I:

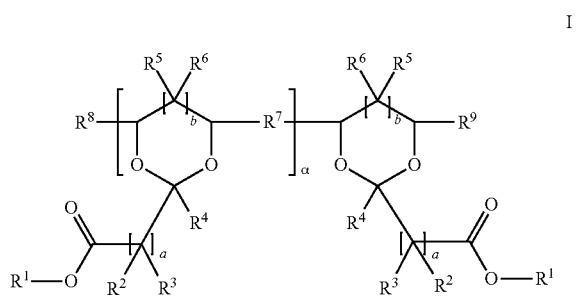

wherein

α is 1 or 2;

$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ is the same or different for each occurrence;

$R^2$, $R^3$, $R^5$ and $R^6$ are independently hydrogen, a linear, branched, or cyclic alkyl, a linear, branched or cyclic alkenyl, alkynyl, aryl, or alkaryl; and optionally contains one or more heteroatoms; $R^2$, $R^3$, $R^4$, $R^5$ and $R^6$ is the same or different for each occurrence;

$R^4$ is a linear, branched, or cyclic alkyl, a linear, branched or cyclic alkenyl, alkynyl, aryl, or alkaryl; and optionally contains one or more heteroatoms; and $R^4$ is the same or different for each occurrence;

$R^7$ is a covalent bond, methylene, ethylene, or $-CH_2-O-CH_2-$ and $R^7$ is the same or difference for each occurrence, provided that when α is 1, $R^7$ is not $-CH_2-O-CH_2-$;

$R^8$ and $R^9$ are hydrogen;

a is 0 or an integer of 1 to 12 wherein a is the same or different for each occurrence; and b is 0 or 1, wherein b=0 indicates a five membered ring,

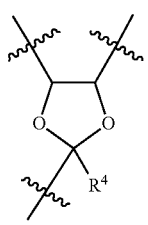

and b=1 indicates a 6 membered ring,

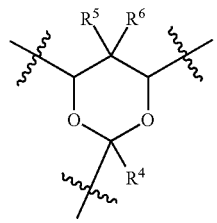

and b is the same or different for each occurrence.

2. A formulation comprising one or more polyketals of claim 1 and one or more polymers or solvents.

3. An article comprising the formulation of claim 2.

4. The polyketal of claim 1 wherein in all $R^2$ and $R^3$ are hydrogen, all $R^4$ are methyl, and all $R^7$ are covalent bonds.

5. The polyketal of claim 4 wherein all a are 2, all b are 0, $R^8$ and $R^9$ are hydrogen, and all $\alpha$ are 1 or 2.

6. The polyketal of claim 1 wherein $R^1$ is ethyl, butyl, or 2-ethylhexyl.

7. The polyketal of claim 1 wherein $R^1$ is the residue of a polyol.

8. The polyketal of claim 1 wherein $R^1$ comprises isocyanate, acrylate, methacrylate, allyl, or oxiranyl groups.

9. The formulation of claim 2 wherein the polymer is poly(3-hydroxybutyrate-co-hydroxyvalerate), poly(vinyl chloride), poly(lactic acid), or polystyrene.

10. The formulation of claim 2 wherein the formulation is a coating formulation.

11. The polyketal of claim 1 having the structure V:

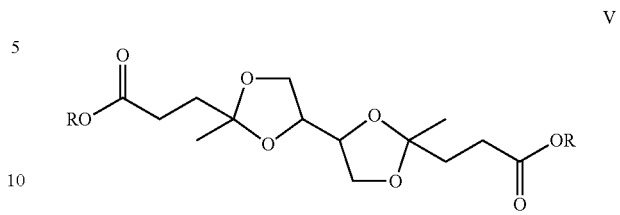

wherein each R is independently an ethyl group or a linear or branched butyl group.

12. The polyketal of claim one having the structure VI:

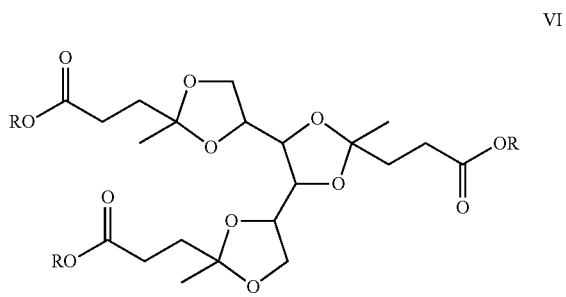

wherein each R is independently an ethyl group or a linear or branched butyl group.

13. The polyketal of claim 1, wherein $R^7$ is a covalent bond, methylene or ethylene, and $R^7$ is the same or different for each occurrence.

* * * * *